United States Patent
O'Sullivan et al.

(10) Patent No.: US 9,867,371 B2
(45) Date of Patent: Jan. 16, 2018

(54) 4-MEMBERED RING CARBOXAMIDES USED AS NEMATICIDES

(71) Applicant: SYNGENTA PARTICIPATIONS AG, Basel (CH)

(72) Inventors: Anthony Cornelius O'Sullivan, Stein (CH); Regis Jean Georges Mondiere, Stein (CH); Olivier Loiseleur, Stein (CH); Tomas Smejkal, Stein (CH); Torsten Luksch, Stein (CH); Andre Jeanguenat, Stein (CH); Raphael Dumeunier, Stein (CH); Edouard Godineau, Stein (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/903,169

(22) PCT Filed: Jul. 1, 2014

(86) PCT No.: PCT/EP2014/063895
§ 371 (c)(1),
(2) Date: Jan. 6, 2016

(87) PCT Pub. No.: WO2015/003951
PCT Pub. Date: Jan. 15, 2015

(65) Prior Publication Data
US 2016/0157485 A1    Jun. 9, 2016

(30) Foreign Application Priority Data

Jul. 8, 2013 (EP) .................................... 13175632
Jul. 10, 2013 (EP) .................................... 13175940

(51) Int. Cl.
| | | |
|---|---|---|
| A01N 27/00 | (2006.01) |
| A61K 31/015 | (2006.01) |
| A01N 37/18 | (2006.01) |
| C07D 213/81 | (2006.01) |
| C07D 231/14 | (2006.01) |
| C07D 239/28 | (2006.01) |
| C07C 233/66 | (2006.01) |
| C07C 255/57 | (2006.01) |
| C07C 291/10 | (2006.01) |
| C07C 211/37 | (2006.01) |
| C07C 317/32 | (2006.01) |
| C07C 323/62 | (2006.01) |
| C07C 233/14 | (2006.01) |
| C07C 233/81 | (2006.01) |
| C07C 235/54 | (2006.01) |
| C07C 235/62 | (2006.01) |
| A01N 37/34 | (2006.01) |
| A01N 37/40 | (2006.01) |
| A01N 43/20 | (2006.01) |
| A01N 43/40 | (2006.01) |
| C07C 233/23 | (2006.01) |
| C07C 233/32 | (2006.01) |
| C07C 233/90 | (2006.01) |
| C07C 251/44 | (2006.01) |
| C07C 265/10 | (2006.01) |
| C07D 213/82 | (2006.01) |
| C07D 263/52 | (2006.01) |
| C07D 305/08 | (2006.01) |

(52) U.S. Cl.
CPC ............. *A01N 37/18* (2013.01); *A01N 37/34* (2013.01); *A01N 37/40* (2013.01); *A01N 43/20* (2013.01); *A01N 43/40* (2013.01); *C07C 211/37* (2013.01); *C07C 233/14* (2013.01); *C07C 233/23* (2013.01); *C07C 233/32* (2013.01); *C07C 233/66* (2013.01); *C07C 233/81* (2013.01); *C07C 233/90* (2013.01); *C07C 235/54* (2013.01); *C07C 235/62* (2013.01); *C07C 251/44* (2013.01); *C07C 255/57* (2013.01); *C07C 265/10* (2013.01); *C07C 291/10* (2013.01); *C07C 317/32* (2013.01); *C07C 323/62* (2013.01); *C07D 213/81* (2013.01); *C07D 213/82* (2013.01); *C07D 231/14* (2013.01); *C07D 239/28* (2013.01); *C07D 263/52* (2013.01); *C07D 305/08* (2013.01); *C07B 2200/07* (2013.01); *C07C 2601/04* (2017.05)

(58) Field of Classification Search
None
See application file for complete search history.

(56) References Cited

FOREIGN PATENT DOCUMENTS

CN    1069882 A     3/1993
CN    104203916 A   12/2014
(Continued)

OTHER PUBLICATIONS

International Search Report & Written Opinion for PCT/EP2014/063895, dated Sep. 4, 2014.
(Continued)

*Primary Examiner* — Jeffrey S Lundgren
*Assistant Examiner* — Stephanie K Springer
(74) *Attorney, Agent, or Firm* — James Cueva

(57) ABSTRACT

Compounds of the formula (I), in which the substituents are as defined in claim 1, are suitable for use as nematicides.

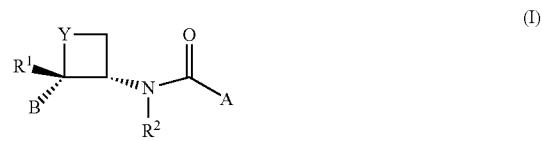

(I)

17 Claims, 1 Drawing Sheet

(56) References Cited

FOREIGN PATENT DOCUMENTS

Figure 1:
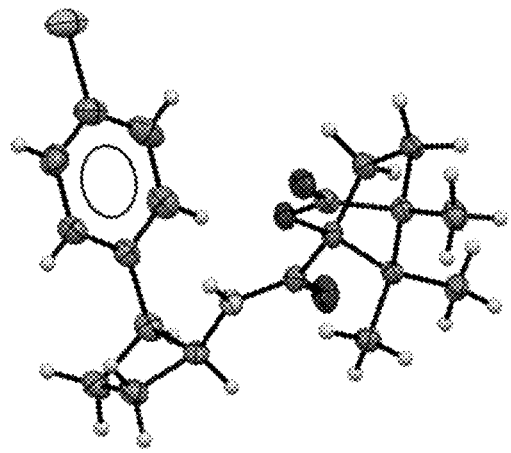

| CN | 105377036 A | 3/2016 |
|---|---|---|
| WO | 1993/003022 A1 | 2/1993 |
| WO | 2004014842 A1 | 2/2004 |
| WO | 2006/122955 A1 | 11/2006 |
| WO | 2013/064460 A1 | 5/2013 |
| WO | 2014/177487 A1 | 11/2014 |
| WO | 2013143811 A1 | 10/2015 |

OTHER PUBLICATIONS

Nichols, David E. &al: "Synthesis and Evaluation of Substituted 2-Phenylcyclobutylamines as Analogues of Hallucinogenic Phenethylamines: Lack of LSD-like Biological Activity", Journal of Medicinal Chemistry, American Chemical Society, us, vol. 27, No. 9, Jan. 1, 1984 (Jan. 1, 1984), pp. 1108-1111. XP002451512, ISSN: 0022-2623, DOI: 10.1021/JM00375A004.

Beard, Colin &al: "2-Phenylcyclobutylamine". The Journal of Organic Chemistry. vol. 26. No. 7. Jul. 1, 1961 (Jul. 1, 1961). pp. 2335-2339. XP055136566. ISSN: 0022-3263. DOI: 10.1021jjo01351a045.

Komiskey, H. L. et al.: "Inhibition of synaptosomal uptake of norepinephrine and dopamine by conformationlly restricted sympathomimetic amines" in: European Journal of Pharmacology, vol. 52, No. 1, pp. 37-45.

4-MEMBERED RING CARBOXAMIDES USED AS NEMATICIDES

RELATED APPLICATION INFORMATION

This application is a 371 of International Application No. PCT/EP2014/063895, filed Jul. 1, 2014, which claims priority to European Patent Application No. 13175632.2, filed Jul. 8, 2013 and European Patent Application No. 13175940.9 filed Jul. 10, 2013, the contents of all of which are incorporated herein by reference herein.

The present invention relates to novel 4-membered ring carboxamide compounds, a process for the preparation of these compounds and their use as nematicides.

Cyclobutylcarboxamides are described, for example, in WO09/043784, WO06/122952, WO06/122955, WO05/103006, WO05/103004 and WO04/014842.

Novel four membered ring carboxamides have now been found characterized by a cis substituted four membered ring comprising specific absolute stereochemistry at each of two positions, which show good nematicidal activity.

The present invention thus relates to compounds of the formula (I)

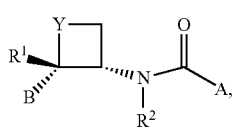

wherein

Y represents O or CH2;

A represents phenyl or a 5- or 6-membered heterocyclic ring containing 1 to 3 heteroatoms independently selected from oxygen, nitrogen and sulphur, wherein the phenyl is optionally substituted by one or more R3 and the heteroaromatic ring is optionally substituted by one or more R4;

B represents phenyl optionally substituted by one or more R5;

R1 represents hydrogen, hydroxy, C1-C4 alkoxy, C1-C4 haloalkoxy; C1-C4 alkyl, cyano, C1-C4 haloalkyl or halogen;

R2 represents hydrogen, C1-C4-alkyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl;

each R3 independently of one another represents halogen, cyano, C1-C4-alkyl, C1-C4-haloalkyl, C1-C4-alkoxy, C1-C4-haloalkoxy or C1-C4-haloalkylthio;

each R4 independently of one another represents halogen, cyano, C1-C4-alkyl, C1-C4-haloalkyl, C1-C4-alkoxy, C1-C4-haloalkoxy or C1-C4-haloalkylthio;

each R5 independently of one another represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C2-C6-haloalkenyl, C2-C6 haloalkynyl, 5- or 6-membered heterocycle optionally substituted by one or more substituents R6 or C3-C6-cycloalkyl optionally substituted by one or more substituents R6;

each R6 independently of one another represents halogen, cyano, C1-C4-alkyl, C1-C4-haloalkyl or C1-C4-alkoxycarbonyl;

and tautomers/isomers/enantiomers/salts and N-oxides of these compounds.

In the substituent definitions of the compounds of the formula I, each alkyl moiety either alone or as part of a larger group (such as alkoxy, alkylthio, alkoxycarbonyl and alkylcarbonyl) is a straight or branched chain and is, for example, methyl, ethyl, n-propyl, n-butyl, isopropyl, sec-butyl, isobutyl, tert-butyl, pentyl, iso-pentyl or n-hexyl. The alkyl groups are suitably C1-C4-alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. Preferably, the alkenyl and alkynyl moieties contain 2 to 6, more preferably 3 or 4 carbon atoms.

Halogen is fluorine, chlorine, bromine or iodine, preferably fluorine, chlorine or bromine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

Cycloalkyl includes preferably cyclopropyl, cyclobutyl, cyclopentyl and cyclohexyl.

The terms "heterocycle" and "heterocyclic ring" are used interchangeably and are defined to include heterocycloalkyl, heterocycloalkenyl and heteroaryl groups. The heterocyclic rings represent preferably pyridyl, pyrimidyl, pyrazinyl, pyrazolyl, thienyl, furyl, (2,3)-dihydrofuryl, pyridazinyl, oxazolyl, isoxazolyl, thiazolyl, isothiazolyl, pyrrolyl, thiadiazolyl e.g. (1,2,3)-thiadiazolyl, imidazolyl, triazolyl, e.g. (1,2,4)-triazolyl, oxadiazolyl e.g. (1,3,4)-oxadiazolyl, 2,3-dihydro-1,4-oxathiinyl, 3,4-dihydro-2H-pyranyl, 4-oxo-2,3-dihydro-1,4-oxathiinyl, 4,4-dioxo-2,3-dihydro-1,4-oxathiinyl, 3,4-dihydro-2H-thiopyranyl, 2,3-dihydro-1,4-dioxinyl, morpholinyl, pyrrolidinyl, piperidinyl, piperazinyl, more preferably pyridyl, pyrimidyl, pyrazinyl, pyrazolyl, thienyl, furyl, pyridazinyl, oxazolyl, isoxazolyl, thiazolyl, isothiazolyl, pyrrolyl, thiadiazolyl e.g. (1,2,3)-thiadiazolyl, 2,3-dihydro-1,4-oxathiinyl. No heterocycle contains adjacent oxygen atoms, adjacent sulphur atoms, or adjacent oxygen and sulphur atoms.

A potential side product in the synthesis of the compounds of the formula I is the enantiomer of the compound of formula (I), i.e. compounds of formula (Iaa). The difference between the compounds of formula (I) and the compounds of formula (Iaa) is that the two carbon atoms bearing the B and the A-CO—NR2 groups each have their absolute stereochemistry formally inverted.

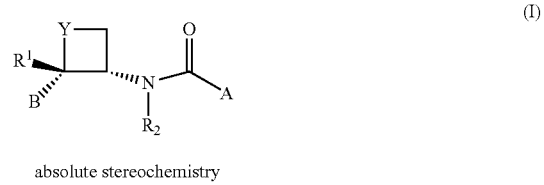

absolute stereochemistry

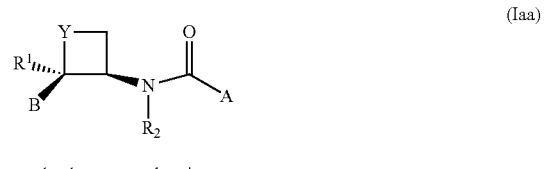

absolute stereochemistry

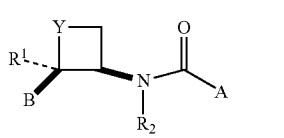

relative stereochemistry

The racemic compound (II) is a 1:1 mixture of the compounds of formula (I) and (Iaa). In the compounds of formula (I), (Iaa) and (II) the groups B and the A-CO—NR2 are cis to each other on the four-membered ring. Wedged bonds shown for example in the compounds of formula (I) and (Iaa) represent absolute stereochemistry, whereas thick straight bonds such as those shown for the compounds of formula (II) represent relative stereochemistry in racemic compounds. This applies throughout.

The compound of formula (XXXIII) below is the trans isomer of compound of formula (II), wherein B and A-CO—NR2 are trans to each other on the four-membered ring. This can also be formed as side products in the synthesis of compounds of the formula (II).

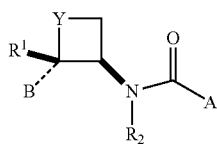

The compound of formula (XXXIII) also displays some pesticidal activity, in particular nematicidal and fungicidal activity.

According to the invention, in compositions comprising both the compound of formula (I) and the compound of formula (Iaa), the ratio of the compound of formula (I) to its enantiomer (the compound of formula (Iaa)) must be greater than 1:1. Preferably, the ratio of the compound of formula (I) to the compound of formula (Iaa) is greater than 1.5:1, more preferably greater than 2.5:1, especially greater than 4:1, advantageously greater than 9:1, desirably greater than 20:1, in particular greater than 35:1. This also applies to each relevant intermediate described herein therefor and the relevant enantiomer.

Mixtures containing up to 50%, preferably up to 40%, more preferably up to 30%, especially up to 20%, advantageously up to 10%, desirably up to 5%, in particular up to 3%, of the trans isomer are understood to be also part of this invention, such as any one of compounds of formula (I) and each relevant intermediate described herein therefor.

Preferably, the ratio of the compound of formula (I) to its trans isomer is greater than 1.5:1, more preferably greater than 2.5:1, especially greater than 4:1, advantageously greater than 9:1, desirably greater than 20:1, in particular greater than 35:1.

Preferably, in a composition comprising the compound of formula (I), its trans isomer (i.e. wherein the B and the A-CO—NR2 groups are trans to each other) and the compound of formula (Iaa), the composition comprises the compound of formula (I) in a concentration of at least 50%, more preferably 70%, even more preferably 85%, in particular over 92%, and particularly preferably over 97%, each based on the total amount of compound of formula (I), its trans isomer and the compound of formula (Iaa). It is particularly preferred that the mixture is at least 99% of the compound of formula (I) based on the total amount of compound of formula (I), its trans isomer and the compound of formula (Iaa).

It is possible that compounds of the formula (I) have further stereochemical centres in one of the substituents. Further isomers are then possible. The invention covers all such isomers and mixtures thereof.

The compounds of the formula (I) may occur in different tautomeric forms. The invention covers all those tautomeric forms and mixtures thereof.

The following list provides definitions, including preferred definitions, for substituents Y, A, B, R1, R2, R3, R4, R5, R6, R10, R11 and R12 with reference to compounds of formula (I). For any one of these substituents, any of the definitions given below may be combined with any definition of any other substituent given below or elsewhere in this document.

Y represents O or CH2.

Preferably, Y represents CH2.

A represents phenyl or a 5- or 6-membered heterocyclic ring containing 1 to 3 heteroatoms independently selected from oxygen, nitrogen and sulphur, wherein the phenyl is optionally substituted by one or more R3 and the heteroaromatic ring is optionally substituted by one or more R4. Preferably, A represents pyridyl, pyrimidyl, pyrazinyl, pyrazolyl, thienyl, furyl, (2,3)-dihydrofuryl, pyridazinyl, oxazolyl, isoxazolyl, thiazolyl, isothiazolyl, pyrrolyl, thiadiazolyl, imidazolyl, triazolyl, oxadiazolyl, 2,3-dihydro-1,4-oxathiinyl, 3,4-dihydro-2H-pyranyl, 4-oxo-2,3-dihydro-1,4-oxathiinyl, 4,4-dioxo-2,3-dihydro-1,4-oxathiinyl, 3,4-dihydro-2H-thiopyranyl, 2,3-dihydro-1,4-dioxinyl, morpholinyl, pyrrolidinyl, piperidinyl, piperazinyl, wherein the phenyl is optionally substituted by one or more R3 and each heteroaromatic ring is optionally substituted by one or more R4.

More preferably, A represents phenyl, pyridyl, pyrimidyl, pyrazinyl, pyrazolyl, thienyl, furyl, pyridazinyl, oxazolyl, isoxazolyl, thiazolyl, isothiazolyl, pyrrolyl, thiadiazolyl, 2,3-dihydro-1,4-oxathiinyl, wherein the phenyl is optionally substituted by one or more R3 and each heteroaromatic ring is optionally substituted by one or more R4.

Even more preferably, A represents phenyl, pyridyl, pyrimidyl, pyrazinyl, pyrazolyl, thienyl or furyl, wherein the phenyl is optionally substituted by one or more R3 and each heteroaromatic ring is optionally substituted by one or more R4.

More preferably again, A represents phenyl, pyridyl, pyrimidyl, pyrazinyl, pyrazolyl or furyl, wherein the phenyl is optionally substituted by one or more R3 and each heteroaromatic ring is optionally substituted by one or more R4.

Even more preferably again, A represents phenyl, pyridyl, pyrazinyl or pyrazolyl wherein the phenyl is optionally substituted by one or more R3 and each heteroaromatic ring is optionally substituted by one or more R4.

Yet more preferably, A represents phenyl, pyrazinyl, pyridyl, or furyl wherein the phenyl is optionally substituted by one R3 and the heteroaromatic rings are optionally substituted by one R4.

Most preferably, A represents phenyl, 2-pyrazinyl, 2-pyridyl or 3-pyridyl wherein the phenyl is optionally substituted by one R3 and the pyrazinyl and pyridyl are optionally substituted by one R4.

Preferably, in the embodiments described above, A represents 2-pyridyl, 3-pyridyl, 2-pyrimidyl, 4-pyrimidyl, 2-pyrazinyl, 4-pyrazolyl, 2-thienyl, 3-thienyl, 2-furyl, 3-furyl, (1,2,3) thiadiazolyl, (1,2,4)-triazolyl or (1,3,4)-oxadiazolyl as may be appropriate.

In an instance, there are 1 to 3 substituents R3 or R4 on A. Preferably, A is substituted by one or two of such substituents, most preferably, A is substituted by one substitutent R3 or R4. The preferable point or points of attachment of these substituents is ortho to the point of attachment of A to C(O)NR2.

In one group of compounds, A represents phenyl or a 5- or 6-membered heteroaromatic ring containing 1 to 2 heteroatoms independently selected from oxygen, nitrogen and sulphur, wherein the phenyl is optionally substituted by one or more R3 and the heteroaromatic ring is optionally substituted by one or more R4.

Preferably in this group of compounds, A represents phenyl, pyridyl, pyrimidyl, pyrazinyl, pyrazolyl, thienyl or furyl, wherein the phenyl is optionally substituted by one or more R3 and each heteroaromatic ring is optionally substituted by one or more R4.

More preferably in this group of compounds, A represents phenyl, pyridyl, pyrazinyl or pyrazolyl wherein the phenyl is optionally substituted by one or more R3 and each heteroaromatic ring is optionally substituted by one or more R4.

Most preferably in this group of compounds, A represents phenyl, 2-pyrazinyl, 2-pyridyl or 3-pyridyl wherein the phenyl is optionally substituted by one R3 and the pyrazinyl and pyridyl are optionally substituted by one R4.

Preferably, in the embodiments described above, A represents 2-pyridyl, 3-pyridyl, 2-pyrimidyl, 4-pyrimidyl, 2-pyrazinyl, 4-pyrazolyl, 2-thienyl, 3-thienyl, 2-furyl or 3-furyl, as may be appropriate.

In an instance, there are 1 to 3 substituents R3 or R4 on A. Preferably, A is substituted by one or two of such substituents, most preferably, A is substituted by one substitutent R3 or R4. The preferable point or points of attachment of these substituents is ortho to the point of attachment of A to C(O)NR2.

B represents phenyl optionally substituted by one or more R5;

Preferably B is substituted by 1 to 3 substituents R5, more preferably 1 or 2 substituents R5. The preferable point or points of attachment of these substituents is para and/or ortho to the point of attachment of B to the four-membered ring.

Most preferably, B represents R8 or R9.

R1 represents hydrogen, hydroxy, C1-C4 alkoxy, C1-C4 haloalkoxy; C1-C4 alkyl, cyano, C1-C4 haloalkyl or halogen.

R2 represents hydrogen, C1-C4-alkyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl.

Preferably, R1 and R2 are both hydrogen

Each R3 independently of one another represents halogen, cyano, C1-C4-alkyl, C1-C4-haloalkyl, C1-C4-alkoxy, C1-C4-haloalkoxy or C1-C4-haloalkylthio.

Preferably, each R3 independently of one another represents halogen, methyl, difluoromethyl or trifluoromethyl.

More preferably, each R3 independently of one another represents halogen or trifluoromethyl.

Even more preferably, each R3 independently of one another represents halogen.

In another group of compounds, each R3 is most preferably trifluoromethyl.

each R4 independently of one another represents halogen, cyano, C1-C4-alkyl, C1-C4-haloalkyl, C1-C4-alkoxy, C1-C4-haloalkoxy or C1-C4-haloalkylthio.

Preferably, each R4 independently of one another represents halogen, C1-C4-alkyl or C1-C4-haloalkyl.

More preferably, each R4 independently of one another represents halogen, C1-C2-alkyl or C1-C2-haloalkyl.

Even more preferably, each R4 independently of one another represents chloro, bromo, methyl, difluoromethyl or trifluoromethyl.

Even more preferably, each R4 independently of one another represents chloro, bromo, methyl or trifluoromethyl.

Most preferably, each R4 independently of one another represents chloro or trifluoromethyl.

Each R5 independently of one another represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C2-C6-haloalkenyl, C2-C6 haloalkynyl, 5- or 6-membered heterocycle optionally substituted by one or more substituents R6 or C3-C6-cycloalkyl optionally substituted by one or more substituents R6.

Preferably, each R5 independently of one another represents halogen, cyano, C1-C4-haloalkyl, C1-C4-haloalkoxy, C3-C6-cycloalkyl optionally substituted by one or more substituents R6, 5- or 6-membered heterocycle optionally substituted by one or more substituents R6 or C2-C6-haloalkenyl.

More preferably, each R5 independently of one another represents halogen, cyano, C1-C4-haloalkyl, C1-C4-haloalkoxy, 5- or 6-membered heterocycle optionally substituted by one or more substituents R6 or C3-C6-cycloalkyl optionally substituted by one or more substituents R6.

Even more preferably, each R5 independently of one another represents halogen, cyano, C1-C4-haloalkyl, C1-C4-haloalkoxy, pyridyl optionally substituted by one or more substituents R6, pyrazole optionally substituted by one or more substituents R6 or C3-C6-cycloalkyl optionally substituted by one or more substituents R6.

More preferably again, each R5 independently of one another represents halogen, cyano, C1-C4-haloalkyl, C1-C4-haloalkoxy, pyrazole optionally substituted by one or more substituents R6 or C3-C6-cycloalkyl optionally substituted by one or more substituents R6. Even more preferably, each R5 independently of one another represents halogen or trifluoromethyl.

Most preferably, each R5 independently of one another represents halogen.

Each R6 independently of one another represents halogen, cyano, C1-C4-alkyl, C1-C4-haloalkyl or C1-C4-alkoxycarbonyl.

Preferably, each R6 independently of one another represents halogen, C1-C4-alkyl or C1-C4-haloalkyl.

More preferably, each R6 independently of one another represents halogen or trifluoromethyl.

R8 represents

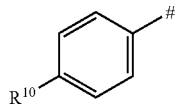

R9 represents

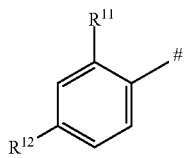

R10 represents fluoro, chloro, bromo, difluoromethyl, trifluoromethyl, difluoromethoxy or trifluoromethoxy.
Preferably, R10 represents chloro.
R11 represents fluoro, chloro or bromo.
Preferably, R11 represents fluoro or chloro.
R12 represents fluoro, chloro, bromo or trifluoromethyl.
Preferably, R12 represents fluoro, chloro or trifluoromethyl.
More preferably R12 represents fluoro or chloro.
In one group of compounds, R12 represents chloro or trifluoromethyl
In one group of compounds, Y represents O or CH2;
A represents phenyl or a 5- or 6-membered heteroaromatic ring containing 1 to 2 heteroatoms independently selected from oxygen, nitrogen and sulphur, wherein the phenyl is optionally substituted by one or more R3 and the heteroaromatic ring is optionally substituted by one or more R4;
B represents phenyl optionally substituted by one or more R5;
R1 represents hydrogen, hydroxy, C1-C4 alkoxy, C1-C4 haloalkoxy; C1-C4 alkyl, cyano, C1-C4 haloalkyl or halogen;
R2 represents hydrogen, C1-C4-alkyl, C1-C4-alkoxycarbonyl, C2-C4-alkenyl, C2-C4-alkynyl, C1-C4-cyanoalkyl, C3-C6-cycloalkylcarbonyl, C3-C6-cycloalkoxycarbonyl or benzyl;
   each R3 independently of one another represents halogen, cyano, C1-C4-alkyl, C1-C4-haloalkyl, C1-C4-alkoxy, C1-C4-haloalkoxy or C1-C4-haloalkylthio;
   each R4 independently of one another represents halogen, cyano, C1-C4-alkyl, C1-C4-haloalkyl, C1-C4-alkoxy, C1-C4-haloalkoxy or C1-C4-haloalkylthio;
   each R5 independently of one another represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C2-C6-haloalkenyl, C2-C6 haloalkynyl, 5- or 6-membered heterocycle optionally substituted by one or more substituents R6 or C3-C6-cycloalkyl optionally substituted by one or more substituents R6;
   each R6 independently of one another represents halogen, cyano, C1-C4-alkyl, C1-C4-haloalkyl or C1-C4-alkoxycarbonyl.
In one group of compounds, R1 and R2 are each hydrogen.
In another group of compounds,
Y represents O or CH2;
A represents phenyl, pyridyl, pyrimidyl, pyrazinyl, pyrazolyl, thienyl or furyl, wherein the phenyl is optionally substituted by one or more R3 and each heteroaromatic ring is optionally substituted by one or more R4;
B represents phenyl optionally substituted by one or more R5;
R1 represents hydrogen;
R2 represents hydrogen;
   each R3 independently of one another represents halogen, cyano, C1-C4-alkyl, C1-C4-haloalkyl, C1-C4-alkoxy, C1-C4-haloalkoxy or C1-C4-haloalkylthio;
   each R4 independently of one another represents halogen, C1-C4-alkyl or C1-C4-haloalkyl;
   each R5 independently of one another represents halogen, cyano, C1-C4-haloalkyl, C1-C4-haloalkoxy, C2-C6-haloalkenyl, 5- or 6-membered heterocycle or C3-C6-cycloalkyl wherein the heterocycle and the cycloalkyl are each optionally substituted by one or more substituents R6;
   each R6 independently of one another represents halogen, C1-C4-alkyl or C1-C4-haloalkyl.
Preferably in this group of compounds, A represents phenyl, 2-pyridyl, 3-pyridyl, 2-pyrimidyl, 2-pyrazinyl, 2-thienyl, 3-thienyl, 2-furyl or 3-furyl, wherein the phenyl is optionally substituted by one or more R3 and each heteroaromatic ring is optionally substituted by one or more R4.
In another group of compounds, Y represents O or CH2;
A represents phenyl, pyridyl, pyrimidyl, pyrazinyl, pyrazolyl, thienyl or furyl, wherein the phenyl is optionally substituted by one or more R3 and each heteroaromatic ring is optionally substituted by one or more R4;
B represents phenyl optionally substituted by one or more R5;
R1 represents hydrogen;
R2 represents hydrogen;
   each R3 independently of one another represents halogen, cyano, C1-C4-alkyl, C1-C4-haloalkyl, C1-C4-alkoxy, C1-C4-haloalkoxy or C1-C4-haloalkylthio;
   each R4 independently of one another represents halogen, C1-C4-alkyl or C1-C4-haloalkyl;
   each R5 independently of one another represents halogen, cyano, C1-C4-haloalkyl, C1-C4-haloalkoxy, 5- or 6-membered heterocycle or C3-C6-cycloalkyl, wherein the heterocycle and the cycloalkyl are each optionally substituted by one or more substituents R6;
   each R6 independently of one another represents halogen, C1-C4-alkyl or C1-C4-haloalkyl.
Preferably in this group of compounds, A represents phenyl, 2-pyridyl, 3-pyridyl, 2-pyrimidyl, 4-pyrimidyl, 2-pyrazinyl, 2-thienyl, 3-thienyl, 4-pyrazolyl, 2-furyl or 3-furyl, wherein the phenyl is optionally substituted by one to three R3 and each heteroaromatic ring is optionally substituted by one to three R4;
B represents phenyl optionally substituted by one to three R5.
In another group of compounds,
Y represents O or CH2;
A represents phenyl, pyridyl, pyrimidyl, pyrazinyl, pyrazolyl, thienyl or furyl, wherein the phenyl is optionally substituted by one or more R3 and each heteroaromatic ring is optionally substituted by one or more R4;
B represents phenyl optionally substituted by one or more R5;
R1 represents hydrogen;
R2 represents hydrogen;
   each R3 independently of one another represents halogen, cyano, C1-C4-alkyl, C1-C4-haloalkyl, C1-C4-alkoxy, C1-C4-haloalkoxy or C1-C4-haloalkylthio;
   each R4 independently of one another represents halogen, C1-C4-alkyl or C1-C4-haloalkyl;
   each R5 independently of one another represents halogen, cyano, C1-C4-haloalkyl, C1-C4-haloalkoxy or C3-C6-cycloalkyl optionally substituted by one or more substituents R6;
   each R6 independently of one another represents halogen, C1-C4-alkyl or C1-C4-haloalkyl.

Preferably in this group of compounds, A represents phenyl, 2-pyridyl, 3-pyridyl, 2-pyrimidyl, 2-pyrazinyl, 2-thienyl, 3-thienyl, 2-furyl or 3-furyl, wherein the phenyl is optionally substituted by one or more R3 and each heteroaromatic ring is optionally substituted by one or more R4.

In another group of compounds, Y represents CH2;

A represents phenyl, pyridyl, pyrazinyl, furyl or pyrazolyl wherein the phenyl is optionally substituted by one or more R3 and each heteroaromatic ring is optionally substituted by one or more R4;

B represents phenyl optionally substituted by one or more R5;

R1 represents hydrogen;

R2 represents hydrogen;

each R3 independently of one another represents halogen or trifluoromethyl;

each R4 independently of one another represents halogen, C1-C4-alkyl or C1-C4-haloalkyl;

each R5 independently of one another represents halogen or trifluoromethyl.

Preferably in this group of compounds, A represents phenyl, 2-pyridyl, 3-pyridyl, 2-pyrazinyl, 2-furyl, 3-furyl or 4-pyrazolyl, wherein the phenyl is optionally substituted by one or two R3 and each heteroaromatic ring is optionally substituted by one to three R4;

B represents phenyl optionally substituted by one or two R5.

More preferably in this group of compounds, A represents phenyl, 2-pyridyl, 3-pyridyl, 2-pyrazinyl or 4-pyrazolyl, wherein the phenyl is optionally substituted by one or two R3 and each heteroaromatic ring is optionally substituted by one to three R4;

B represents phenyl optionally substituted by one or two R5.

In another group of compounds, Y represents CH2;

A represents phenyl, pyridyl, pyrazinyl, furyl or pyrazolyl wherein the phenyl is optionally substituted by one or more R3 and each heteroaromatic ring is optionally substituted by one or more R4;

B represents phenyl optionally substituted by one or more R5;

R1 represents hydrogen;

R2 represents hydrogen;

each R3 independently of one another represents halogen or C1-C4-haloalkyl;

each R4 independently of one another represents halogen, C1-C4-alkyl or C1-C4-haloalkyl;

each R5 independently of one another represents halogen.

Preferably in this group of compounds, A represents phenyl, 2-pyridyl, 3-pyridyl, 2-pyrazinyl, 2-furyl, 3-furyl or 4-pyrazolyl, wherein the phenyl is optionally substituted by one or two R3 and each heteroaromatic ring is optionally substituted by one to three R4;

B represents phenyl optionally substituted by one or two R5.

More preferably in this group of compounds, A represents phenyl, 2-pyridyl, 3-pyridyl, 2-pyrazinyl or 4-pyrazolyl, wherein the phenyl is optionally substituted by one or two R3 and each heteroaromatic ring is optionally substituted by one to three R4;

B represents phenyl optionally substituted by one or two R5.

In another group of compounds

Y represents CH2;

A represents phenyl, 2-pyridyl, 3-pyridyl, 2-pyrazinyl, 2-furyl, 3-furyl or 4-pyrazolyl wherein the phenyl is optionally substituted by one or more R3 and each heteroaromatic ring is optionally substituted by one to three R4;

B represents phenyl optionally substituted by one or two R5;

R1 represents hydrogen;

R2 represents hydrogen;

each R3 independently of one another represents halogen or trifluoromethyl;

each R4 independently of one another represents halogen, C1-C2-alkyl or C1-C2-haloalkyl;

each R5 independently of one another represents halogen or trifluoromethyl.

Preferably in this group of compounds,

Y represents CH2;

A represents phenyl, 2-pyridyl, 3-pyridyl, 2-pyrazinyl, 2-furyl, 3-furyl or 4-pyrazolyl wherein the phenyl is optionally substituted by one R3 and each heteroaromatic ring is optionally substituted by one to three R4;

B represents phenyl optionally substituted by one or two R5;

R1 represents hydrogen;

R2 represents hydrogen;

each R3 independently of one another represents halogen or trifluoromethyl;

each R4 independently of one another represents halogen, methyl, difluoromethyl or trifluoromethyl;

each R5 independently of one another represents halogen or trifluoromethyl.

More preferably in this group of compounds,

Y represents CH2;

A represents phenyl, 2-pyridyl, 3-pyridyl, 2-pyrazinyl or 4-pyrazolyl wherein the phenyl is optionally substituted by one R3 and each heteroaromatic ring is optionally substituted by one to three R4;

B represents phenyl optionally substituted by one or two R5;

R1 represents hydrogen;

R2 represents hydrogen;

each R3 independently of one another represents halogen or trifluoromethyl;

each R4 independently of one another represents halogen, methyl or trifluoromethyl;

each R5 independently of one another represents halogen or trifluoromethyl.

In another group of compounds

Y represents CH2;

A represents phenyl, 2-pyridyl, 3-pyridyl, 2-pyrazinyl, 2-furyl, 3-furyl or 4-pyrazolyl wherein the phenyl is optionally substituted by one or more R3 and each heteroaromatic ring is optionally substituted by one to three R4;

B represents phenyl optionally substituted by one or two R5;

R1 represents hydrogen;

R2 represents hydrogen;

each R3 independently of one another represents halogen or C1-C2-haloalkyl;

each R4 independently of one another represents halogen, C1-C2-alkyl or C1-C2-haloalkyl;

each R5 independently of one another represents halogen.

Preferably in this group of compounds,

Y represents CH2;

A represents phenyl, 2-pyridyl, 3-pyridyl, 2-pyrazinyl, 2-furyl, 3-furyl or 4-pyrazolyl wherein the phenyl is optionally substituted by one R3 and each heteroaromatic ring is optionally substituted by one to three R4;

B represents phenyl optionally substituted by one or two R5;

R1 represents hydrogen;
R2 represents hydrogen;
each R3 independently of one another represents halogen or trifluoromethyl;
each R4 independently of one another represents halogen, methyl, difluoromethyl or trifluoromethyl;
each R5 independently of one another represents halogen.

In another group of compounds
Y represents CH2;
A represents phenyl, 2-pyridyl, 3-pyridyl, 2-pyrazinyl or 4-pyrazolyl wherein the phenyl is optionally substituted by one or more R3 and each heteroaromatic ring is optionally substituted by one to three R4;
B represents phenyl optionally substituted by one or two R5;
R1 represents hydrogen;
R2 represents hydrogen;
each R3 independently of one another represents halogen;
each R4 independently of one another represents halogen, C1-C2-alkyl or C1-C2-haloalkyl;
each R5 independently of one another represents halogen.

Preferably in this group of compounds,
Y represents CH2;
A represents phenyl, 2-pyridyl, 3-pyridyl, 2-pyrazinyl or 4-pyrazolyl wherein the phenyl is optionally substituted by one R3 and each heteroaromatic ring is optionally substituted by one to three R4;
B represents phenyl optionally substituted by one or two R5;
R1 represents hydrogen;
R2 represents hydrogen;
each R3 independently of one another represents halogen;
each R4 independently of one another represents halogen, methyl or trifluoromethyl;
each R5 independently of one another represents halogen.

In another group of compounds, Y represents CH2;
A represents phenyl, 2-pyrazinyl, 2-pyridyl, 3-pyridyl, 2-furyl, or 3-furyl wherein the phenyl is optionally substituted by one R3 and the heteroaromatic rings are optionally substituted by one R4;
B represents R8 or R9;
R1 represents hydrogen;
R2 represents hydrogen;
R3 represents halogen, methyl, difluoromethyl or trifluoromethyl;
R4 represents chloro, bromo, methyl, difluoromethyl or trifluoromethyl;
R8 represents

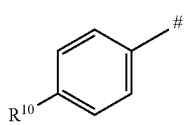

R9 represents

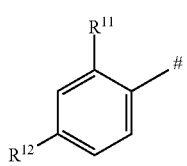

R10 represents fluoro, chloro, bromo, difluoromethyl, trifluoromethyl, difluoromethoxy or trifluoromethoxy;
R11 represents fluoro, chloro or bromo;
R12 represents fluoro, chloro, bromo or trifluoromethyl.

Preferably in this group of compounds, Y represents CH2;
A represents phenyl, 2-pyrazinyl, 2-pyridyl or 3-pyridyl wherein the phenyl is optionally substituted by one R3 and the pyrazinyl and pyridyl are optionally substituted by one R4;
B represents R8 or R9;
R1 represents hydrogen;
R2 represents hydrogen;
R3 represents halogen, methyl, difluoromethyl or trifluoromethyl;
R4 represents chloro, bromo, methyl or trifluoromethyl;
R8 represents

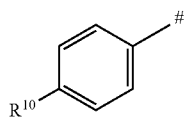

R9 represents

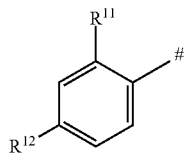

R10 represents fluoro, chloro, bromo, difluoromethyl, trifluoromethyl, difluoromethoxy or trifluoromethoxy;
R11 represents fluoro, chloro or bromo;
R12 represents fluoro, chloro, bromo or trifluoromethyl.

In another group of compounds, Y represents CH2;
A represents phenyl, 2-pyrazinyl, 2-pyridyl, 3-pyridyl, 2-furyl, or 3-furyl wherein the phenyl is optionally substituted by one R3 and the heteroaromatic rings are optionally substituted by one R4;
B represents R8 or R9;
R1 represents hydrogen;
R2 represents hydrogen;
R3 represents trifluoromethyl;
R4 represents chloro, difluoromethyl or trifluoromethyl;
R8 represents

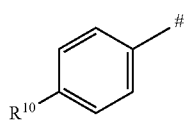

R9 represents

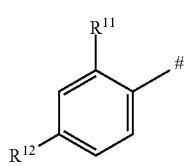

R10 represents chloro;
R11 represents fluoro or chloro;
R12 represents chloro, fluoro or trifluoromethyl.
Preferably in this group of compounds, Y represents CH2;
A represents phenyl, 2-pyrazinyl, 2-pyridyl or 3-pyridyl wherein the phenyl is optionally substituted by one R3 and the pyrazinyl and pyridyl are optionally substituted by one R4;
B represents R8 or R9;
R1 represents hydrogen;
R2 represents hydrogen;
R3 represents trifluoromethyl;
R4 represents chloro or trifluoromethyl;
R8 represents

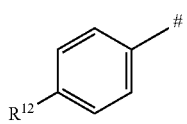

R9 represents

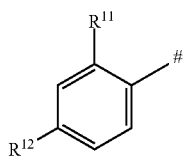

R10 represents chloro;
R11 represents fluoro or chloro;
R12 represents chloro or trifluoromethyl.

More preferably in this group of compounds, A represents phenyl, 2-pyrazinyl, 2-pyridyl or 3-pyridyl wherein the phenyl is optionally substituted by one R3 and the 2-pyrazinyl and 3-pyridyl are optionally substituted by one R4 and wherein the 2-pyridyl is substituted by trifluoromethyl.

In another group of compounds, each R5 independently of one another represents halogen, cyano, C1-C4-alkyl, C1-C4-haloalkyl, C1-C4-alkoxy, C1-C4-haloalkoxy, C1-C4-alkylsulfanyl, C1-C4-haloalkylsulfanyl, C1-C4-alkylsulfinyl, C1-C4-haloalkylsulfinyl, C1-C4-alkylsulfonyl, C1-C4-haloalkylsulfonyl, C2-C6-haloalkenyl, C2-C6 haloalkynyl or C3-C6-cycloalkyl optionally substituted by one or more substituents R6.

Preferably in this group of compounds, each R5 independently of one another represents halogen, cyano, C1-C4-haloalkyl, C1-C4-haloalkoxy, C3-C6-cycloalkyl optionally substituted by one or more substituents R6 or C2-C6-haloalkenyl.

More preferably in this group of compounds, each R5 independently of one another represents halogen, cyano, C1-C4-haloalkyl, C1-C4-haloalkoxy or C3-C6-cycloalkyl optionally substituted by one or more substituents R6.

Even more preferably in this group of compounds, each R5 independently of one another represents halogen or trifluoromethyl.

Most preferably in this group of compounds, each R5 independently of one another represents halogen.

Certain intermediates that can be used to prepare compounds of formula (I) are novel and as such also form part of the invention.

Accordingly, in a further aspect, the invention provides certain compounds of formula (II)

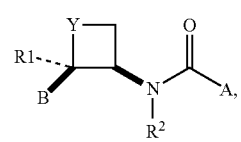

wherein Y, A, B, R1 and R2 are as defined herein for a compound of formula (I). The preferred definitions of Y, A, B, R1 and R2 defined in respect of compounds of formula (I) also apply to compounds of formula (II)

It should be noted that the compound of formula (II) is a racemic mixture wherein the substituents B and N(R2)COA are cis to each other. The compounds of formula (II) are also known to have pesticidal activity, in particular nematicidal and fungicidal activity, more particularly nematicidal activity.

Accordingly, the present invention also makes available nematicidal and fungicidal compositions comprising compounds of formula (II), in particular nematicidal compositions comprising compounds of formula (II), In a further aspect, the invention provides the racemic compounds of formula (XII)

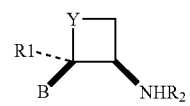

wherein Y, B, R1 and R2 are as defined herein for a compound of formula (I) provided the B and NHR2 are cis to each other on the four-membered ring; or a salt or N-oxide thereof, wherein the compounds of the formula

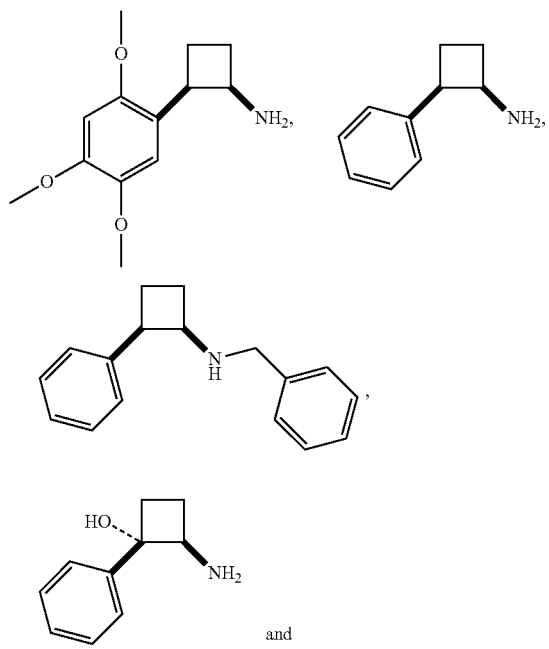

and

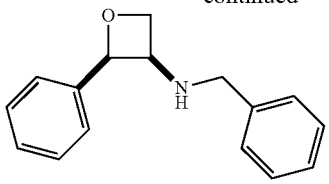

are excluded.

The preferred definitions of Y, B, R1 and R2 defined in respect of compounds of formula (I) also apply to compounds of formula (XII).

In a more preferred embodiment of the compounds of formula (XII), Y is CH2, R1 and R2 are each hydrogen and B is phenyl, substituted by 1 to 3 substituents, independently selected from halogen, cyclopropyl, C1-C4-haloalkylcyclopropyl, C1-C4-haloalkyl and C1-C4-haloalkoxy.

In an even more preferred embodiment of the compounds of formula (XII), Y is CH2, R1 and R2 are each hydrogen and B is phenyl substituted by 1 to 3 substituents, independently selected from fluoro, chloro, trifluoromethyl, cyclopropyl, trifluoromethylcyclopropyl and trifluoromethoxy.

In a particularly preferred embodiment of the compounds of formula (XII), Y is CH2, R1 and R2 are each hydrogen and B is a phenyl substituted by one or two halogen atoms.

In a further aspect, the invention provides a compound of formula (XIII)

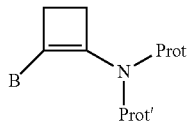
(XIII)

Wherein B is as defined as herein for a compound of formula (I), Prot is a protecting group and Prot' is hydrogen or a protecting group; or a salt or N-oxide thereof.

Examples of suitable protecting group for compounds of formula (XIII) are carbamates, amides, cyclic imides, sulfonamides, silyl groups and benzyl groups.

In the compounds of formula (XIII), Prot preferably represents carbamates of formula:

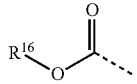

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl, 4-bromobenzyl;
or amides of formula:

wherein R17 represents hydrogen, C1-C4 alkyl, C1-C4 haloalkyl, C1-C4 alkoxylalkyl, C2-C4 alkenyl, benzyl, phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro;
or sulfonamides of formula:

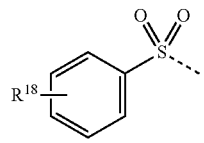

wherein the phenyl ring is optionally substituted by one or more R18 as defined previously;
or silyl groups of formula:

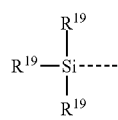

wherein R19 independently of one another represent C1-C4 alkyl, C1-C4 haloalkyl, C2-C4 alkenyl, benzyl, phenyl optionally substituted by one or more R18 as described previously;
or benzyl groups of formula:

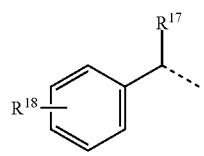

wherein the phenyl ring is optionally substituted by one or more R18 as defined previously;
wherein the benzylic position is substituted by R17 as described previously;
or Prot and Prot' together represent cyclic imides of formula:

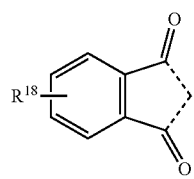

wherein the phenyl ring is optionally substituted by one or more R18 as defined previously.

More preferably for compounds of formula (XIII), Prot represents carbamates of formula:

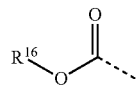

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl, 4-bromobenzyl;

or amides of formula:

wherein R17 represents hydrogen, C1-C4 alkyl, C1-C4 haloalkyl, C1-C4 alkoxylalkyl, C2-C4 alkenyl, benzyl, phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro.

When Prot' is a protecting group, the preferred definitions are as for Prot defined herein.

In one embodiment of the invention, Prot' is hydrogen.

Preferably in compounds of the formula (XIII), B represents phenyl substituted by 1 to 3 R5, wherein each R5 independently of one another represents halogen, cyclopropyl, C1-C4-haloalkylcyclopropyl, C1-C4-haloalkyl or C1-C4-haloalkoxy.

More preferably in the compounds of formula (XIII), B represents phenyl substituted by 1 to 3 R5, wherein each R5 independently of one another represents halogen, trifluoromethyl, cyclopropyl, trifluoromethylcyclopropyl or trifluoromethoxy.

Even more preferably in the compounds of formula (XIII), B is a phenyl substituted by one or two R5, wherein each R5 independently of one another represents chloro or fluoro.

In a further aspect, the invention provides a racemic compound of formula (XVII)

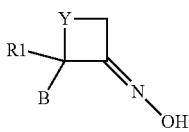
(XVII)

wherein Y, B and R1 are as defined herein for a compound of formula (I); or a salt or N-oxide thereof, provided that the compounds of the formula (XVII) are not

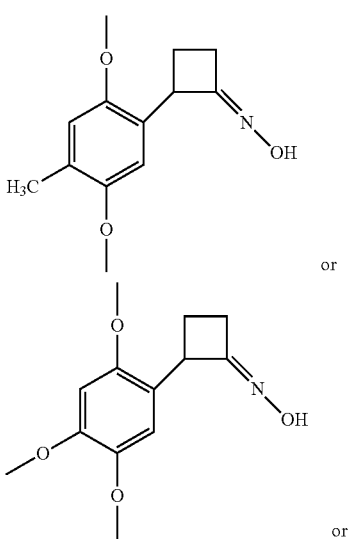

or

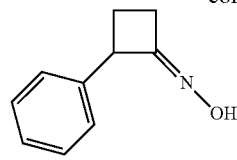

The preferred definitions of Y, B and R1 defined in respect of compounds of formula (I) also apply to compounds of formula (XVII)

In a more preferred embodiment of the compounds of formula (XVII), Y is CH2, R1 is hydrogen and B is phenyl, substituted by 1 to 3 substituents, independently selected from halogen, cyclopropyl, C1-C4-haloalkylcyclopropyl, C1-C4-haloalkyl and C1-C4-haloalkoxy.

In an even more preferred embodiment of the compounds of formula (XVII), Y is CH2, R1 is hydrogen and B is phenyl substituted by 1 to 3 substituents, independently selected from fluoro, chloro, trifluoromethyl, cyclopropyl, trifluoromethylcyclopropyl and trifluoromethoxy.

In a particularly preferred embodiment of the compounds of formula (XVII), Y is CH2, R1 is hydrogen and B is a phenyl substituted by 1 or 2 halogen.

In a further aspect, the invention provides a compound of formula (III)

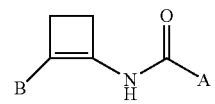
(III)

Wherein A and B are as defined herein for a compound of formula (I); or a salt or N-oxide thereof. The preferred definitions of A and B defined in respect of compounds of formula (I) also apply to compounds of formula (III).

In a further aspect, the invention provides a compound of formula (XIV)

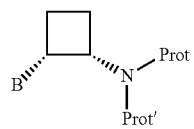
(XIV)

wherein B is as defined herein for a compound of formula (I), and Prot and Prot' are as defined herein for the compounds of formula (XIII); or a salt or N-oxide thereof. The preferred definitions of B defined in respect of compounds of formula (I) also apply to compounds of formula (XIV). The preferred definitions of Prot defined in respect of compounds of formula (XIII) also apply to compounds of formula (XIV).

In a further aspect, the invention provides a compound of formula (XVI)

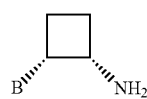
(XVI)

wherein B is as defined herein for a compound of formula (I); or a salt or N-oxide thereof. The preferred definitions of B defined in respect of compounds of formula (I) also apply to compounds of formula (XVI).

In a further aspect, the invention provides a compound of formula (XIX)

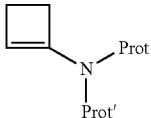

(XIX)

wherein Prot and Prot' are as defined herein for the compounds of formula (XIII); or a salt or N-oxide thereof. The preferred definitions of Prot and Prot' defined in respect of compounds of formula (XIII) also apply to compounds of formula (XIX).

In a further aspect, the invention provides a compound of formula (XVIII)

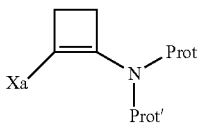

(XVIII)

Wherein Xa represents halogen and Prot and Prot' are as defined herein for the compounds of formula (XIII); or a salt or N-oxide thereof. The preferred definitions of Prot and Prot' defined in respect of compounds of formula (XIII) also apply to compounds of formula (XVIII).

In a further aspect, the invention provides a compound of formula (VII)

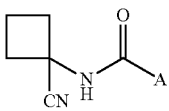

(VII)

wherein A is as defined herein for a compound of formula (I); or a salt or N-oxide thereof. The preferred definitions of A defined in respect of compounds of formula (I) also apply to compounds of formula (VII).

In a further aspect, the invention provides a compound of formula (VI)

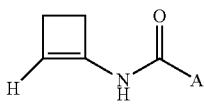

(VI)

wherein A is as defined herein for a compound of formula (I); or a salt or N-oxide thereof. The preferred definitions of A defined in respect of compounds of formula (I) also apply to compounds of formula (VI).

In a further aspect, the invention provides a compound of formula (V)

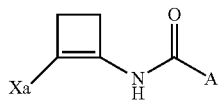

(V)

wherein A is as defined herein for a compound of formula (I) and Xa is halogen; or a salt or N-oxide thereof. The preferred definitions of A defined in respect of compounds of formula (I) also apply to compounds of formula (V).

In a further aspect, the invention provides a compound of formula (X)

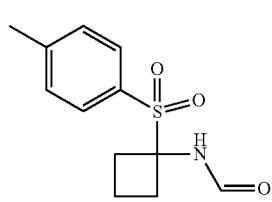

(X)

or a salt or N-oxide thereof.

In a further aspect, the invention provides a compound of formula (IX)

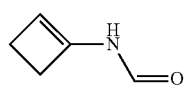

(IX)

or a salt or N-oxide thereof.

In a further aspect, the invention provides a compound of formula (VIII)

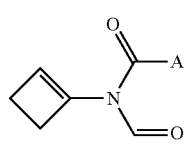

(VIII)

wherein A is as defined herein for a compound of formula (I), or a salt or N-oxide thereof. The preferred definitions of A defined in respect of compounds of formula (I) also apply to compounds of formula (VIII).

In a further aspect, the invention provides a compound of formula (XXXI)

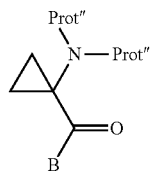

(XXXI)

wherein B is as defined herein for a compound of formula (I), and Prot" represents a carbamate, amide or sulfonamide; or a salt or N-oxide thereof. In the compounds of formula (XXXI), Prot" preferably represents carbamates of formula:

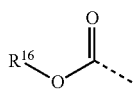

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl or 4-bromobenzyl;

or amides of formula:

wherein R17 represents hydrogen, C1-C4 alkyl, C1-C4 haloalkyl, C1-C4 alkoxylalkyl, C2-C4 alkenyl, benzyl or phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro;

or sulfonamides of formula:

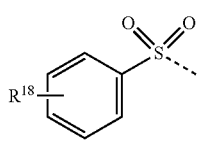

wherein the phenyl ring is optionally substituted by one or more R18 as defined previously. The preferred definitions of B defined in respect of compounds of formula (I) also apply to compounds of formula (XXXI).

Preferably for compounds of formula (XXXI), Prot″ represents carbamates of formula:

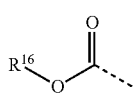

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl or 4-bromobenzyl;

or amides of formula:

wherein R17 represents hydrogen, C1-C4 alkyl, C1-C4 haloalkyl, C1-C4 alkoxylalkyl, C2-C4 alkenyl, benzyl or phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro.

In a further aspect, the invention provides a compound of formula (XXXIV)

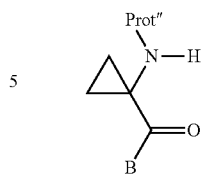

(XXXIV)

wherein B is as defined herein for a compound of formula (I), and Prot‴ represents a carbamate, amide or sulfonamide; or a salt or N-oxide thereof; or a salt or N-oxide thereof provided that the compound of the formula (XXXIV) is not:

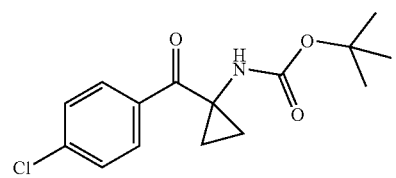 [SMILES: CC(C)(C)OC(=O)NC1(C(=O)c2ccc(Cl)cc2)CC1]

The preferred definitions of B defined in respect of compounds of formula (I) also apply to compounds of formula (XXXIV). In the compounds of formula (XXXIV), Prot‴ preferably represents carbamates of formula:

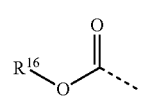

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl or 4-bromobenzyl;

or amides of formula:

wherein R20 represents hydrogen, C1-C4 alkyl, C1-C4 haloalkyl, C1-C4 alkoxylalkyl, C2-C4 alkenyl or benzyl;

or sulfonamides of formula:

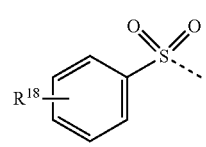

wherein the phenyl ring is optionally substituted by one or more R18 as defined previously.

Preferably for compounds of formula (XXXIV), Prot‴ represents carbamates of formula:

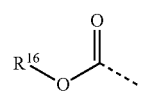

wherein R16 represents C1-C4 alkyl, C1-C4 haloalkyl, C2-C4 alkenyl, benzyl, 4-methoxybenzyl, 4-nitrobenzyl, 4-chlorobenzyl, 2,4-dichlorobenzyl or 4-bromobenzyl;
or amides of formula:

wherein R20 represents hydrogen, C1-C4 alkyl, C1-C4 haloalkyl, C1-C4 alkoxylalkyl, C2-C4 alkenyl or benzyl.

Preferably for compounds of formula (XXXIV), when Prot''' represents an amide of formula

then R20 represents preferably hydrogen, C1-C4 alkyl, C1-C4 haloalkyl, C1-C4 alkoxylalkyl, C2-C4 alkenyl or benzyl.

In a further aspect, the invention provides a compound of formula (XXX)

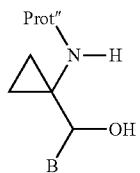

(XXX)

wherein B is as defined herein for a compound of formula (I), and Prot'' is as defined herein for the compounds of formula (XXXI); or a salt or N-oxide thereof, provided that the compounds of the formula (XXX) are not

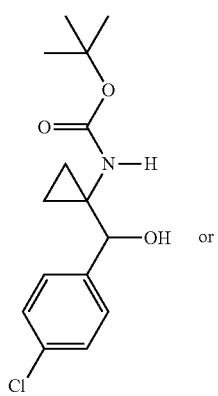

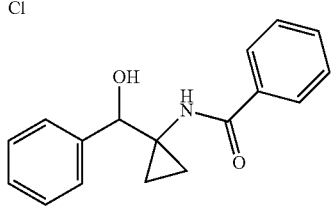

The preferred definitions of B defined in respect of compounds of formula (I) also apply to compounds of formula (XXX). The preferred definitions of Prot'' defined in respect of compounds of formula (XXXI) also apply to compounds of formula (XXX).

In a further aspect, the invention provides a compound of formula (XXIX)

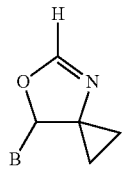

(XXIX)

wherein B is as defined herein for a compound of formula (I); or a salt or N-oxide thereof provided that the compound of formula (XXIX) is not

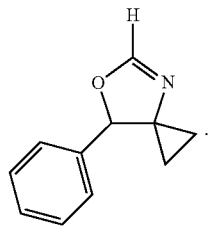 [SMILES: C1=NC2(CC2)C(c2ccccc2)O1]

The preferred definitions of B defined in respect of compounds of formula (I) also apply to compounds of formula (XXIX).

In a further aspect, the invention provides a compound of formula (XXII)

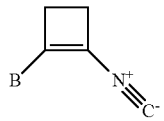

(XXII)

wherein B is as defined herein for a compound of formula (I); or a salt or N-oxide thereof. The preferred definitions of B defined in respect of compounds of formula (I) also apply to compounds of formula (XXII).

In a further aspect, the invention provides a compound of formula (XXIII)

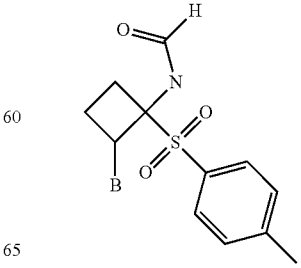

(XXIII)

wherein B is as defined herein for a compound of formula (I); or a salt or N-oxide thereof. The preferred definitions of B defined in respect of compounds of formula (I) also apply to compounds of formula (XXIII).

In a further aspect, the invention provides a compound of formula (XXIV)

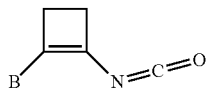

(XXIV)

wherein B is as defined herein for a compound of formula (I); or a salt or N-oxide thereof. The preferred definitions of B defined in respect of compounds of formula (I) also apply to compounds of formula (XXIV).

In a further aspect, the invention provides a compound of formula (XXV)

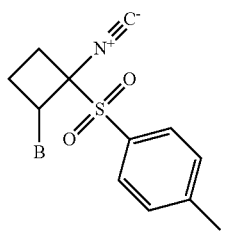

(XXV)

wherein B is as defined herein for a compound of formula (I); or a salt or N-oxide thereof. The preferred definitions of B defined in respect of compounds of formula (I) also apply to compounds of formula (XXV).

In a further aspect, the invention provides a compound of formula (XXXVI)

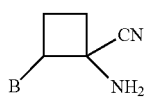

(XXXVI)

wherein B is as defined herein for a compound of formula (I); or a salt or N-oxide thereof. The preferred definitions of B defined in respect of compounds of formula (I) also apply to compounds of formula (XXXVI).

The compounds of formula (XXXVI) can exist as both cis and trans isomers. Accordingly, in a further aspect, the invention provides a compound of formula (XXXVIa)

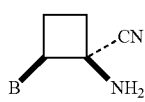

(XXXVIa)

wherein B is as defined herein for a compound of formula (I) and the amine moiety and B are cis to each other; or a salt or N-oxide thereof. The preferred definitions of B defined in respect of compounds of formula (I) also apply to compounds of formula (XXXVIa).

In a further aspect, the invention provides a compound of formula (XXXVIb)

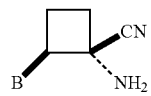

(XXXVIb)

wherein B is as defined herein for a compound of formula (I) and the amine moiety and B are trans to each other; or a salt or N-oxide thereof. The preferred definitions of B defined in respect of compounds of formula (I) also apply to compounds of formula (XXXVIb).

In a further aspect, the invention provides a compound of formula (XXXVII)

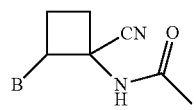

(XXXVII)

wherein B is as defined herein for a compound of formula (I); or a salt or N-oxide thereof. The preferred definitions of B defined in respect of compounds of formula (I) also apply to compounds of formula (XXXVII).

The compounds of formula (XXXVII) can exist as both cis and trans isomers. Accordingly, in a further aspect, the invention provides a compound of formula (XXXVIIa)

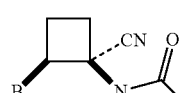

(XXXVIIa)

wherein B is as defined herein for a compound of formula (I) and the amine moiety and B are cis to each other; or a salt or N-oxide thereof. The preferred definitions of B defined in respect of compounds of formula (I) also apply to compounds of formula (XXXVIIa).

in a further aspect, the invention provides a compound of formula (XXXVIIb)

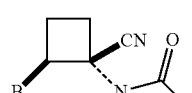

(XXXVIIb)

wherein B is as defined herein for a compound of formula (I) and the amine moiety and B are trans to each other; or a salt or N-oxide thereof. The preferred definitions of B defined in respect of compounds of formula (I) also apply to compounds of formula (XXXVIIb).

In a further aspect, the invention provides a compound of formula (XXXVIII)

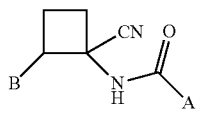

(XXXVIII)

wherein A and B are as defined herein for a compound of formula (I); or a salt or N-oxide thereof, provided that when B and the amide group are cis- to each other, then B is not 4-chlorophenyl.

The preferred definitions of B defined in respect of compounds of formula (I) also apply to compounds of formula (XXXVIII).

The compounds of formula (XXXVIII) can exist as both cis and trans isomers. Accordingly, in a further aspect, the invention provides a compound of formula (XXXVIIIa)

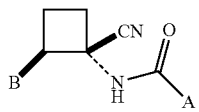

(XXXVIIIa)

wherein A and B is as defined herein for a compound of formula (I) and the amine moiety and B are trans to each other; or a salt or N-oxide thereof The preferred definitions of B defined in respect of compounds of formula (I) also apply to compounds of formula (XXXVIIIa).

In a further aspect, the invention provides a compound of formula (XXXVIIIb)

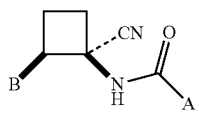

(XXXVIIIb)

wherein A and B is as defined herein for a compound of formula (I) and the amine moiety and B are cis to each other; or a salt or N-oxide thereof.

The preferred definitions of B defined in respect of compounds of formula (I) also apply to compounds of formula (XXXVIIIb).

Tables 1 to 56: Compounds of Formula (IA)

The invention is further illustrated by making available the following individual compounds of formula (IA) listed below in Tables 1 to 56.

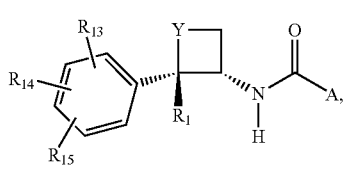

(IA)

Each of Tables 1 to 56, which follow the Table P below, make available 80 compounds of the formula (IA) in which Y, $R_1$, R13, R14 and R15 are the substituents defined in Table P and A is the substituent defined in the relevant Table 1 to 56. Thus Table 1 individualises 80 compounds of formula (IA) wherein for each row of Table P, the A substituent is as defined in Table 1; similarly, Table 2 individualises 80 compounds of formula (IA) wherein for each row of Table P, the A substituent is as defined in Table 2; and so on for Tables 3 to 56.

TABLE P

| Compound | Y | $R_1$ | R13 | R14 | R15 |
|---|---|---|---|---|---|
| P.1 | $CH_2$ | H | 4-Cl | H | H |
| P.2 | $CH_2$ | Me | 4-Cl | H | H |
| P.3 | $CH_2$ | nPr | 4-Cl | H | H |
| P.4 | $CH_2$ | F | 4-Cl | H | H |
| P.5 | $CH_2$ | CN | 4-Cl | H | H |
| P.6 | $CH_2$ | $CF_3$ | 4-Cl | H | H |
| P.7 | O | H | 4-Cl | H | H |
| P.8 | $CH_2$ | H | 2-Cl | H | H |
| P.9 | $CH_2$ | H | 3-Cl | H | H |
| P.10 | $CH_2$ | H | 3-Cl | 4-Cl | H |
| P.11 | $CH_2$ | H | 3-Cl | 5-Cl | H |
| P.12 | $CH_2$ | H | 4-F | H | H |
| P.13 | $CH_2$ | H | 4-$OCHF_2$ | H | H |
| P.14 | $CH_2$ | H | 2-Cl | 4-Br | H |
| P.15 | $CH_2$ | H | 2-Cl | 4-Cl | H |
| P.16 | $CH_2$ | H | 2-Cl | 4-$CF_3$ | H |
| P.17 | $CH_2$ | H | 2-Cl | 5-Cl | H |
| P.18 | $CH_2$ | H | 2-Cl | 6-Cl | H |
| P.19 | $CH_2$ | H | 2-F | 4-Cl | H |
| P.20 | $CH_2$ | H | 2-F | 4-Br | H |
| P.21 | $CH_2$ | H | 4-$CF_3$ | H | H |
| P.22 | $CH_2$ | H | 2-F | 4-$CF_3$ | H |
| P.23 | $CH_2$ | H | 3-F | 4-Cl | H |
| P.24 | $CH_2$ | H | 4-$OCF_3$ | H | H |
| P.25 | $CH_2$ | H | 4-Br | H | H |
| P.26 | $CH_2$ | H | 3-Br | H | H |
| P.27 | $CH_2$ | H | 4-CN | H | H |
| P.28 | $CH_2$ | H | 2-$CF_3$ | 4-F | H |
| P.29 | $CH_2$ | H | 2-Br | 4-F | H |
| P.30 | $CH_2$ | H | 2-Br | H | H |
| P.31 | $CH_2$ | H | 4-SMe | H | H |
| P.32 | $CH_2$ | H | 4-S(O)Me | H | H |
| P.33 | $CH_2$ | H | 4-$S(O)_2$Me | H | H |
| P.34 | $CH_2$ | H | 2-F | 4-F | H |
| P.35 | $CH_2$ | H | 2-Cl | 4-F | H |
| P.36 | $CH_2$ | H | 2-F | 4-F | 6-F |
| P.37 | $CH_2$ | H | 4-methyl | H | H |
| P.38 | $CH_2$ | H | 4-cyclopentyl | H | H |
| P.39 | $CH_2$ | H | 4-cyclopropyl | H | H |
| P.40 | $CH_2$ | H | 4-(2,2-difluorovinyl) | H | H |
| P.41 | $CH_2$ | H | 4-(2-trifluoromethylcyclopropyl) | H | H |
| P.42 | $CH_2$ | H | 4-(4-chloro-phenyl) | H | H |
| P.43 | $CH_2$ | H | 4-methoxy | H | H |
| P.44 | $CH_2$ | H | 4-isopropoxy | H | H |
| P.45 | $CH_2$ | H | 4-cyclopentyl-oxy | H | H |
| P.46 | $CH_2$ | H | 4-allyloxy | H | H |
| P.47 | $CH_2$ | H | 4-propargyloxy | H | H |
| P.48 | $CH_2$ | H | 4-(4-chloro-phenyl)oxy | H | H |
| P.49 | $CH_2$ | H | 4-cyclopentyl sulfonyl | H | H |
| P.50 | $CH_2$ | H | 4-allyl sulfonyl | H | H |
| P.51 | $CH_2$ | H | 4-propargyl sulfonyl | H | H |
| P.52 | $CH_2$ | H | 4-(4-chloro-phenyl) sulfonyl | H | H |
| P.53 | $CH_2$ | H | 4-(3,5-dichloro-pyrid-2yl) sulfonyl | H | H |
| P.54 | O | H | 2-Cl | H | H |
| P.55 | O | H | 4-F | H | H |
| P.56 | O | H | 4-$OCHF_2$ | H | H |
| P.57 | O | H | 2-Cl | 4-Br | H |
| P.58 | O | H | 2-Cl | 4-Cl | H |
| P.59 | O | H | 2-F | 4-Cl | H |
| P.60 | O | H | 4-$CF_3$ | H | H |
| P.61 | O | H | 2-F | 4-$CF_3$ | H |
| P.62 | O | H | 3-F | 4-Cl | H |
| P.63 | O | H | 4-$OCF_3$ | H | H |
| P.64 | O | H | 4-Br | H | H |
| P.65 | O | H | 4-CN | H | H |
| P.66 | O | H | 2-$CF_3$ | 4-F | H |
| P.67 | O | H | 2-Br | 4-F | H |
| P.68 | O | H | 4-SMe | H | H |

TABLE P-continued

| Compound | Y | R₁ | R13 | R14 | R15 |
|---|---|---|---|---|---|
| P.69 | O | H | 4-S(O)Me | H | H |
| P.70 | O | H | 4-S(O)₂Me | H | H |
| P.71 | O | H | 2-F | 4-F | H |
| P.72 | O | H | 2-Cl | 4-F | H |
| P.73 | O | H | 2-F | 4-F | 6-F |
| P.74 | O | H | 4-methyl | H | H |
| P.75 | O | H | 4-cyclopentyl | H | H |
| P.76 | O | H | 4-cyclopropyl | H | H |
| P.77 | O | H | 4-allyl | H | H |
| P.78 | O | H | 4-propargyl | H | H |
| P.79 | O | H | 4-(4-chloro-phenyl) | H | H |
| P.80 | O | H | 4-(3,5-dichloro-pyrid-2yl) | H | H |

Table 1 provides 80 compounds of formula (IA), wherein A is

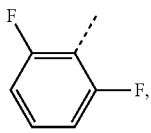
(A1)

(2,6-difluorophenyl) wherein the broken line indicates the point of attachment of the group A to the amide group, and Y, R₁, R13, R14 and R15 are as defined in each row of Table P. For example, compound 1.001 has the following structure:

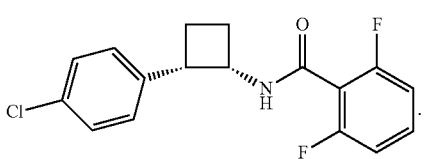
(1.001)

Table 2 provides 80 compounds of formula (IA) wherein A is 2-chloro-3-pyrazinyl (A2) and Y, R₁, R13, R14 and R15 are as defined in each row of Table P.

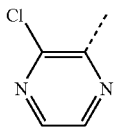

Table 3 provides 80 compounds of formula (IA) wherein A is 3-trifluoromethyl-2-pyridyl (A3) and Y, R₁, R13, R14 and R15 are as defined in each row of Table P.

Table 4 provides 80 compounds of formula (IA) wherein A is 3-chloro-2-pyridyl (A4) and Y, R₁, R13, R14 and R15 are as defined in each row of Table P.

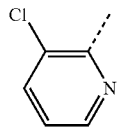

Table 5 provides 80 compounds of formula (IA) wherein A is 2-trifluoromethyl-3-pyridyl (A5) and Y, R₁, R13, R14 and R15 are as defined in each row of Table P.

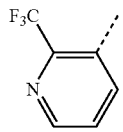

Table 6 provides 80 compounds of formula (IA) wherein A is 2-trifluoromethyl-phenyl (A6) and Y, R₁, R13, R14 and R15 are as defined in each row of Table P.

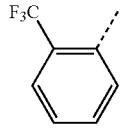

Table 7 provides 80 compounds of formula (IA) wherein A is 2-chloro-3-pyridyl (A7) and Y, R₁, R13, R14 and R15 are as defined in each row of Table P.

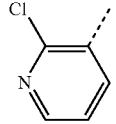

Table 8 provides 80 compounds of formula (IA) wherein A is 2-fluoro-6-trifluoromethyl-phenyl (A8) and Y, R₁, R13, R14 and R15 are as defined in each row of Table P.

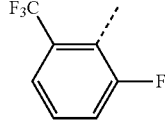

Table 9 provides 80 compounds of formula (IA) wherein A is 2-tolyl (A9) and Y, R₁, R13, R14 and R15 are as defined in each row of Table P.

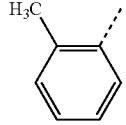

Table 10 provides 80 compounds of formula (IA) wherein A is 2-pyrimidinyl (A10) and Y, R₁, R13, R14 and R15 are as defined in each row of Table P.

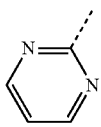

Table 11 provides 80 compounds of formula (IA) wherein A is 3-methyl-2-pyridyl (A11) and Y, $R_1$, R13, R14 and R15 are as defined in each row of Table P.

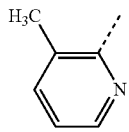

Table 12 provides 80 compounds of formula (IA) wherein A is 2-fluorophenyl (A12) and Y, $R_1$, R13, R14 and R15 are as defined in each row of Table P.

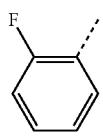

Table 13 provides 80 compounds of formula (IA) wherein A is 2-chlorophenyl (A13) and Y, $R_1$, R13, R14 and R15 are as defined in each row of Table P.

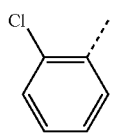

Table 14 provides 80 compounds of formula (IA) wherein A is 2-bromophenyl (A14) and Y, $R_1$, R13, R14 and R15 are as defined in each row of Table P.

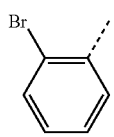

Table 15 provides 80 compounds of formula (IA) wherein A is 2-iodophenyl (A15) and Y, $R_1$, R13, R14 and R15 are as defined in each row of Table P.

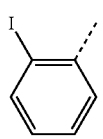

Table 16 provides 80 compounds of formula (IA) wherein A is 2,6-dichlorophenyl (A16) and Y, R13, R14 and R15 are as defined in each row of Table P.

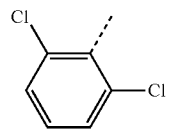

Table 17 provides 80 compounds of formula (IA) wherein A is 2-chloro-6-fluoro-phenyl (A17) and Y, $R_1$, R13, R14 and R15 are as defined in each row of Table P.

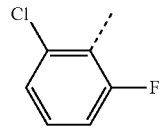

Table 18 provides 80 compounds of formula (IA) wherein A is 2,4,6-trifluorophenyl (A18) and Y, $R_1$, R13, R14 and R15 are as defined in each row of Table P.

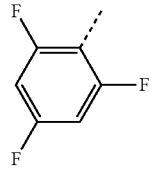

Table 19 provides 80 compounds of formula (IA) wherein A is 2-trifluoromethoxy-phenyl (A19) and Y, $R_1$, R13, R14 and R15 are as defined in each row of Table P.

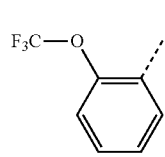

Table 20 provides 80 compounds of formula (IA) wherein A is 2-fluoro-6-methyl-phenyl (A20) and Y, $R_1$, R13, R14 and R15 are as defined in each row of Table P.

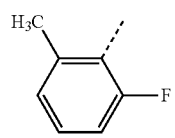

Table 21 provides 80 compounds of formula (IA) wherein A is 2-fluoro-6-methoxy-phenyl (A21) and Y, $R_1$, R13, R14 and R15 are as defined in each row of Table P.

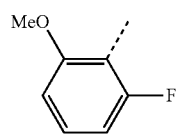

Table 22 provides 80 compounds of formula (IA) wherein A is 2-methyl-3-pyridyl (A22) and $R_1$, R13, R14 and R15 are as defined in each row of Table P.

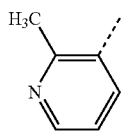

Table 23 provides 80 compounds of formula (IA) wherein A is 3-fluoro-2-pyridyl (A23) and Y, $R_1$, R13, R14 and R15 are as defined in each row of Table P.

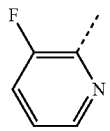

Table 24 provides 80 compounds of formula (IA) wherein A is 3-methyl-2-pyrazinyl (A24) and Y, $R_1$, R13, R14 and R15 are as defined in each row of Table P.

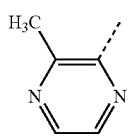

Table 25 provides 80 compounds of formula (IA) wherein A is 3-bromo-2-pyrazinyl (A25) and Y, $R_1$, R13, R14 and R15 are as defined in each row of Table P.

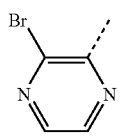

Table 26 provides 80 compounds of formula (IA) wherein A is 3-trifluoromethyl-2-pyrazinyl (A26) and Y, $R_1$, R13, R14 and R15 are as defined in each row of Table P.

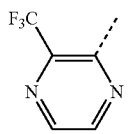

Table 27 provides 80 compounds of formula (IA) wherein A is 2-methyl-3-furyl (A27) and Y, $R_1$, R13, R14 and R15 are as defined in each row of Table P.

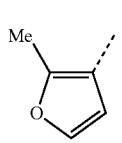

Table 28 provides 80 compounds of formula (IA) wherein A is 5-chloro-4-pyrimidinyl (A28) and Y, $R_1$, R13, R14 and R15 are as defined in each row of Table P.

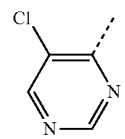

Table 29 provides 80 compounds of formula (IA) wherein A is 2-cyanophenyl (A29) and Y, $R_1$, R13, R14 and R15 are as defined in each row of Table P.

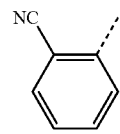

Table 30 provides 80 compounds of formula (IA) wherein A is 2-trifluoromethylthio-phenyl (A30) and Y, $R_1$, R13, R14 and R15 are as defined in each row of Table P.

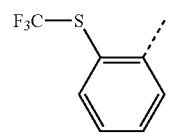

Table 31 provides 80 compounds of formula (IA) wherein A is 3-bromo-2-pyridyl (A31) and Y, $R_1$, R13, R14 and R15 are as defined in each row of Table P.

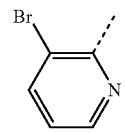

Table 32 provides 80 compounds of formula (IA) wherein A is 5-bromo-4-thiazolyl (A32) and Y, $R_1$, R13, R14 and R15 are as defined in each row of Table P.

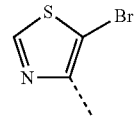

Table 33 provides 80 compounds of formula (IA) wherein A is 2-trifluoromethyl-3-thienyl (A33) and Y, $R_1$, R13, R14 and R15 are as defined in each row of Table P.

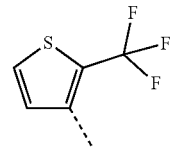

Table 34 provides 80 compounds of formula (IA) wherein A is 2-iodo-3-thienyl (A34) and Y, $R_1$, R13, R14 and R15 are as defined in each row of Table P.

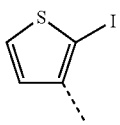

Table 35 provides 80 compounds of formula (IA) wherein A is 2-chloro-3-thienyl (A35) and Y, R₁, R13, R14 and R15 are as defined in each row of Table P.

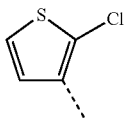

Table 36 provides 80 compounds of formula (IA) wherein A is 3-bromo-2-thienyl (A36) and Y, R₁, R13, R14 and R15 are as defined in each row of Table P.

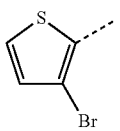

Table 37 provides 80 compounds of formula (IA) wherein A is 3-chloro-2-thienyl (A37) and Y, R₁, R13, R14 and R15 are as defined in each row of Table P.

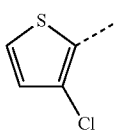

Table 38 provides 80 compounds of formula (IA) wherein A is 2-bromo-3-thienyl (A38) and Y, R₁, R13, R14 and R15 are as defined in each row of Table P.

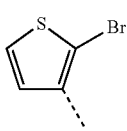

Table 39 provides 80 compounds of formula (IA) wherein A is 4-methyl-5-[1,2,3]-thiadiazolyl (A39) and Y, R₁, R13, R14 and R15 are as defined in each row of Table P.

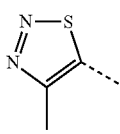

Table 40 provides 80 compounds of formula (IA) wherein A is 4-cyclopropyl-5-[1,2,3]-thiadiazolyl (A40) and Y, R₁, R13, R14 and R15 are as defined in each row of Table P.

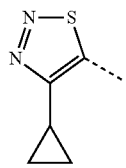

Table 41 provides 80 compounds of formula (IA) wherein A is 3-methyl-4-isothiazolyl (A41) and Y, R₁, R13, R14 and R15 are as defined in each row of Table P.

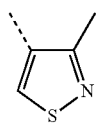

Table 42 provides 80 compounds of formula (IA) wherein A is 5-methyl-4-isoxazolyl (A42) and Y, R₁, R13, R14 and R15 are as defined in each row of Table P.

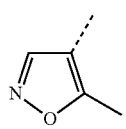

Table 43 provides 80 compounds of formula (IA) wherein A is 5-cyclopropyl-4-isoxazolyl (A43) and Y, R₁, R13, R14 and R15 are as defined in each row of Table P.

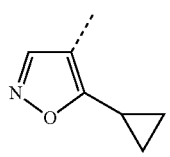

Table 44 provides 80 compounds of formula (IA) wherein A is 2-(trifluoromethyl)furan-3-yl (A44) and Y, R₁, R13, R14 and R15 are as defined in each row of Table P.

Table 45 provides 80 compounds of formula (IA) wherein A is 2-bromofuran-3-yl (A45) and Y, R13, R14 and R15 are as defined in each row of Table P.

Table 46 provides 80 compounds of formula (IA) wherein A is 4-(trifluoromethyl)pyridazin-3-yl (A46) and Y, $R_1$, R13, R14 and R15 are as defined in each row of Table P.

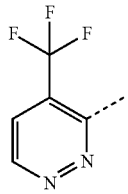

Table 47 provides 80 compounds of formula (IA) wherein A is 3,6-difluoro-2-(trifluoromethyl)phenyl (A47) and Y, $R_1$, R13, R14 and R15 are as defined in each row of Table P.

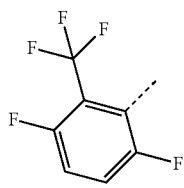

Table 48 provides 80 compounds of formula (IA) wherein A is 2-bromo-3,6-difluorophenyl (A48) and Y, $R_1$, R13, R14 and R15 are as defined in each row of Table P.

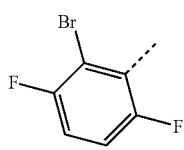

Table 49 provides 80 compounds of formula (IA) wherein A is 2-chloro-3,6-difluorophenyl (A49) and Y, $R_1$, R13, R14 and R15 are as defined in each row of Table P.

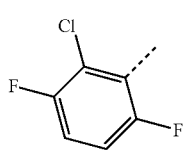

Table 50 provides 80 compounds of formula (IA) wherein A is 4-(trifluoromethyl)pyrimidin-5-yl (A50) and Y, $R_1$, R13, R14 and R15 are as defined in each row of Table P.

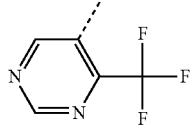

Table 51 provides 80 compounds of formula (IA) wherein A is 4-(trifluoromethyl)pyrid-3-yl (A51) and Y, $R_1$, R13, R14 and R15 are as defined in each row of Table P.

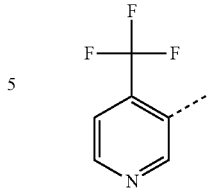

Table 52 provides 80 compounds of formula (IA) wherein A is 3-(difluoromethyl)-1-methylpyrazol-4-yl (A52) and Y, $R_1$, R13, R14 and R15 are as defined in each row of Table P.

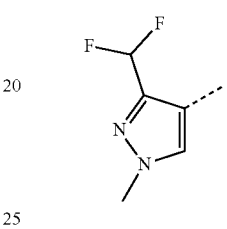

Table 53 provides 80 compounds of formula (IA) wherein A is 4-methyloxazol-5-yl (A53) and Y, $R_1$, R13, R14 and R15 are as defined in each row of Table P.

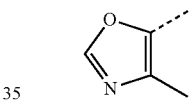

Table 54 provides 80 compounds of formula (IA) wherein A is 3-methoxypyrid-2-yl (A54) and Y, $R_1$, R13, R14 and R15 are as defined in each row of Table P.

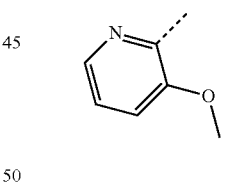

Table 55 provides 80 compounds of formula (IA) wherein A is 2-chlorofuran-3-yl (A55) and Y, $R_1$, R13, R14 and R15 are as defined in each row of Table P.

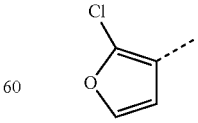

Table 56 provides 80 compounds of formula (IA) wherein A is 2-iodofuran-3-yl (A56) and Y, $R_1$, R13, R14 and R15 are as defined in each row of Table P.

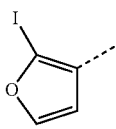

The compounds in Tables 1 to 56 include all isomers, tautomers and mixtures thereof, including the cis/trans isomers shown above.

The compounds of the invention may be made by a variety of methods, illustrated in schemes 1-9.

SCHEME 1

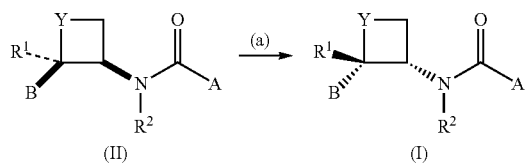

Scheme 1 provides methods of providing the compounds of formula (I). Each of these methods form part of the invention.

Step (a)

Compounds of formula (I) may be prepared by resolution of a compound of formula (II), which is a racemic mixture of the compound of formula (I) and its enantiomer, by known methods, for example by recrystallization from an optically active solvent, by chromatography on chiral adsorbents, for example high-performance liquid chromatography (HPLC) on acetyl celulose, with the aid of suitable microorganisms, by cleavage with specific enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Compounds of formula (II) may be prepared using techniques described below, or by the methods described in WO2013/143811.

SCHEME 2

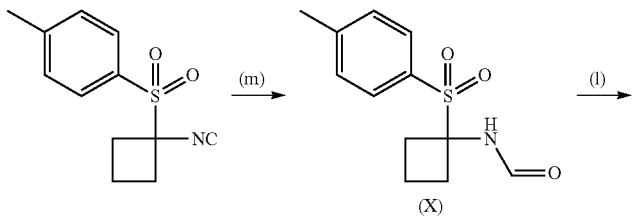

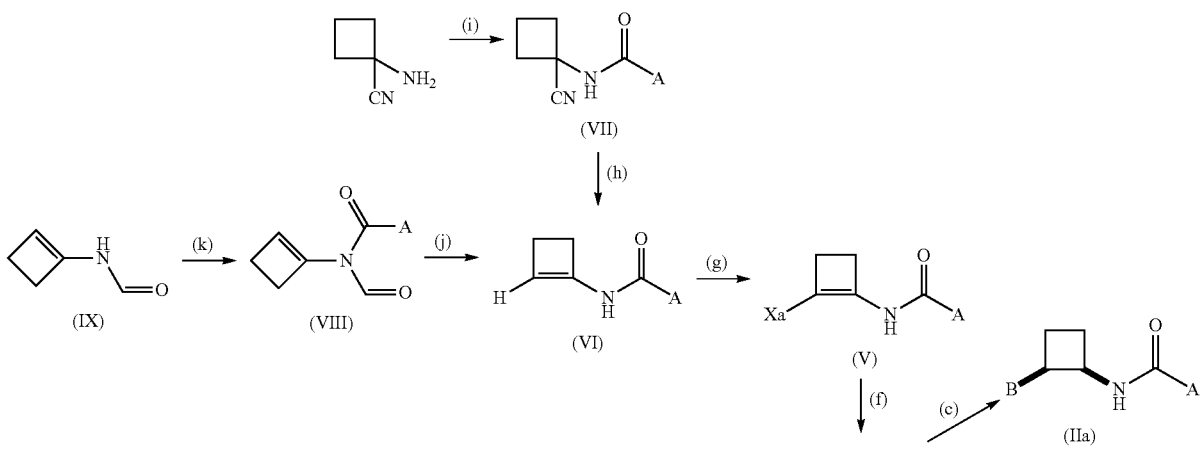

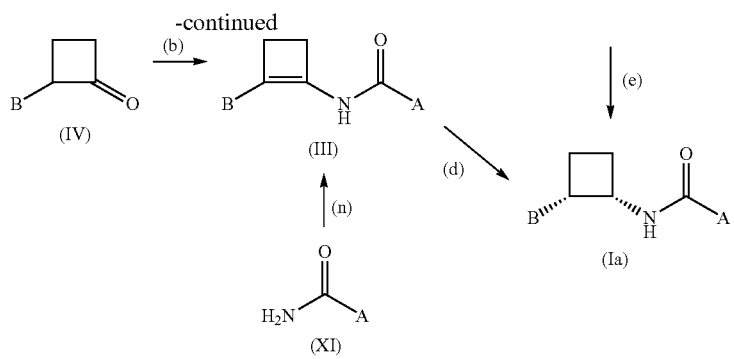

Scheme 2

Scheme 2 provides methods of providing the compounds of formula (Ia), that is a compound of formula (I) wherein Y is CH2, R1 is H and R2 is H, compounds of formula (IIa), that is a compound of formula (II) wherein Y is CH2, R1 is H and R2 is H, compounds of formula (III), compounds of formula (V), compounds of the formula (VI), compounds of the formula (VII), compounds of formula (VIII), compounds of formula (IX) and compounds of formula (X). Each of these methods form part of the invention.

Step (b)

Compounds of the formula (III) can be prepared from compounds of the formula (IV) by treatment with titanium tetraalkoxide and ammonia followed by treatment with an acid chloride of the formula A-CO—Cl, wherein A is as defined herein for a compound of formula (I).

Compounds of the formula (III) can also be prepared from the compounds of formula (IV) by treatment with trialkyl-aluminium and an amide of the formula A-CO—NH2 wherein A is as defined herein for a compound of formula (I).

Alternatively compounds of formula (III) can be prepared from compounds of formula (IV) and an amide of formula A-CO—NH2 wherein A is as defined herein for a compound of formula (I) in the presence of a Bronsted acid, for example p-toluenesulfonic acid, and by performing an azeotropic distillation of water for example with toluene.

Step (c)

The compound of formula (IIa) can be prepared by reduction of the compound of formula (III). A typical reducing agent is molecular hydrogen in the presence of a catalyst. Typical catalysts are transition metals or their salts or complexes. Use of a racemic or achiral catalyst gives a compound of formula (IIa).

Step (d)

The compound of formula (Ia) can be prepared by reduction of the compound of formula (III) using molecular hydrogen in the presence of a catalyst. A chiral or enantioenriched catalyst can be used to prepare the compounds of formula (Ia). A description of catalysts, which can be used to reduce enamides to enantioenriched amides can be found in Hu, X-P., Zheng, Z. in Chiral Amine Synthesis, Edited by Nugent, T. C. (2010), 273-298; also in Nugent, T. C.; El-Shazly, M. Advanced Synthesis & Catalysis (2010), 352(5), 753-819; also in Genet, J. P. ACS Symposium Series (1996), 641 (Reductions in Organic Synthesis), 31-51. An example of a reduction with a ruthenium catalyst is given in Noyori at al, J. Org. Chem. 1994, 59, 297-310.

Step (e)

Compounds of formula (Ia) may be prepared by resolution of a compound of formula (II) using analogous methods to those described above under step (a).

Step (f)

Compounds of the formula (III) can also be formed by treatment of compounds of the formula (V), wherein Xa is a halogen, preferably chlorine, bromine or iodine, and A is as defined herein for compounds of formula (I), with an arylating agent of the formula B-M, wherein B is as defined herein for compounds of formula (I) and M is a metal or metalloid. Examples of B-M are aryl lithium, aryl Grignard, aryl zinc halide, aryl boronic acid or boronate or aryl trimethylsilane. The coupling of B-M with (V) is assisted by catalysis. Typical catalysts are transition metal catalysts. Typical transition metal catalysts are salts of palladium, nickel, cobalt, or iron. These salts are often complexed with ligands such as phosphines, amines or carbenes.

Step (g)

Compounds of formula (V) can be prepared by treatment of compounds of the formula (VI), wherein A is as defined herein for the compounds of formula (I), with a halogenating agent. Common halogenating agents are N-bromosuccinimide, N-chlorosuccinimide, N-iodosuccinimide, Cl2, Br2 and I2.

Step (h)

Compounds of formula (VI) can be prepared by treatment of compounds of the formula (VII), wherein A is as defined herein for the compounds of formula (I), with a base. Typical bases that can be used for this transformation are metal alkoxides, metal hydrides, and metal amides. Preferred bases are metal alkoxides, in particular sodium alkoxide, most particularly sodium t-butoxide.

Step (i)

Compounds of formula (VII) can be prepared by acylation of 1-cyano-cyclobutanamine with an acylating agent of formula (XXI)

A-C(=O)—R*    (XXI), in which A is as defined under formula I, and R* is halogen, hydroxyl or $C_{1-6}$ alkoxy, preferably chloro, in the presence of a base, such as triethylamine, Hünig base, sodium bicarbonate, sodium carbonate, potassium carbonate, pyridine or quinoline, but preferably triethylamine, and generally in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxyl, a coupling agent, such as benzo-triazol-1-yloxytris(dimethylamino)phosphoniumhexafluo-rophosphate, bis-(2-oxo-3-oxazolidinyl)-phosphinic acid chloride (BOP—Cl), N,N'-dicyclohexylcarbodiimide (DCC) or 1,1'-carbonyl-diimidazole (CDI), may be used.

Step (j)

Compounds of formula (VI) can also be prepared by selective hydrolysis of compounds of formula (VIII) by using a base. Typical bases that can be used for this as defined herein for a compound of formula (I) with a dialkylaluminium hydride followed by treatment with a compound of formula (IV) and further treatment by an acid chloride such as acetyl chloride, an acid anhydride such as acetic anhydride or trifluoroacetic anhydride or a sulfonyl-chloride such as p-toluenesulfonylchloride.

SCHEME 3

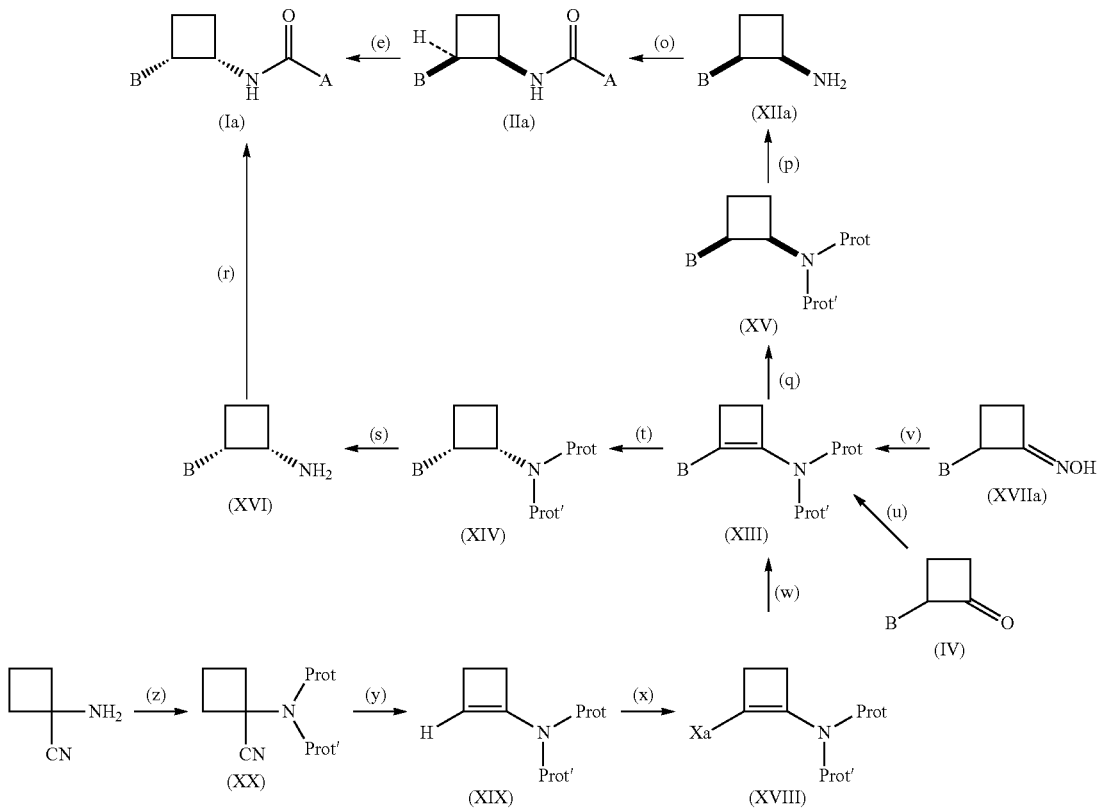

transformation are metal alkoxides, metal carbonates. Alternatively compounds of formula (VIII) can be heated in alcohols such as ethanol or isopropanol.

Step (k)

Compounds of formula (VIII) can be prepared by acylation of compounds of formula (IX) with an acylating agent of the formula (XXI), using methodology described above under step (i).

Step (l)

Compound of formula (IX) can be prepared by treatment of compounds of formula (X) using a base. Typical bases that can be used for this transformation are metal alkoxides, metal hydrides, and metal amides. Preferred bases are metal alkoxides, in particular sodium alkoxide, most particularly sodium t-butoxide.

Step (m)

Compound of formula (X) can be prepared by hydrolysis of known compound 1-(1-isocyanocyclobutyl)sulfonyl-4-methyl-benzene by the use of acid. Typical acids that can be used for this transformation are mineral acids such as hydrochloric acid, sulphuric acid, or carboxylic acids such as acetic acid or citric acid.

Step (n)

Compounds of the formula (III) can also be prepared by treatment of a compound of the formula (XI) wherein A is Scheme 3 provides methods of providing the compounds of formula (Ia), compounds of formula (IIa), compounds of formula (XIIa), that is a compound of formula (XII) wherein Y is $CH_2$, R1 is H and R2 is H, compounds of the formula (XIII), compounds of the formula (XIV) wherein Prot and Prot' are as defined herein for a compound of formula (XIII), compounds of the formula (XV) wherein Prot and Prot' are as defined herein for a compound of formula (XIII), compounds of the formula (XVI) wherein Prot and Prot' are as defined herein for a compound of formula (XIII), compounds of formula (XVIII), compounds of formula (XIX) wherein Prot and Prot' are as defined herein for a compound of formula (XIII) and compounds of formula (XX). Each of these methods form part of the invention.

Step (o)

Compounds of the formula (IIa) can also be formed by treatment of amines of the formula (XIIa) with an acylating agent of the formula (XXI) using methodology described above under step (i).

Compounds of formula (XIIa) can be prepared as described in WO2013/143811 or as described below.

Step (p)

Compounds of the formula (XIIa) can also be formed by deprotection of compounds of the formula (XV). Protected amine groups are well known for example in P. G. M. Wuts and T. W. Greene in Greene's Protective Groups in Organic Synthesis 4$^{th}$ Edn. Wiley 2007. pp 696-926. The methods of deprotection depend on the protecting group and are well known and described in Wuts and Greene. Preferred protecting groups are amides and carbamates.

Step (q)

The compounds of formula (XV) are prepared by reduction of the compounds of formula (XIII). This reduction is preferably performed with molecular hydrogen, preferably in the presence of a catalyst. The catalyst is preferably a metal salt or metal complex, where the metal is preferably a transition metal (e.g. Ir, Rh, Pd, Ni and Ru). Achiral or racemic catalysts will lead to compounds of the formula (XV).

Step (r)

Compounds of the formula (Ia) can be also be formed by treatment of compounds of the formula (XVI), wherein B is as defined herein for a compound of formula (I), with an acylating agent of the formula (XXI) using methodology described above under step (i).

Step (s).

Compounds of the formula (XVI) are formed by deprotection of compounds of the formula (XIV). Protected amine groups are well known for example in P. G. M. Wuts and T. W. Greene in Greene's Protective Groups in Organic Synthesis 4$^{th}$ Edn. Wiley 2007. pp 696-926. The methods of deprotection depend on the protecting group and are well known and described in Wuts and Greene. Preferred protecting groups are amides and carbamates Step (t)

The compounds of formula (XIV) are prepared by reduction of the compounds of formula (XIII). This reduction is preferably performed with molecular hydrogen, preferably in the presence of a catalyst. The catalyst is preferably a metal salt or metal complex, where the metal is preferably a transition metal (e.g. Ir, Rh, Pd, Ni and Ru). Enantioenriched catalysts, such as those mentioned in step (d), lead to compounds of the formula (XIV).

Step (u)

Compounds of the formula (XIII) can be prepared by treatment of the compounds of formula (IV) with ammonia and titanium tetraalkoxide followed by treatment with a derivatisation agent. Preferred derivating agents are acid chloride and anhydrides. Examples of this methodology are described in Reeves et al, Angew. Chem. Int. Ed., 2012, 51, 1400-1404.

Step (v)

Compounds of the formula (XIII) can also be formed by treatment of the compounds of formula (XVIIa), that is a compound of formula (XVII) wherein Y is CH2 and R1 is hydrogen, with a reducing agent in the presence of an acylating agent. Preferred reducing agents are iron metal, an iron II salt or a phosphine. Preferred acylation agent is acetic anhydride. Examples of this methodology can be found in Guan, Z-H. et al. J. Org. Chem. (2011), 76(1), 339-341, and references cited therein.

Step (w)

Compounds of the formula (XIII) can also be formed by treatment of compounds of the formula (XVIII) with an arylating agent of the formula B-M, where B is as defined in formula I, and M is a metal or metalloid. Examples of B-M are aryl lithium, aryl Grignard, aryl zinc halide, aryl boronic acid or boronate, or aryl trimethylsilane. The coupling of B-M with (XVIII) is assisted by catalysis. Typical catalysts are transition metal catalysts. Typical transition metal catalysts are salts of palladium, nickel, cobalt, or iron. These salts are often complexed with ligands such as phosphines, amines or carbenes.

Step (x)

Compounds of the formula (XVIII) can be prepared by treatment of compounds of the formula (XIX) with a halogenating agent. Common halogenating agents are N-bromosuccinimide, N-chlorosuccinimide, N-iodosuccinimide, Cl2, Br2, and I2.

Step (y)

Compounds of the formula (XIX) can be prepared by treatment of compounds of the formula (XX) with a base. Typical bases that can be used for this transformation are metal alkoxides, metal hydrides, and metal amides. Preferred bases are metal alkoxides, in particular sodium alkoxide, most particularly sodium t-butoxide.

Step (z)

Compounds of the formula (XX) can be prepared by protection of 1-cyano-cyclobutanamine with protecting groups Prot and Prot'. Protected amine groups are well known for example in P. G. M. Wuts and T. W. Greene in Greene's Protective Groups in Organic Synthesis 4$^{th}$ Edn. Wiley 2007. pp 696-926. The methods of protection depend on the protecting group and are well known and described in Wuts and Greene. Preferred protecting groups are amides and carbamates.

SCHEME 4

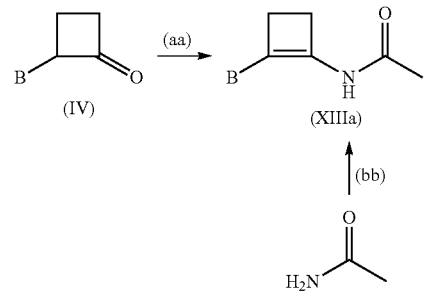

Scheme 4 provides methods of providing the compounds of formula (XIIIa), that is a compound of formula (XIII) wherein Prot' is hydrogen and Prot is COR17 wherein R17 is methyl. Each of these methods form part of the invention.

Step (aa)

Compounds of the formula (XIIIa) can be prepared from the compounds of formula (IV) by treatment with trialkylaluminium and acetamide.

Alternatively compounds of formula (XIIIa) can be prepared from compounds of formula (IV) and acetamide in the presence of a Bronsted acid, for example p-toluenesulfonic acid, and by performing an azeotropic distillation of water for example with toluene.

Step (bb)

Compounds of the formula (XIIIa) can also be prepared by treatment of acetamide with a dialkylaluminum hydride followed by treatment with a compound of formula (IV) and further treatment by an acid chloride such as acetyl chloride, an acid anhydride such as acetic anhydride or trifluoroacetic anhydride or a sulfonylchloride such as p-toluenesulfonylchloride.

SCHEME 5

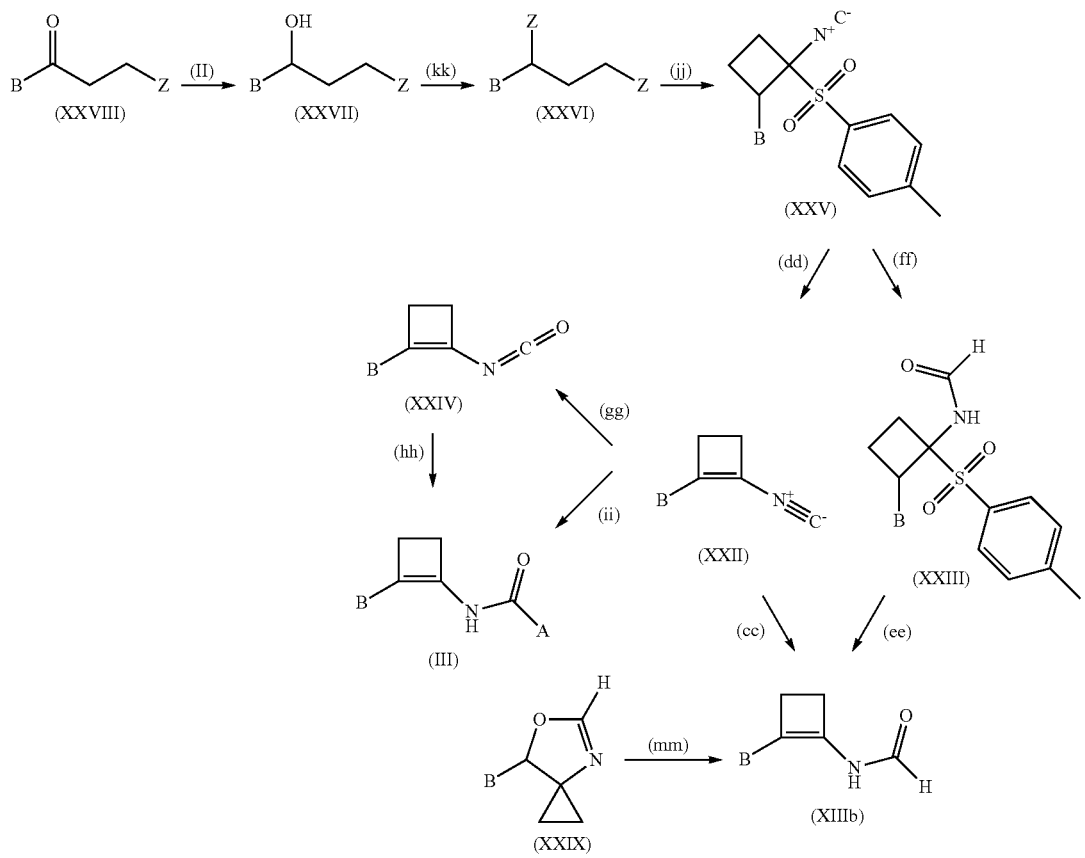

Scheme 5

Scheme 5 provides methods of providing the compounds of formula (III), (XIIIb), that is a compound of formula (XIII) wherein Prot' is hydrogen and Prot is COR17 wherein R17 is hydrogen, the compounds of the formula (XXII), the compounds of the formula (XXIII), the compounds of the formula (XXIV), the compounds of the formula (XXV) and the compounds of the formula (XXIX). Each of these methods form part of the invention.

Step (cc)
Compounds of formula (XIIIb) can be prepared by treatment of compounds of formula (XXII) with water and an acid such as citric acid or with water and a base such as sodium hydroxide Step (dd)
Compounds of formula (XXII) can be prepared by treatment of compounds of formula (XXV) with a base such as sodium hydroxide.

Step (ee)
Compounds of formula (XIIIb) can also be prepared by treatment of compounds of formula (XXIII) with base.

Step (ff)
Compounds of formula (XXIII) can be prepared by treatment of compounds of formula (XXIV) with water and an acid or a base.

Step (gg)
Compounds of formula (XXIV) can be prepared by treatment of a compound of formula (XXII) with an oxidising agent such as the combination of DMSO and trifluoroacetic anhydride.

Step (hh)
Compounds of formula (III) can be prepared by the treatment of compounds of formula (XXIV) with a compound of formula A-M wherein A is as defined herein for a compound of formula (I) and M is a metal or metalloid: for example compounds of formula A-M can be but are not limited to aryl or heteroaryl Grignard reagents, aryl or heteroaryl lithium, aryl or heteroaryl zinc halide.

Step (ii)
Compounds of formula (III) can also be prepared by treating compounds of formula (XXII) with compounds of formula A-G wherein A is as defined herein for a compound of formula (I) and G is halogen, a perfluorosufonate or a diazonium salt in the presence of a catalyst such as palladium(0) and a phosphine ligand or in the presence of a base such as potassium acetate or cesium carbonate.

Step (jj)
Compounds of formula (XXV) can be prepared by treatment of compounds of formula (XXVI) wherein B is as defined herein for a compound of formula (I) and each Z can independently be a halogen, a mesylate, a tosylate or any other leaving group with toluenesulfonylmethyl isocyanide and a base.

Step (kk)
Compounds of formula (XXVI) can be prepared by treatment of a compound of formula (XXVII) wherein B is as defined herein for a compound of formula (I) and each Z can independently be a halogen, a mesylate, a tosylate or any other leaving group. For example when Z is chlorine, compound of formula (XXVI) can be obtained by treating a compound of formula (XXVII) with a dehydrating agent and a chlorine source such as thionyl chloride, oxalyl chloride, carbon tetrachloride and triphenylphosphine, phosphorus oxychloride, cyanuric chloride, hydrochloric acid or phosphorus trichloride. When Z is a mesylate or a tosylate, compound of formula (XXVI) can be obtained by treating a compound of formula (XXVII) with methanesulfonyl chloride or paratoluenesulfonylchloride respectively.

Step (ll)

Compounds of formula (XXVII) can be prepared by treatment of a compound of formula (XXVIII) wherein B is as defined herein for a compound of formula (I) with a reducing agent.

A person skilled in the art will understand that the selection of the base used to treat compounds of formula (XXV), as well as the nature of B in the compound of formula (XXV) along with other conditions selected will determine whether the compound of formula (XXII) or the compound of formula (XXIII) is formed. Further, the skilled person will understand that steps (jj), (dd) and (cc) or (jj), (ff) and (ee) can be performed in situ and that the compounds of formula (XXV), (XXII) or (XXIII) may be isolated but that this is not necessary.

Step (mm)

Compounds of formula (XIIIb) can also be prepared by treatment of compounds of formula (XXIX) with a Lewis acid such as $BF_3.Et_2O$, $TiCl_4$, or a Brönsted acid such as HCl dissolved in an organic solvent, or sulphuric acid. Compounds of the formula (XXIX) wherein B is as defined herein for a compound of formula (I) can be prepared by dehydration of compounds of formula (XXXa), that is a compound of formula (XXX) wherein Prot" represents formyl, or by condensation of the anion of cyclopropylisonitrile with a compound of the formula B—CHO wherein B is as defined herein for a compound of formula (I) as described in Harms, R.; Schoellkopf, U.; Muramatsu, M. *Justus Liebigs Ann. Chem.* 1978, 1194-201.

agent such as thionyl chloride or sulfur trioxide pyridine complex ($Py.SO_3$) in a suitable solvent, or acetic anhydride or acetyl chloride in the presence of a Brönsted acid, such as sulphuric acid, or HCl in an organic solvent, or a Lewis acid such as $BF_3.Et_2O$.

Step (oo)

Compounds of the formula (XXX) can be prepared by reduction of the ketone group of compounds of formula (XXXIV) with a suitable reducing agent, such as for example sodium borohydride or lithium aluminium hydride.

Step (pp)

Compounds of the formula (XXXIV) can be accessed from compounds of formula (XXXI) by deprotection of one Prot" group. For example when Prot" is an amide, it can be removed by adding for example when R17 represents hydrogen, an aqueous solution of sodium hydroxide at the end of the reaction. If sodium hydroxide was chosen as the base for cyclisation, this step can be carried out together with step (qq) in a one-pot procedure. Using an excess of sodium hydroxide ensures that material deprotected prior the cyclisation is further transformed in compounds of formula (XXXIV).

Step (qq)

Compounds of the formula (XXXI) wherein for example Prot" is an amide, can be prepared by treatment of compounds of the formula (XXXII) wherein LG and LG' are each independently selected from halogen, mesylate, tosylate or any other usual leaving group, with $(R17CO)_2N-M$ wherein R17 represents hydrogen, C1-C4 alkyl, C1-C4 haloalkyl, C1-C4 alkoxylalkyl, C2-C4 alkenyl, benzyl, phenyl optionally substituted by one or more R18; wherein each R18 independently of one another represents halogen, cyano, C1-C4-alkyl, C1-C4-haloalkyl, C1-C4-alkoxy, C1-C4-haloalkoxy C1-C4-haloalkylthio, or nitro; and -M is a metal or metalloid, such as, for example but not limited to sodium or potassium. The presence of a base is required for cyclising after the substitution has taken place, the base can be, for example but not limited to, a Brönsted base such as carbonate salts of sodium or potassium, or sodium or potassium hydroxide. The base can also be an excess of $(R17CO)_2N-M$.

If sodium hydroxide is chosen as the base for cyclisation, step (pp) can be carried out together with step (qq) in a one-pot procedure. Using an excess of sodium hydroxide ensures that material deprotected prior the cyclisation is further transformed in compounds of formula (XXXIV).

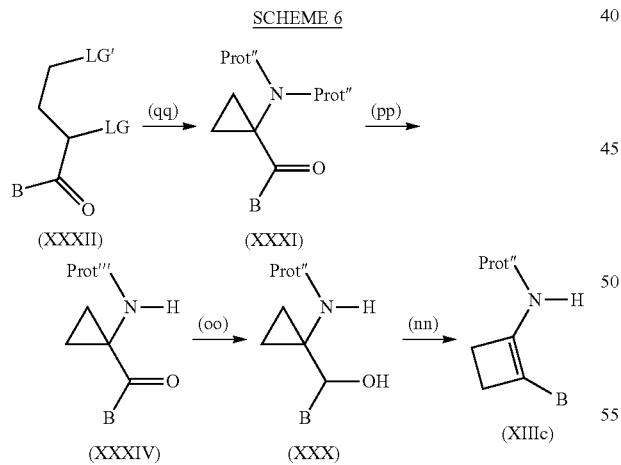

SCHEME 6

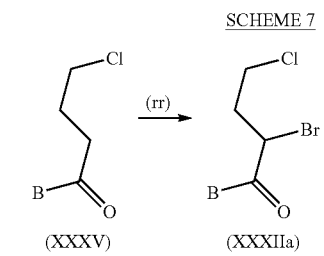

SCHEME 7

Scheme 6 provides methods of providing the compounds of formula (XXXI), compounds of formula (XXXIV), compounds of formula (XXX), and compound of formula (XIIIc) wherein Prot" is as defined herein for a compound of formula (XXXI). Each of these methods form part of the invention.

Step (nn)

Compounds of formula (XIIIc) can be prepared by treatment of compounds of formula (XXX) with a dehydrating Scheme 7 provides methods of providing the compounds of formula (XXXIIa), that is a compound of formula (XXXII) wherein LG' is chloro and LG is bromo. Each of these methods form part of the invention.

Step (rr)

Compounds of the formula (XXXIIa) can be prepared by treatment of the ketones (XXXV) wherein B is as defined herein for a compound of formula (I) (obtained for example by Friedel-Crafts acylation with a suitable acyl chloride such as described in [Bream, R. N.; Hulcoop, D. G.; Gooding, S. J.; Watson, S. A.; Blore, C. *Org. Process Res. Dev.* 2012, 16, 2043-2050 or Huang, L.-F.; Kim, J.-W.; Bauer, L.; Doss, G. *J. HeterocycL Chem.* 1997, 34, 469-476], by Grignard additions onto Weinreb's amide such as described in [Pablo, O.; Guijarro, D.; Yus, M. *J. Org. Chem.* 2013, 78, 9181-9189]) by treatment with molecular bromine, in the presence of catalytic hydrobromic acid in acetic acid, in a suitable inert solvent such as halogenoalcanes. Examples of this methodology for bromination are described in [Boeckmann, K.; Stroech, K.; Dutzmann, S.; Reinecke, P.; DE3704261A1, Bayer A.-G., Fed. Rep. Ger. 1988; p. 10 pp.].

SCHEME 8

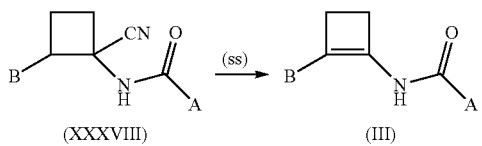

Scheme 8 provides methods for preparing compounds of the formula (III). Each of these methods form part of the invention.

Step (ss)

Compounds of the formula (III) can be prepared by treating compounds of the formula (XXXVIII), wherein A and B are as defined herein for a compound of the formula (I) with a base. Typical bases that can be used for this transformation are metal alkoxides, metal hydrides, and metal amides. Preferred bases are metal alkoxides, in particular sodium alkoxide, most particularly sodium t-butoxide. Compounds of the formula (XXXVIII) can be prepared by acylation of compounds of the formula (XXXVI) with an acylating agent of the formula (XXI), using methodology described above under step (i). The ratio of the cis- and trans-isomers of the compound of the formula (XXXVIII) does not matter in this step.

SCHEME 9

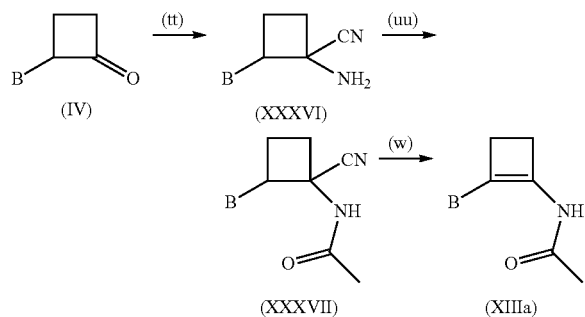

Scheme 9 provides method for preparing compounds of the formula (XXXVI), compounds of the formula (XXXVII) and compounds of the formula (XIIIa). Each of these methods form part of the invention.

Step (vv)

Compounds of the formula (XIIIa) can be prepared by treatment of compounds of the formula (XXXVII) with a base. Typical bases that can be used for this transformation are metal alkoxides, metal hydrides, and metal amides. Preferred bases are metal alkoxides, in particular sodium alkoxide, most particularly sodium t-butoxide. The ratio of the cis- and trans-isomers of the compound of the formula (XXXVII) does not matter in this step.

Step (uu)

Compounds of the formula (XXXVII) can be prepared by treatment of compounds of the formula (XXXVI) with an acetylating agent such as acetyl chloride or acetic anhydride. The ratio of the cis- and trans-isomers of the compound of the formula (XXXVI) does not matter in this step. A cis:trans mixture of the isomers of the compound of the formula (XXXVI) leads to a cis:trans mixture of isomers of the compound of the formula (XXXVII).

Step (tt)

Compounds of the formula (XXXVI) can be prepared by treating a compound of the formula (IV) with ammonia and cyanide. Ammonia and cyanide can be used in the form of their salts. An excess of acid can be advantageous.

For preparing all further compounds of the formula I functionalized according to the definitions of A, B, $R_1$ and $R_2$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

These reactions can be conveniently performed in a solvent.

These reactions can be conveniently performed at various temperatures.

These reactions can be conveniently performed in an inert atmosphere.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds of formula (I) are obtained by treatment with a suitable acid or a suitable ion exchanger reagent and salts with bases are obtained by treatment with a suitable base or with a suitable ion exchanger reagent. A salt is chosen depending on its tolerances for compound's use, such as agricultural or physiological tolerance.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties can be obtained in free form or in the form of salts.

Diastereomer mixtures or racemate mixtures of compounds of formula (I), in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

As has been discussed, substituents at R3, R4, R5, R6, R10, R11 and R12 may lead to other enantiomers and diastereomers being formed. These also form part of the invention.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615 or C. White, Science, vol 318, p. 783, 2007.

It can be advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the invention can be used for controlling or destroying pests such as insects and/or fungi which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests. The compounds of formula (I) according to the invention are preventively and/or curatively valuable active ingredients in the field of pest control, even at low rates of application, which can be used against pesticide resistant pests such as insects and fungi, which compounds of formula (I) have a very favorable biocidal spectrum and are well tolerated by warm-blooded species, fish and plants. Accordingly, the present invention also makes available a pesticidal composition comprising compounds of the invention, such as formula (I).

It has now been found that the compounds of formula I according to the invention have, for practical purposes, a very advantageous spectrum of activities for protecting animals and useful plants against attack and damage by nematodes. Accordingly, the present invention also makes available a nematicidal composition comprising compounds of the invention, such as formula (I).

It has also now been found that the compounds of formula I according to the invention have, for practical purposes, a very advantageous spectrum of activities for protecting animals and useful plants against attack and damage by fungi. Accordingly, the present invention also makes available a fungicidal composition comprising compounds of the invention, such as formula (I).

The compounds of formula (I) are especially useful for the control of nematodes. Thus, in a further aspect, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Glo-* bodera rostochiensis and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Particularly, the nematode species *Meloidogyne* spp., *Heterodera* spp., *Rotylenchus* spp. and *Pratylenchus* spp. can be controlled by compounds of the invention.

Generally, a compound of the present invention is used in the form of a composition (e.g. formulation) containing a carrier. A compound of the invention and compositions thereof can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

A formulation typically comprises a liquid or solid carrier and optionally one or more customary formulation auxiliaries, which may be solid or liquid auxiliaries, for example unepoxidized or epoxidized vegetable oils (for example epoxidized coconut oil, rapeseed oil or soya oil), antifoams, for example silicone oil, preservatives, clays, inorganic compounds, viscosity regulators, surfactant, binders and/or tackifiers. The composition may also further comprise a fertilizer, a micronutrient donor or other preparations which influence the growth of plants as well as comprising a combination containing the compound of the invention with one or more other biologically active agents, such as bactericides, fungicides, nematocides, plant activators, acaricides, and insecticides.

Accordingly, the present invention also makes available a composition comprising a compound of the invention and an agronomicaly carrier and optionally one or more customary formulation auxiliaries.

The compositions are prepared in a manner known per se, in the absence of auxiliaries for example by grinding, screening and/or compressing a solid compound of the present invention and in the presence of at least one auxiliary for example by intimately mixing and/or grinding the compound of the present invention with the auxiliary (auxiliaries). In the case of solid compounds of the invention, the grinding/milling of the compounds is to ensure specific particle size. These processes for the preparation of the compositions and the use of the compounds of the invention for the preparation of these compositions are also a subject of the invention.

Examples of compositions for use in agriculture are emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—a compound according to the invention and the type of composition is to be selected to suit the intended aims and the prevailing circumstances.

Examples of suitable liquid carriers are unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Examples of solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorptive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of compound according to the present invention and 1 to 99.9%, especially 5 to 99.9%, of at least one solid or liquid carrier, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion. Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. The compounds of the present invention are particularly suited for use in soil and seed treatment applications.

In general, the pre-mix compositions of the invention contain 0.5 to 99.9 especially 1 to 95, advantageously 1 to 50, %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

A compound of the formula (I) in a preferred embodiment, independent of any other embodiments, is in the form of a plant propagation material treating (or protecting) composition, wherein said plant propagation material protecting composition may comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

Examples of application methods for the compounds of the invention and compositions thereof, that is the methods of controlling pests in the agriculture, are spraying, atomizing, dusting, brushing on, dressing, scattering or pouring—which are to be selected to suit the intended aims of the prevailing circumstances.

One method of application in agriculture is application to the foliage of the plants (foliar application), it being possible to select frequency and rate of application to match the danger of infestation with the pest/fungi in question. Alternatively, the active ingredient can reach the plants via the root system (systemic action), by applying the compound to the locus of the plants, for example by application of a liquid composition of the compound into the soil (by drenching), or by applying a solid form of the compound in the form of granules to the soil (soil application). In the case of paddy rice plants, such granules can be metered into the flooded paddy-field. The application of the compounds of the present invention to the soil is a preferred application method.

Typical rates of application per hectare is generally 1 to 2000 g of active ingredient per hectare, in particular 10 to 1000 g/ha, preferably 10 to 600 g/ha, such as 50 to 300 g/ha.

The compounds of the invention and compositions thereof are also suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds. The application of the compounds of the present invention to seeds is a preferred application method.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula I, which is a preferred application method, can be carried out by any known methods, such as spraying or by dusting the seeds before sowing or during the sowing/planting of the seeds.

Suitable target plants are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, amd lawn grass or turf).

In an embodiment, the plant is selected from cereals, corn, soybean, rice, sugarcane, vegetables and oil plants.

The term "plant" is to be understood as including also plants which have been so transformed by the use of recombinant DNA techniques that they are capable of synthesising one or more selectively acting toxins, such as are known, for example, from toxin-producing bacteria, especially those of the genus *Bacillus* and also plants which have been selected or hybridised to preserve and/or attain a desired trait, such as insect, fungi and/or nematode resistance.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1 Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic plants are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Compounds of this invention are effective for controlling nematode, insect, acarid pests and/or fungal pathogens of agronomic plants, both growing and harvested, when employed alone, they may also be used in combination with other biological active agents used in agriculture, such as one or more nematicides, insecticides, acaricides, fungicides, bactericides, plant activator, molluscicide, and pheromones (whether chemical or biological). Mixing the compounds of the invention or the compositions thereof in the use form as pesticides with other pesticides frequently results in a broader pesticidal spectrum of action. For example, the formula (I) compounds of this invention may be used effectively in conjunction or combination with pyrethroids, neonicotinoids, macrolides, diamides, phosphates, carbamates, cyclodienes, formamidines, phenol tin compounds, chlorinated hydrocarbons, benzoylphenyl ureas, pyrroles and the like.

The activity of the compositions according to the invention can be broadened considerably, and adapted to prevailing circumstances, by adding, for example, one or more insecticidally, acaricidally, nematicidally and/or fungicidally active agents. The combinations compounds of formula (I) with other insecticidally, acaricidally, nematicidally and/or fungicidally active agents may also have further surprising advantages which can also be described, in a wider sense, as synergistic activity. For example, better tolerance by plants, reduced phytotoxicity, pests or fungi can be controlled in their different development stages or better behaviour during their production, for example during grinding or mixing, during their storage or during their use.

The following list of pesticides together with which the compounds according to the invention can be used, is intended to illustrate the possible combinations by way of example.

The following combination of the compounds of formula (I) with another active compounds are preferred (the abbreviation "TX" means a compound of the formula I, preferably a compound selected from the compounds described in Tables 1 to 56 shown above and, more preferably, Tables 60 and 61 shown below, even more preferably a compound selected from 60.1, 60.2, 60.3, 60.4, 60.5, 60.6, 60.7, 60.8, 60.9, 60.10, 60.11, 60.12, 60.13, 60.14, 60.15, 60.16, 60.18, 60.19, 60.20, 60.21, 60.22, 60.23, 60.24, 60.26, 60.27, 60.28, 60.29, 60.30, 60.31, 60.32, 60.33, 60.34, 60.35, 60.37, 60.38, 60.39, 60.40, 60.42, 60.43, 60.44, 60.45, 60.46, 60.47, 60.48, 60.49, 60.50, 60.51, 60.52, 60.53, 60.54, 60.55, 60.56, 60.57, 60.58, 60.59, 60.60, 60.61, 60.62, 60.63, 60.64, 60.65, 60.66, 60.67, 60.68, 60.69, 60.70, 60.71, 60.72, 60.73, 60.74, 60.75, 60.78, 60.79, 60.86, 60.88, 60.89, 60.90, 60.93, 60.94, 60.95, 60.96, 60.97, 60.98, 60.103, 60.104, 60.105, 60.106, 60.107, 60.108, 60.109, 60.110, 60.111, 60.112, 60.113, 60.114, 60.116, 60.122, 60.123, 60.125, 60.126, 60.127, 60.128, 60.129, 60.130, 60.131, 60.132, 60.133, 60.134, 60.135, 60.136, 60.137, 60.138, 60.139, 60.140, 60.142, 60.143, 60.144, 60.146, 60.148, 60.149, 60.151, 60.155, 60.163, 60.165, 60.166, 60.167, 60.168, 60.169, 60.171, 60.172, 60.176, 60.177, 60.178, 60.179, 60.180, 60.181, 60.182, 60.183, 60.184, 60.185, 60.186, 60.187, 60.188, 60.190, 60.191, 60.192, 60.193, 60.194, 60.195, 60.199, 60.203, 60.204, 60.214, 60.219, 60.229, 60.233, 60.234, 60.235, 60.236, 60.237, 60.238, 60.239, 60.240, 60.241, 60.242, 60.243, 60.244, 60.245, 60.246, 61.1, 61.2, 61.3, 61.4, 61.5, 61.6, 61.7, 61.8, 61.9, 61.10, 61.11, 61.14, 61.15, 61.16, 61.17, 61.18, 61.20, 61.21, 61.22, 61.23, 61.24, 61.25, 61.26, 61.32, 61.36, 61.38, 61.41, 61.44, 61.46, 61.47, 61.48, 61.49, 61.52, 61.53, 61.54, 61.55, 61.56, 61.58, 61.59, 61.60, 61.62, 61.64, 61.65, 61.66, 61.67, 61.68, 61.69, 61.70, 61.72, 61.73, 61.74, 61.76, 61.77, 61.79, 61.81, 61.83, 61.84, 61.85, 61.86, 61.87, 61.88, 61.89, 61.90, 61.91, 61.92, 61.93, 61.95, 61.96, 61.97, 61.98, 61.99, 61.100, 61.101, 61.102, 61.103, 61.104, 61.106, 61.108, 61.109, 61.110, 61.113, 61.114, 61.116, 61.117, 61.118, 61.119, 61.121, 61.122, 61.124, 61.125, 61.126, 61.127, 61.129, 61.131, 61.133, 61.136, 61.137, 61.140, 61.141, 61.143, 61.144, 61.146, 61.151, 61.154, 61.155, 61.156, 61.158, 61.159, 61.162, 61.167, 61.172, 61.173, 61.174, 61.175 and 61.176):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, bromfenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (995)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (485)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1395)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (495)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of Adoxophyes orana GV (alternative name) (12)+TX, Agrobacterium radiobacter (alternative name) (13)+TX, Amblyseius spp. (alternative name) (19)+TX, Anagrapha falcifera NPV (alternative name) (28)+TX, Anagrus atomus (alternative name) (29)+TX, Aphelinus abdominalis (alternative name) (33)+TX, Aphidius colemani (alternative name) (34)+TX, Aphidoletes aphidimyza (alternative name) (35)+TX, Autographa californica NPV (alternative name) (38)+TX, Bacillus firmus (alternative name) (48)+TX, Bacillus sphaericus Neide (scientific name) (49)+TX, Bacillus thuringiensis Berliner (scientific name) (51)+TX, Bacillus thuringiensis subsp. aizawai (scientific name) (51)+TX, Bacillus thuringiensis subsp. israelensis (scientific name) (51)+TX, Bacillus thuringiensis subsp. japonensis (scientific name) (51)+TX, Bacillus thuringiensis subsp. kurstaki (scientific name) (51)+TX, Bacillus thuringiensis subsp. tenebrionis (scientific name) (51)+TX, Beauveria bassiana (alternative name) (53)+TX, Beauveria brongniartii (alternative name) (54)+TX, Chrysoperla carnea (alternative name) (151)+TX, Cryptolaemus montrouzieri (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Pasteuria penetrans*+TX, *Pasteuria thornei*+TX, *Pasteuria nishizawae*+TX, *Pasteuria Ramosa*+TX, *Phytoseiulus Persimilis* (Alternative Name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl) aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alphaecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, Bacillus thuringiensis delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (III)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name)

(473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, tefluben-zuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-

40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, fluopyram+TX, Imcyafos+TX, Tioxazafen+TX, 2-Chloro-N-(8-chloro-6-trifluoromethyl-imidazo[1,2-a]pyridine-2-carbonyl)-5-methoxy-benzenesulfonamide+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-

9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-C1-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-C1-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid [2-(2,4-dichlorophenyl)-2-methoxy-1-methyl-ethyl]-amide (disclosed in WO 2008/148570)+TX, 1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone+TX, 1-[4-[4-[5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone [1003318-67-9], both disclosed in WO 2010/123791, WO 2008/013925, WO 2008/013622 and WO 2011/051243 page 20)+TX, and 3-difluoromethyl-1-methyl-1H-pyrazole-4-carboxylic acid (3',4',5'-trifluoro-biphenyl-2-yl)-amide (disclosed in WO 2006/087343)+TX.

The references in square brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address: http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The mass ratio of of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:1 to 1:100, including from 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5, for example 1:3 to 3:1. The mixing ratios are understood to include, on the one hand, ratios by mass and also, on other hand, molar ratios.

The combinations of the present invention (i.e. those comprising a compound of the present invention and one or more other biological active agents) may be applied simultaneously or sequentially.

In the event, the ingredients of a combination are applied sequentially (i.e., one after the other), the ingredients are applied sequentially within a reasonable period of each other to attain the biological performance, such as within a few hours or days. The order of applying the ingredients in the combination, i.e., whether the compounds of formula (I) should be applied first or not is not essential for working the present invention.

In the event ingredients of the combinations are applied simultaneously in the present invention, they may be applied as a composition containing the combination, in which case (A) the compound of formula (I) and the one or more other ingredients in the combinations can be obtained from separate formulation sources and mixed together (known as a tank-mix, ready-to-apply, spray broth, or slurry), or (B) the compound of formula (I) and the one or more other ingredients can be obtained as single formulation mixture source (known as a pre-mix,ready-mix, concentrate, or formulated product).

In an embodiment, independent of other embodiments, a compound according to the present invention is applied as a combination. Accordingly, the present invention also provides a composition comprising a a compound according the invention as herein described and one or more other biological active agents, and optionally one or more customary formulation auxiliaries; which may be in the form of a tank-mix or pre-mix composition.

The compounds of formula I are particularly useful for controlling and preventing helminth and nemtode endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of invention are especially useful for the control of helminths and nematodes. Examples for helminths are members of the class Trematoda, commonly known as flukes or flatworms, especially members of the genera *Fasciola, Fascioloides, Paramphistomu, Dicrocoelium, Eurytrema, Ophisthorchis, Fasciolopsis, Echinostoma* and *Paragonimus*. Nematodes which can be controlled by the formula (I) compounds include the genera *Haemonchus, Ostertagia, Cooperia, Oesphagastomu, Nematodirus, Dictyocaulus, Trichuris, Dirofilaria, Ancyclostoma, Ascaria* and the like.

For oral administration to warm-blooded animals, the compounds of the invention may be formulated as animal feeds, animal feed premixes, animal feed concentrates, pills, solutions, pastes, suspensions, drenches, gels, tablets, boluses and capsules. In addition, the compounds of the invention may be administered to the animals in their drinking water. For oral administration, the dosage form chosen should provide the animal with about 0.01 mg/kg to 100 g/kg of animal body weight per day of the compound of the invention.

Alternatively, the compounds of the invention may be administered to animals parenterally, for example, by intraruminal, intramuscular, intravenous or subcutaneous injection. The compounds of the invention may be dispersed or dissolved in a physiologically acceptable carrier for subcutaneous injection. Alternatively, the compounds of the invention may be formulated into an implant for subcutaneous administration. In addition the compounds of the invention may be transdermally administered to animals. For parenteral administration, the dosage form chosen should provide the animal with about 0.01 mg/kg to 100 mg/kg of animal body weight per day of the compound of the invention.

The compounds of the invention may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the compound of the invention. In addition, the compounds of the invention may be formulated as ear tags for animals, particularly quadrupeds such as cattle and sheep.

In an embodiment, independent of any other embodiments, a compound of formula (I) is a anti-helminth compound.

In an embodiment, independent of any other embodiments, a compound of formula (I) is a pesticidal compound, preferably a nematicidal compound.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples serve to illustrate the invention. They do not limit the invention. Temperatures are given in degrees Celsius; mixing ratios of solvents are given in parts by volume.

FIGURES

FIG. 1. Structure of Example P17 with non-hydrogen atoms shown as thermal ellipsoids at the 50% probability level.

Figure 2:
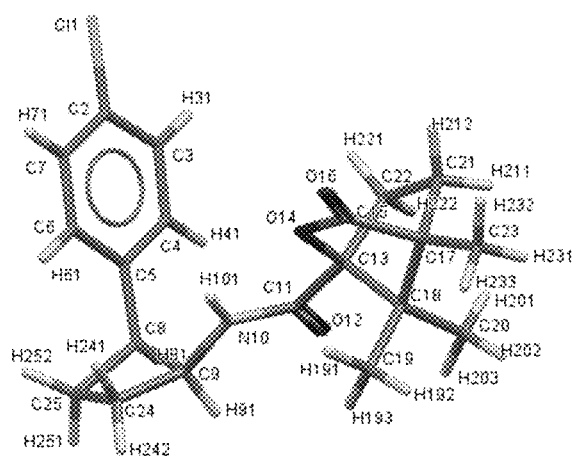

FIG. 2. Numbering scheme for Example P17.

EXAMPLES

Preparation Examples

Example P1

Preparation of racemic N-[cis-2-(4-chlorophenyl)oxetan-3-yl]-2-(trifluoromethyl)benzamide

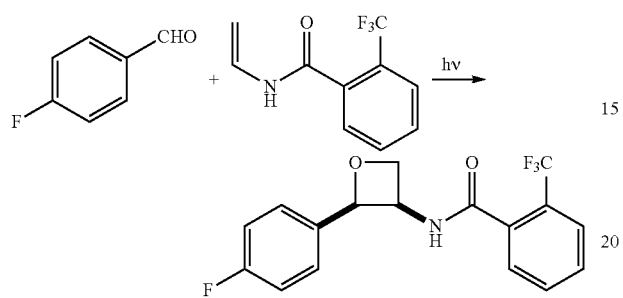

A solution of 4-fluorobenzaldehyde (288 mg, 2.32 mmol) and 2-trifluoromethyl-N-vinyl-benzamide (1 g, 4.65 mmol) in acetonitrile (15 ml) was irradiated with a sodium vapour lamp through a quartz filter for 7 days. The cloudy reaction mixture was evaporated down and the crude half-solid (1.6 g) was chromatographed on silica with EtOAc/cyclohexane, then again with MeOH/dichloromethane and again with EtOAc/cyclohexane to yield N-[cis-2-(4-chlorophenyl)oxetan-3-yl]-2-(trifluoromethyl)benzamide.

1H-NMR (CDCl3) 4.51 (1H, t); 5.17 (1H, t); 5.48 (1H, M); 5.71 (1H, br d); 6.08 (1H, d); 6.93 (1H, d); 7.12 (2H, t); 7.38 (2H, m); 7.47 (2H, m); 7.63 (1H, d).

Example P1 b

Preparation of 2-trifluoromethyl-N-vinyl-benzamide n-Propylamine (4.8 g, 82 mmol) was added to a solution of 10 g of the mixture of 2-trifluoromethyl-N-vinyl-N-formyl-benzamide (example P1c) and 2-trifluoromethyl-N-vinyl-benzamide (10 g, 41 mmol) in dichloromethane (50 ml). There was an exotherm, which was controlled by the use of a cold water bath. After one hour tlc (70% EtOAc/hexane) showed complete reaction so the mixture was separated between water and EtOAc, dried (MgSO$_4$) and evaporated to yield 11 g of a brown oil which contained nPrNH2 according to NMR. This was dissolved in ethanol (ca 30 ml), warmed to 50° C., treated with water and allowed to cool. The crystals were then filtered off and dried to yield 2-trifluoromethyl-N-vinyl-benzamide as beige crystals. m.p. 92-95° C.

1H-NMR (CDCl$_3$) 4.57 (1H, d); 4.72 (1H, d), 7.10 (1H, ddd); 7.44 (1H, br s); 7.60 (3H, m); 7.73 (1H, d).

Example P1c

Preparation of 2-trifluoromethyl-N-vinyl-N-formyl-benzamide

2-Trifluoromethyl-benzoyl chloride (32 g, 154 mmol) was added in portions to a stirred solution of N-vinylformamide (10 ml, 10 g, 140 mmol), 4-dimethylaminopyridine (1.7 g, 14 mmol), and triethylamine (29.2 ml, 21.2 g, 210 mmol) in dichloromethane in an ice/water bath at such a rate that the temperature stayed below 25° C. After complete addition the mixture was allowed to warm to room temperature. After two hours the mixture was separated between water and EtOAc, the organic phase dried and evaporated to give a brown oil. NMR showed a ca 1:1 mixture of 2-trifluoromethyl-N-vinyl-N-formyl-benzamide and 2-trifluoromethyl-N-vinyl-benzamide.

1H-NMR (CDCl3, signals given for 2-trifluoromethyl-N-vinyl-N-formyl-benzamide) 5.26 (1H, d); 5.72 (1H, d); 6.69 (1H, dd); 7.43 1H, d); 7.58 (1H, m); 7.68 (1H, m); 7.80 (1H, d); 8.87 (1H, s).

Example P2

Preparation of racemic cis N-[2-(4-chlorophenyl)cyclobutyl]-2-(trifluoromethyl)benzamide

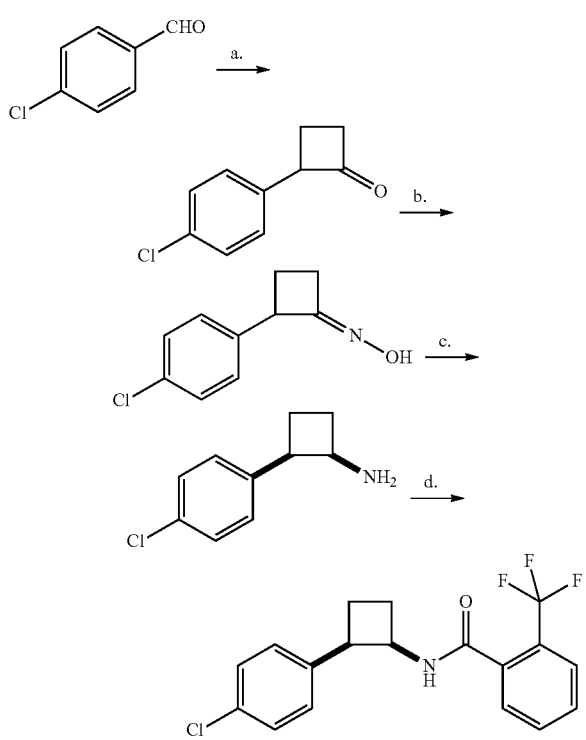

a. Preparation of 2-(4-chlorophenyl)cyclobutanone

To a stirred solution of 4-chloro-benzaldehyde (142 mg, 1 mmol) and cyclopropyldiphenylsulfonium tetrafluoroborate (317 mg, 1 mmol) in 10 ml dry THF, cooled to 0° C., was added dropwise, with stirring, a slurry of potassium tert. butoxide (1.4 ml; 1M). After addition was complete the reaction was stirred 30 min. and 1M tetrafluoroboric acid (10% in THF) (10 ml) was added. The mixture was allowed to warm to room temperature and was taken up into ether and the ether solution was washed with saturated NaHCO$_3$, brine and water and was dried. Filtration and concentration by rotary evaporation gave an oil. Chromatography over silica gel and elution with hexanes:ether 5:1 gave 2-(4-chlorophenyl)cyclobutanone as an oil 1H-NMR (CDCl$_3$) 2.20 (1H, m); 2.57 (1H, m); 3.06 (1H, m); 3.23 (1H, m); 4.51 (1H, m); 7.20 (2H, m); 7.29 (3H, m);

b. Preparation of 2-(4-chlorophenyl)cyclobutanone oxime

A solution of 2-(4-chlorophenyl)cyclobutanone (1.122 g, 6.09 mmol), hydroxylamine hydrochloride (3.541 g. 8.2 eq.) and 36 ml of 5% NaOH in 30 ml EtOH was heated at reflux for 2 h. The solution was cooled, adjusted to pH 6, and extracted with $CHCl_3$. The organic extract was washed with brine and dried. Filtration and concentration yielded 2-(4-chlorophenyl)cyclobutanone oxime as an oil. 1H-NMR ($CDCl_3$) 2.13 (1H, m); 2.53 (1H, m); 3.01 (2H, m); 4.40 (1H, m); 7.27 (5H, m);

c. Preparation of 2-(4-chlorophenyl)cyclobutanamine

To a solution of 2-(4-chlorophenyl)cyclobutanone oxime (200 mg, 1 mmol) in methanol (5 ml) was added $MoO_3$ (205 mg, 1.4 eq.) and sodium borohydride (394 mg, 10 eq) at 0° C. After stirring at rt for 2 h the solvent was evaporated. A mixture of $H_2O$ and $CH_2Cl_2$ was added. Organic phase was separated, washed with brine, dried and concentrated in vacuo. 120 mg of product-amine was isolated as a mixture of cis and trans isomers 2:1. The crude product was used without purification in the next reaction.

d. Preparation of N-[2-(4-chlorophenyl)cyclobutyl]-2-(trifluoromethyl)benzamide To a solution of 2-(4-chlorophenyl)cyclobutanamine (105 mg, 0.55 mmol) and triethylamine (140 mg 2.5 eq.) in THF was added 2-trifluoromethyl-benzoylchloride (127.46 mg, 1.1 eq.) at 0° C. The reaction mixture was stirred at rt for 2 h. $Et_3N.HCl$ was filtered off and the THF was evaporated. The residue-mixture of two isomers cis and trans (2:1) was purified and separated with chromatography on silica gel, eluent hexanes:diethylether 1:1, N-[cis-2-(4-chlorophenyl)cyclobutyl]-2-(trifluoromethyl)benzamide (cis) (m.p. 147-9° C.) and its trans isomer (m.p. 117-9° C.) were isolated as crystalline products.

Example P3

Preparation of 2-(4-chlorophenyl)cyclobutanone (alternative)

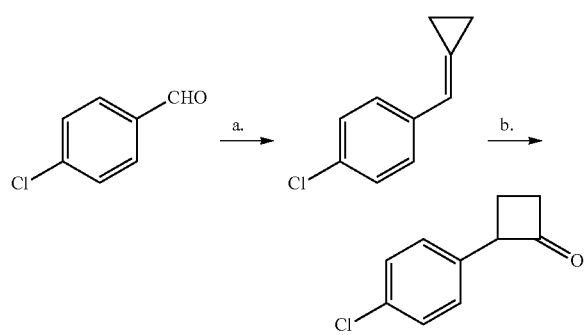

a. Preparation of 1-chloro-4-(cyclopropylidenemethyl)benzene

To a suspension of (3-bromopropyl)triphenylphosphonium bromide (29.3 g) in anhydrous THF (200 ml) was added in 5 separate portions 15 mins apart potassium tert. butoxide (14.19 g, 2.2 eq.) to give a yellow suspension. The mixture was heated to reflux for 10 min and 4-chlorobenzaldehyde (8.08 g, 56.9 mmol) was added to give an orange suspension. The reaction mixture was stirred and then heated at reflux for 4 h. The reaction mixture was then cooled to room temperature, and filtered through a Celite pad. The solvent was removed in vacuo, and the resulting crude material was subjected to flash chromatography with i-hexane as an eluent, affording 1-chloro-4-(cyclopropylidenemethyl)benzene.

1H-NMR ($CDCl_3$) 1.19 (2H, m); 1.41 (2H, m); 6.70 (1H, m); 7.27 (2H, m); 7.46 (2H, m)

b. Preparation of 2-(4-chlorophenyl)cyclobutanone

To a solution of 1-chloro-4-(cyclopropylidenemethyl)benzene (5 g, 30 mmol) in $CH_2Cl_2$ (80 ml) was added in 5 separate portions m-chloroperbenzoic acid (5.3 g, 30 mmol) at 0° C. After stirring at 0° C. for 3 h, the reaction mixture was washed with saturated $NaHCO_3$ aqueous solution and brine, dried over $Na_2SO_4$ and concentrated. To the crude product in $CH_2Cl_2$ (40 ml) was added a 10% $HBF_4$ (11.6 ml 48% $HBF_4$ and 46 ml $H_2O$). After stirring at rt for 17 h, the mixture was extracted with $CH_2Cl_2$, washed with saturated $NaHCO_3$ aq. solution and brine. The solvent was removed in vacuo, and the residue was purified by column chromatography on silica gel (eluent i-hexane) to give 2-(4-chlorophenyl)cyclobutanone.

Example P4

Preparation of N-[2-(4-chlorophenyl)cyclobuten-1-yl]-2-(trifluoromethyl)benzamide

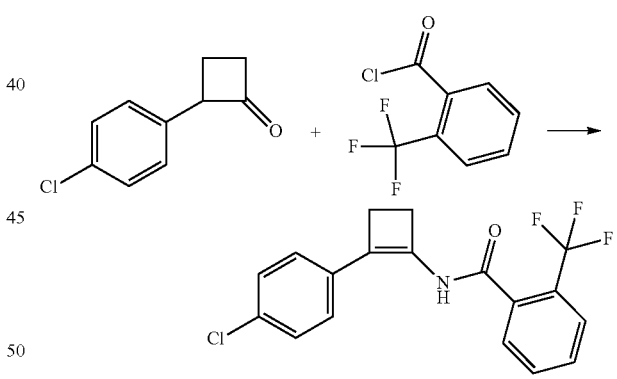

2-(4-chlorophenyl)cyclobutanone (10 g) was dissolved in 50 ml toluene. The solution was cooled to 0° C. and ammonia in methanol (11.863 ml; 7M) and titanium isopropoxide (34.6 ml, 32.442 g) were added. The mixture was warmed to rt and stirred for 18 h, then cooled to 0° C. and triethylamine (31.2 ml, 22.6343 g) and 2-trifluoromethyl-benzoyl chloride (16.47 ml, 23.3259 g) were added subsequently. During the addition of the acid chloride a thick suspension was formed, so that toluene (ca. 50 ml) were added to get the reaction mixture more stirrable. After 2 hours stirring at RT, a solution of ethylene diamine-N,N,N', N'-tetra-2-ethanol (33.3 ml, 34.3390 g) in a little toluene was added to the reaction mixture. The mixture was stirred at 60° C. (oil bath) for 15 min, cooled to rt and shaken between water (300 ml), ammonia solution (50 ml) and ethyl acetate.

The organic phase was washed with water then brine, dried with Na2SO4, evaporated and the crude material stirred with 100 ml diethyl ether. The solid was filtered off and dried to yield 9.2 g of impure product. The mother liquors were chromatographed with EtOAc/hexane to yield 1.4 g of impure product. The two crude fractions were combined and chromatographed again to yield pure N-[2-(4-chlorophenyl) cyclobuten-1-yl]-2-(trifluoromethyl)benzamide m.p. 165-8° C., 1H-NMR (CDCl3) 2.62 (2H, m); 3.16 (2H, m); 7.08 (2H, d), 7.27 (2H, d); 7.51 (1H, br s, NH); 7.61 (1H, m); 7.64 (2H, m), 7.76 (1H, d).

Example P5

Preparation of N-[(1S,2S)-2-(2,4-dichlorophenyl) cyclobutyl]-2-(trifluoromethyl)pyridine-3-carboxamide

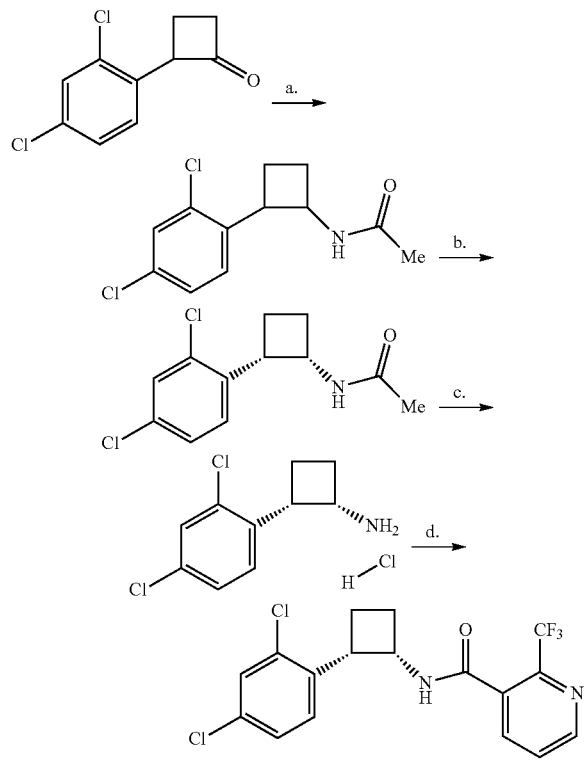

a. Preparation of N-[2-(4-chlorophenyl)cyclobuten-1-yl]-acetamide 2-(2,4-dichlorophenyl)cyclobutanone (100 g) was dissolved in toluene (280 ml) under argon at 0° C., and ammonia in methanol (99.6 ml; 7M) in methanol was added dropwise. No exotherm was observed. Titanium isopropoxide (291 ml, 272 g) was added dropwise (ca. over 1.5 h). An exotherm was observed, and so the internal temperature was held between 0 and 5° C. with an ice bath. The mixture was warmed to rt and stirred for 17 h. The mixture was cooled to 0° C. and triethylamine (262 ml, 190 g) was added over ca. 20 min followed by acetic anhydride (88.70 ml, 95.9 g). An exotherm was observed. The internal temperature was held between 0 and 5° C. then warmed to rt and stirred for 3 h. Ethylene diamine-N,N,N',N'-tetra-2-ethanol (206 ml, 233 g) was added to the reaction mixture. The mixture was heated to 55° C. internal for 15 min, then cooled to rt. The mixture was shaken between water, ammonia solution and EtOAc. The aqueous phase was washed with tBuOMe, and the organic phases combined, dried over MgSO4 and the solvent was evaporated to give a oily brown solid. This crude was triturated with ethyl acetate (ca. 1 h), then isolated via suction, washed with TBME and dried via suction. The mother liquor was placed in the fridge over the weekend and a precipitation was observed. The solid was isolated via suction, washed with cyclohexane and dried in air. To give combined solids of good purity. The mother liquor was concentrated and chromatographed with EtOAc/hexane to yield nearly pure material, which was triturated with cyclohexane and the solids filtered off and washed with cyclohexane to yield pure product 1H-NMR (CDCl3) 2.06 (3H, s, Me); 2.65 (2H, m); 3.06 (2H, m); 7.12 (1H, d); 7.19 (1H, d); 7.32 (1H, s); 7.58 (1H, br, s, NH).

b. Preparation of N-[(1S,2S)-2-(2,4-dichlorophenyl) cyclobutyl]acetamide

N-[2-(2,4-dichlorophenyl)cyclobuten-1-yl]acetamide (25 g) and dimethylammonium dichlorotri(mu-chloro)bis[(s)-(+ 2,2'-bis(diphenylphosphino)-1,1'-binaphthyl]diruthenate(II) (0.4078 g) were placed in an autoclave (vertex hpm) and methanol (250 ml) was added. The methanol was previously purged for 30 min with argon. It was purged with argon 3 times, then with hydrogen 3 times and an internal pressure of hydrogen of 50 bar was built up. The reaction mixture was stirred over 18 h at 45° C. After 18 h the autoclave was opened and the solvent was evaporated to give the crude (26.17 g) as a grey oil. This was chromatographed with ethyl acetate and cyclohexane to yield almost pure product. It was analyzed by chiral HPLC (method X) and showed an ee of 87% in favour of the desired enantiomer eluting at 9.59 min (minor enantiomer eluting at 8.11 min). This was combined with material from an analogous hydrogenation batch of N-[2-(4-chlorophenyl)cyclobuten-1-yl]acetamide, and recrystallized from ethyl acetate and cyclohexane to yield pure product with 98% ee.

1H-NMR (CDCl3) 1.76 (s, 3H, Me); 1.94 (1H, m); 2.26 (2H, m); 2.49 (1H, m); 4.14 (1H, m); 4.92 (1H, m), 4.99 (1H, br s, NH); 7.32 (m, 2H); 7.42 (1H, s).

c. Preparation of N-(1S,2S)-2-(2,4-dichlorophenyl)cyclobutylamine hydrochloride

N-[(1S,2S)-2-(2,4-dichlorophenyl)cyclobutyl]acetamide (15.7 mmol, 4.04 g, ee=91%) was diluted in methanol (15 ml). hydrochloric acid 36% (157 mmol, 18.6 g, 15.7 ml) was then added drop-wise. The reaction mixture was stirred at reflux overnight (20 hours). Methanol was evaporated, then some TBME and water were added to the mixture. Both phases were separated and the aqueous phase was washed twice with TBME. The aqueous phase was mixed with TBME cooled down to 0° C. whereupon sodium hydroxide 30% solution (16 ml) was slowly added until the pH became basic. Both phases were separated again and the aqueous phase was extracted twice with TBME. Organic layers were combined, dried with anhydrous sodium sulfate, filtered and concentrated to give an orange oil.

The amine was diluted in diethyl ether and cooled down to 0° C. whereupon aqueous HCl (1M) in diethyl ether was added drop-wise. A solid precipitated. This solid was isolated by filtration, washing with diethyl ether and drying on high vacuum pump to afford a white powder. It was analysed via chiral HPLC (method Y) which showed an ee of 88% in favour of the desired enantiomer eluting at 7.85 min (minor enantiomer eluting at 5.08 min).

1H-NMR (CDCl3) 1.50 (1H, m); 2.26 (1H, m); 2.45 (1H, m); 2.91 (1H, m); 3.99 (2H, m); 7.22 (1H, d); 7.38 (2H, m); 8.03 (3H, br s, NH3+)

d. Preparation of N-[(1S,2S)-2-(2,4-dichlorophenyl) cyclobutyl]-2-(trifluoromethyl)pyridine-3-carboxamide N-(1S,2S)-2-(2,4-dichlorophenyl)cyclobutylamine hydrochloride (9.6 g, 38 mmol) was dissolved in 100 ml DMF, N-hydroxy-benztriazole. hydrate (11 g, 76 mmol), EDCl hydrochloride (15 g, 76 mmol), and 2-trifluoromethylnicotinic acid (8.7 g, 46 mmol) were added. Triethylamine (12 g, 110 mmol) was added to give a weak exotherm, and a slight suspension. It was stirred overnight at RT. The mixture was shaken between ether and water, washed with brine, dried with Na2SO4, and evaporated. The crude was stirred with hexane and the crystals filtered off, washed with hexane, and dried in vacuo to yield pure product. It was analyzed via chiral HPLC (method C) which showed an ee of 99.7% in favour of the desired enantiomer eluting at 4.81 min (minor enantiomer eluting at 9.32 min).

m.p. 122-124° C.

1H-NMR (CDCl3) 2.07 (1H, m); 2.38 (2H, m); 2.12 (1H, m); 2.62 (1H, m); 4.26 (m, 1H); 5.05 (1H, m); 5.45 (1H, br d, NH); 7.28 (3H, m); 7.48 (1H, dd); 7.63 (1H, d); 8.68 (1H, d).

Example P6

Preparation of N-[(1S,2S)-2-(2,4-difluorophenyl) cyclobutyl]formamide

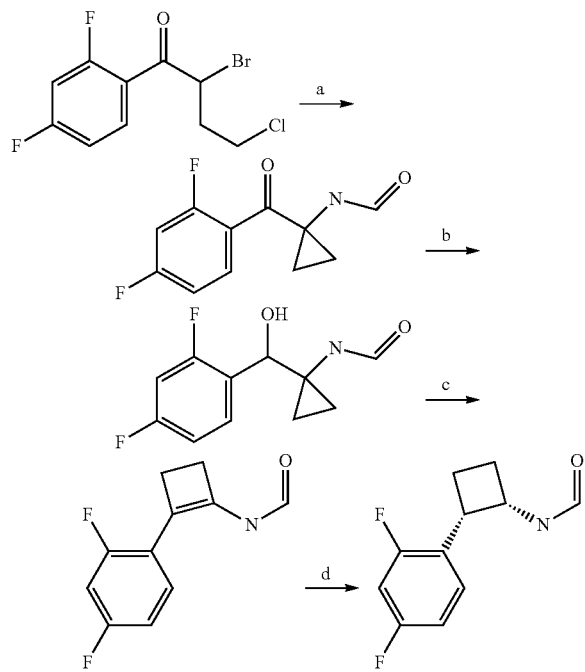

a. Preparation of N-[1-(2,4-difluorobenzoyl)cyclopropyl]formamide

2-Bromo-4-chloro-1-(2,4-difluorophenyl)butan-1-one (5 g) was dissolved in acetonitrile (16 ml) and dimethylformamide (0.84 ml). To this solution was added, at room temperature, (diformylamino)sodium (4 g), and the resulting beige suspension was heated under stirring at 60° C. for 6.5 hours. The reaction mixture was allowed to cool down to room temperature, and aqueous sodium hydroxide solution (16.8 ml; 2N) was then added. The biphasic mixture was then stirred for 15 minutes, before being poured into a separatory funnel containing aqueous hydrochloric acid solution (50 ml; 1N). The aqueous phase was separated and extracted twice with ethyl acetate (100 ml then 50 ml). The organic phase was extracted four times with water and once with brine, before the organic phases were combined and dried with solid sodium sulfate, filtered and concentrated under vacuum. N-[1-(2,4-difluorobenzoyl)-cyclopropyl]formamide was obtained as a brownish solid.

$^1$H NMR (400 MHz, CDCl3) δ ppm Minor rotamer: 8.13 (dd, J=11.74, 2.20 Hz, 1H), 7.53-7.49 (m, 1H), 6.99 (td, J=8.44, 2.20 Hz, 1H), 6.93-6.85 (m, 1H), 6.46 (bs, 1H), 1.90-1.83 (m, 2H), 1.42-1.38 (m, 2H).

Major rotamer: 7.96 (s, 1H), 7.59-7.51 (m, 1H), 6.95 (td, J=8.44, 2.20 Hz, 1H), 6.86-6.80 (m, 1H), 6.52 (bs, 1H), 1.90-1.84 (m, 2 H), 1.31-1.27 (m, 2 H).

b. Preparation of N-[1-[(2,4-difluorophenyl)-hydroxy-methyl]cyclopropyl]formamide N-[1-(2,4-Difluorobenzoyl)-cyclopropyl]formamide (1.79 g) was dissolved in ethanol (40 ml) and the solution was cooled down to 0° C. Sodium borohydride (150 mg) was added to the resulting solution in one portion. After 15 min stirring at 0° C., the reaction mixture was allowed to warm to room temperature and stirred for half an hour more. It was then cooled down to 0° C. and aqueous saturated ammonium chloride solution (12 ml) was added slowly. The mixture was then diluted with ethyl acetate and poured onto water. The phases were separated and the aqueous phase was extracted twice with ethyl acetate. The combined organic phases were washed with water, then brine, before being dried on solid sodium sulfate, filtered and concentrated under vacuum. The desired product N-[1-[(2,4-difluorophenyl)-hydroxy-methyl]cyclopropyl]formamide was obtained as a pale yellow oil.

$^1$H NMR (400 MHz, CDCL3) δ ppm

Minor rotamer: 7.86 (d, J=11.7 Hz, 1H), 7.52-7.44 (m, 1H), 6.94-6.85 (m, 1H), 6.83-6.77 (m, 1H), 6.18 (bs, 1H), 4.59 (d, J=2.6 Hz, 1H), 3.41 (d, J=3.3 Hz, 1H), 1.1-0.7 (m, 4H)

Major rotamer: 7.97 (s, 1H), 7.54-7.46 (m, 1H), 6.94-6.85 (m, 1H), 6.80-6.74 (m, 1H), 6.21 (bs, 1H), 5.36 (d, J=5.5 Hz, 1H), 4.55 (d, J=5.5 Hz, 1H), 1.1-0.7 (m, 4H)

c. Preparation of N-[(2-(2,4-difluorophenyl)cy-clobuten-1-yl]formamide

To a solution of N-[1-[(2,4-difluorophenyl)-hydroxymethyl]cyclopropyl]formamide (498 mg) in toluene (8.7 ml) was added sulfur trioxide pyridine complex (Py.SO3) (523 mg; 45% SO3). The resulting suspension was heated at 80° C. for 4 hours, before being diluted with ethyl acetate and added onto a saturated aqueous solution of sodium bicarbonate. The phases were separated and the aqueous phase was extracted twice with ethyl acetate. The organic phase was washed with a saturated aqueous solution of sodium bicarbonate, then with brine, the combined organic phases were then dried over solid sodium sulfate, filtered and concentrated under vacuum. N-[2-(2,4-difluorophenyl)cyclobuten-1-yl]formamide was obtained as a solid. ¹H NMR (400 MHz, CDCl3) δ ppm Major isomer: 8.39 (dd, J=11.37, 4.40 Hz, 1H), 7.88 (bs, 1H), 7.13-7.07 (m, 1H), 6.90-6.79 (m, 2H), 2.83-2.79 (m, 2H), 2.67-2.63 (m, 2H). Minor isomer: 8.22 (s, 1H), 7.73 (bs, 1H), 7.15-7.09 (m, 1H), 6.90-6.79 (m, 2H), 3.13-3.10 (m, 2H), 2.63-2.59 (m, 2H).

d. Preparation of N-[(1S,2S)-2-(2,4-difluorophenyl)cyclobutyl]formamide

Bis(1,5-cyclooctadiene)rhodium(I) trifluoromethanesulfonate (4.5 mg) and (R)-1-[(S$_P$)-2-(Di-tert-butylphosphino)ferrocenyl]ethylbis(2-methylphenyl)phosphine (5.4 mg) were dissolved in degassed 2,2,2-trifluoroethanol (4 mL) and the resulting catalyst solution was stirred for 30 min at room temperature under argon. Then, 2 mL of the catalysts solution and 3 mL degassed 2,2,2-trifluoroethanol were transferred via syringe into a 100 ml stainless steel reactor containing N-[2-(2,4-difluorophenyl)cyclobuten-1-yl]formamide (100 mg) set under an atmosphere of argon. The reactor was purged 3 times with hydrogen (10 bar) and finally pressurized to 50 bar. The reaction mixture was stirred under 50 bars of hydrogen at 50° C. After 18 h the autoclave was vented. The crude reaction mixture was filtrated over a pad of celite and evaporated giving N-[(1S,2S)-2-(2,4-difluorophenyl)cyclobutyl]formamide as an oil.

Chiral GC analysis (method AA), retention time 11.91 minutes (major enantiomer 93.7%) and 12.19 minutes (minor enantiomer 6.3%))

Major rotamer: ¹H NMR (400 MHz, CDCl₃): δ=2.00-2.08 (m, 1H), 2.27-2.35 (m, 2H), 2.48-2.65 (m, 1H), 4.03-4.14 (m, 1H), 4.88-4.96 (q, 1H), 5.29 (bs, 1H), 6.80-6.95 (m, 2H), 7.21-7.32 (m, 1H), 7.94 (s, 1H).

Minor rotamer: ¹H NMR (400 MHz, CDCl₃): δ=2.00-2.08 (m, 1H), 2.27-2.35 (m, 2H), 2.48-2.65 (m, 1H), 4.03-4.14 (m, 1H), 4.40-4.49 (q, 1H), 5.40 (bs, 1H), 6.80-6.95 (m, 2H), 7.21-7.32 (m, 1H), 7.95-7.98 (d, 1H).

Example P7

Preparation of N-[(2-(2,4-difluorophenyl)cyclobuten-1-yl]acetamide

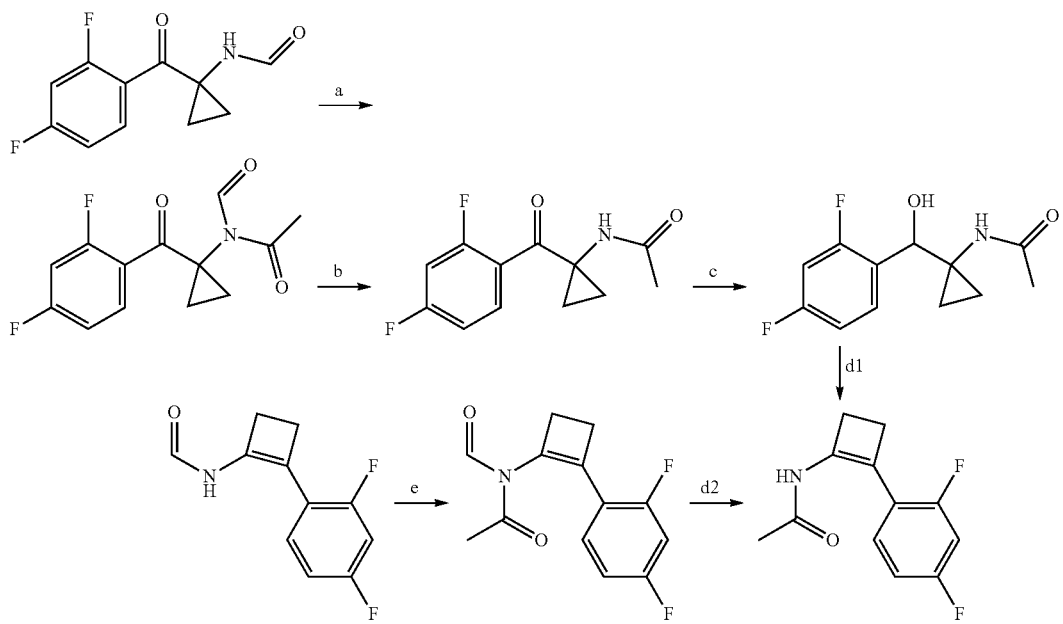

a. Preparation of N-[1-(2,4-difluorobenzoyl)cyclopropyl]-N-formyl-acetamide

N-[1-(2,4-Difluorobenzoyl)cyclopropyl]formamide (2 g) was suspended acetonitrile (10.2 ml). To this was added acetic anhydride (4.2 ml) and triethylamine (2.47 ml). The resulting solution was heated under stirring at 75° C. overnight. After 28 h total time, the mixture was cooled down to room temperature, diluted with ethyl acetate and poured into a separatory funnel containing saturated aqueous sodium bicarbonate solution. The phases were separated and the aqueous phase was extracted twice with ethyl acetate. The organic phase was washed with a saturated aqueous solution of sodium bicarbonate, then with brine, the combined organic phases were then dried over solid sodium sulfate, filtered and concentrated under vacuum. N-[(1-(2,4-difluorobenzoyl)cyclopropyl]-N-formyl-acetamide was obtained as an oil. ¹H NMR (400 MHz, CDCl₃) δ ppm 1.43-1.54 (m, 2 H), 1.91-1.99 (m, 2 H), 2.35 (s, 3 H), 6.76-6.99 (m, 2 H), 7.28-7.42 (m, 1 H), 9.14 (s, 1 H)

b. Preparation of N-[1-(2,4-difluorobenzoyl)cyclopropyl]acetamide

N-[(1-(2,4-Difluorobenzoyl)cyclopropyl]-N-formyl-acetamide (2.7 g) was dissolved in methanol (10 ml). To this solution was added potassium carbonate (0.7 g). The reaction mixture was stirred at room temperature for 30 minutes, diluted with ethyl acetate and poured into a separatory funnel containing saturated aqueous sodium bicarbonate solution. The phases were separated and the aqueous phase was extracted twice with ethyl acetate. The organic phase was washed with water, and then with brine, the combined organic phases were then dried over solid sodium sulfate, filtered and concentrated under vacuum. The crude material was purified over a 80 g silica gel chromatography column. N-[1-(2,4-difluorobenzoyl)cyclopropyl]acetamide was obtained as a solid. $^1$H NMR (400 MHz, CDCl3) δ ppm 1.21-1.27 (m, 2 H), 1.76 (s, 3 H), 1.78-1.84 (m, 2 H), 6.39 (br. s., 1 H), 6.82 (t, J=9.48 Hz, 1 H), 6.95 (td, J=8.25, 2.20 Hz, 1 H), 7.51-7.59 (m, 1 H)

c. Preparation of N-[1-[(2,4-difluorophenyl)-hydroxy-methyl]cyclopropyl]acetamide N-[1-(2,4-Difluorobenzoyl)cyclopropyl]acetamide (1.525 g) was dissolved in ethanol (19 ml) and the solution was cooled down to 0° C. Sodium borohydride (72 mg) was added to the resulting solution in one portion. After 15 min stirring at 0° C., the reaction mixture was allowed to warm at room temperature and stirred for half an hour more. After that time and every half an hour for 90 minutes, sodium borohydride (12 mg) was added to the mixture. It was then cooled down to 0° C. and aqueous saturated ammonium chloride solution (12 ml) was added slowly. The mixture was then diluted with ethyl acetate and poured onto an aqueous saturated solution of ammonium chloride. The phases were separated and the aqueous phase was extracted twice with ethyl acetate. The combined organic phases were washed with an aqueous saturated solution of ammonium chloride, then brine, before being dried over solid sodium sulfate, filtered and concentrated under vacuum. The desired product N-[1-[(2,4-difluorophenyl)-hydroxy-methyl]cyclopropyl]acetamide was obtained as a sticky oil. $^1$H NMR (400 MHz, CDCl3) δ ppm 0.69-0.80 (m, 1 H), 0.90-1.07 (m, 1 H), 1.07-1.19 (m, 2 H), 1.88 (s, 3 H), 4.52 (d, J=5.50 Hz, 1 H), 5.85 (d, J=5.87 Hz, 1 H), 5.97 (br. s., 1 H), 6.76 (ddd, J=10.55, 8.53, 2.57 Hz, 1 H), 6.89 (td, J=8.25, 1.83 Hz, 1 H), 7.46-7.57 (m, 1 H)

d. Preparation of N-[2-(2,4-difluorophenyl)cyclobuten-1-yl]acetamide (d1)
To a solution of N-[1-[(2,4-difluorophenyl)-hydroxy-methyl]cyclopropyl]acetamide (216 mg) in toluene (2.7 ml) was added sulfur trioxide pyridine complex (Py.SO$_3$; 214 mg; 45% SO$_3$). The resulting suspension is heated at 80° C. for 90 minutes, before being diluted with ethyl acetate and added to a saturated aqueous sodium bicarbonate solution. The phases were separated and the aqueous phase was extracted twice with ethyl acetate. The organic phase was washed with a saturated aqueous solution of sodium bicarbonate, then with brine, the combined organic phases were then dried over solid sodium sulfate, filtered and concentrated under vacuum. N-[2-(2,4-difluorophenyl)cyclobuten-1-yl]acetamide was obtained as a solid.

(d2)
N-[2-(2,4-Difluorophenyl)cyclobuten-1-yl]-N-formyl-acetamide (123 mg) was dissolved in isopropanol (0.53 ml), and to this solution was added potassium carbonate (0.036 g). The reaction mixture was heated to 60° C. for 3 hours, before being allowed to cool down to room temperature, diluted with ethyl acetate and poured into a separatory funnel containing saturated aqueous sodium bicarbonate solution. The phases were separated and the aqueous phase was extracted twice with ethyl acetate. The organic phase was washed with a saturated aqueous solution of sodium bicarbonate, then with brine, the combined organic phases were then dried over solid sodium sulfate, filtered and concentrated under vacuum. N-[2-(2,4-difluorophenyl)cyclobuten-1-yl]acetamide was obtained as a solid. $^1$H NMR (400 MHz, CDCl3) δ ppm 2.08 (s, 3 H), 2.56 (t, J=3.30 Hz, 2 H), 3.09 (br. s., 2 H), 6.76-6.92 (m, 2 H), 7.03-7.15 (m, 1 H), 7.72 (d, J=9.90 Hz, 1 H)

e. Preparation of N-[2-(2,4-difluorophenyl)cyclobuten-1-yl]-N-formyl-acetamide

N-[2-(2,4-Difluorophenyl)cyclobuten-1-yl]formamide (0.5 g) was suspended in acetonitrile (2.8 ml). To this was added acetic anhydride (0.7 ml) and triethylamine (0.66 ml). The resulting solution was heated under stirring at 75° C. After 5 h, the mixture was cooled down to room temperature, diluted with ethyl acetate and poured into a separatory funnel containing saturated aqueous sodium bicarbonate solution. The phases were separated and the aqueous phase was extracted twice with ethyl acetate. The organic phase was washed with a saturated aqueous solution of sodium bicarbonate, then with brine, the combined organic phases were then dried over solid sodium sulfate, filtered and concentrated under vacuum. N-[2-(2,4-difluorophenyl)cyclobuten-1-yl]N-formyl-acetamide was obtained as an oil. $^1$H NMR (400 MHz, CDCl3) δ ppm 2.27 (s, 3 H), 2.73-2.77 (m, 2 H), 2.85-2.88 (m, 2 H), 6.80 (ddd, J=10.82, 8.62, 2.57 Hz, 1 H), 6.88 (td, J=8.25, 2.57 Hz, 1 H), 7.21-7.28 (m, 1 H), 9.31 (s, 1 H)

Example P8

Preparation of N-[2-(2,4-dichlorophenyl)cyclobuten-1-yl]formamide

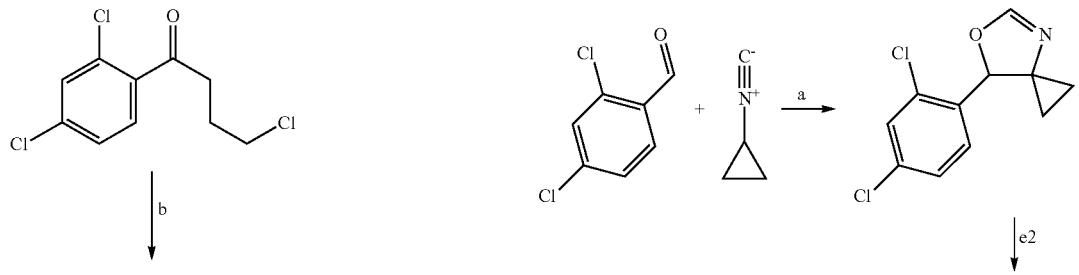

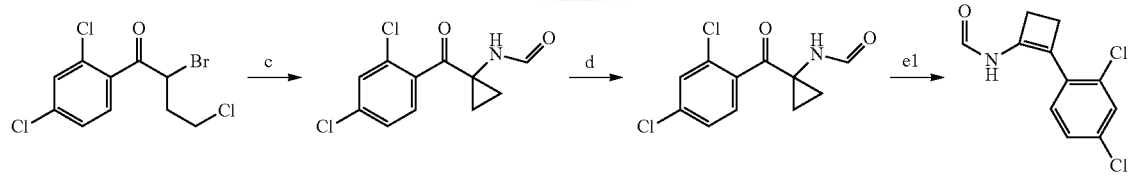

a. Preparation of 4-(2,4-dichlorophenyl)-5-oxa-7-azaspiro[2.4]hept-6-ene

To a suspension of cyclopropylisonitrile (0.7 ml) in tetrahydrofurane (25 ml) was added, at −78° C., nBuLi (6.05 mL; 1.6M hexane solution). After stirring at −78° C. for 15 minutes, a solution of 2,4-dichlorobenzaldehyde (1.6 g) in THF (7 ml) was added dropwise. The reaction mixture was stirred 2 hours at −78° C., before being quenched by the addition of methanol (4.5 ml). It was then allowed to warm to room temperature, before being diluted with ethyl acetate and poured into a separatory funnel containing saturated aqueous ammonium chloride solution. The phases were separated and the aqueous phase was extracted twice with ethyl acetate. The organic phase was washed once more with saturated ammonium chloride aqueous solution, then with brine, the combined organic phases were then dried over solid sodium sulfate, filtered and concentrated under vacuum. The crude material was purified over a 80 g silica gel chromatography column. 4-(2,4-Dichlorophenyl)-5-oxa-7-azaspiro[2.4]hept-6-ene was obtained as an oil. $^1$H NMR (400 MHz, CDCl3) δ ppm 0.43 (ddd, J=9.81, 6.88, 5.69 Hz, 1 H), 0.90-1.05 (m, 2 H), 1.24 (ddd, J=10.36, 7.06, 4.95 Hz, 1 H), 5.80 (s, 1 H), 7.03 (s, 1 H), 7.27-7.41 (m, 2 H)

b. Preparation of 2-bromo-4-chloro-1-(2,4-dichlorophenyl)butan-1-one

To a solution of 4-chloro-1-(2,4-dichlorophenyl)butan-1-one (2.4 g) in dichloromethane (24 ml) was added, at room temperature, bromine (0.513 ml). After 30 minutes stirring, 9.5 mL of a 1N aqueous sodium hydroxide solution (9.5 ml; 1 N) was added slowly. The mixture was then diluted with dichloromethane and poured onto an aqueous solution of NaHSO3 (10%). The phases were separated and the aqueous phase was extracted twice with dichloromethane. The organic phase was washed with an aqueous solution of NaHSO3 (10%), then with brine, the combined organic phases were then dried over solid sodium sulfate, filtered and concentrated under vacuum. 2-bromo-4-chloro-1-(2,4-dichlorophenyl)butan-1-one was obtained as an oil. $^1$H NMR (400 MHz, CDCl3) δ ppm 2.47-2.67 (m, 2 H), 3.79 (dd, J=6.79, 4.95 Hz, 2 H), 5.43 (dd, J=8.80, 5.14 Hz, 1 H), 7.35 (dd, J=8.44, 1.83 Hz, 1 H), 7.47 (d, J=1.83 Hz, 1 H), 7.52 (d, J=8.44 Hz, 1 H)

c. Preparation of N-[1-(2,4-dichlorobenzoyl)cyclopropyl]formamide

N-[1-(2,4-Dichlorobenzoyl)cyclopropyl]formamide was prepared according the procedure described above for N-[1-(2,4-difluorobenzoyl)cyclopropyl]formamide (Example P6 a). $^1$H NMR (400 MHz, CDCl3) δ ppm (Major rotamer) 1.36-1.40 (m, 2 H), 1.87-1.92 (m, 2 H), 6.38 (br. s., 1 H), 7.26-7.38 (m, 3 H), 7.91 (s, 1 H)

d. Preparation of N-[1-[(2,4-dichlorophenyl)-hydroxy-methyl]cyclopropyl]formamide N-[1-[(2,4-Dichlorophenyl)-hydroxy-methyl]cyclopropyl]formamide was prepared according the procedure described above for N-[1-[(2,4-difluorophenyl)-hydroxy-methyl]cyclopropyl]formamide (Example P6 b) $^1$H NMR (400 MHz, CDCl3) δ ppm (Major rotamer) 0.80-1.00 (m, 3H), 1.27-1.33 (m, 1 H), 4.91 (d, J=4.40 Hz, 1H), 5.34 (d, J=4.77 Hz, 1H), 6.01 (br. s., 1H), 7.27 (dd, J=8.44, 1.83 Hz, 1H), 7.35 (d, J=2.20 Hz, 1H), 7.53 (d, J=8.44 Hz, 1H), 8.07 (s, 1 H)

e. Preparation of N-[2-(2,4-dichlorophenyl)cyclobuten-1-yl]formamide (e1)
N-[2-(2,4-Dichlorophenyl)cyclobuten-1-yl]formamide was prepared according the procedure described above for N-[2-(2,4-difluorophenyl)cyclobuten-1-yl]formamide (Example P6 c)

(e2)
N-[2-(2,4-Dichlorophenyl)cyclobuten-1-yl]formamide was prepared from 4-(2,4-dichlorophenyl)-5-oxa-7-azaspiro[2.4]hept-6-ene. To a solution of 4-(2,4-dichlorophenyl)-5-oxa-7-azaspiro[2.4]hept-6-ene (40 mg) in dichloroethane (1 ml) was added, at room temperature, BF$_3$.Et$_2$O (0.011 ml). The reaction mixture was heated at 60° C. for 2 hours, before being allowed to cool down to room temperature, diluted with ethyl acetate and poured into a separatory funnel containing saturated aqueous sodium bicarbonate solution. The phases were separated and the aqueous phase was extracted twice with ethyl acetate. The organic phase was washed with brine, the combined organic phases were then dried over solid sodium sulfate, filtered and concentrated under vacuum. N-[2-(2,4-dichlorophenyl)cyclobuten-1-yl]formamide was obtained as a solid. $^1$H NMR (400 MHz, CDCL3) δ ppm Major rotamer 2.75 (t, J=3.30 Hz, 1H), 2.80 (t, J=3.30 Hz, 1H), 7.14 (d, J=8.44 Hz, 1H), 7.22 (dd, J=8.44, 2.20 Hz, 1H), 7.37 (d, J=2.20 Hz, 1H), 7.87-8.12 (br.d., J=8.1 Hz, 1H), 8.39 (d, J=11.4 Hz, 1H) Minor rotamer 2.71 (t, J=3.48 Hz, 1 H), 3.08 (t, J=3.48 Hz, 1 H), 7.15 (d, J=8.44 Hz, 1H), 7.22 (dd, J=8.44, 2.20 Hz, 1H), 7.36 (d, J=2.20 Hz, 1H), 7.66 (br. s., 1 H), 8.23 (s, 1 H)

Example P9

Preparation of N-[2-(2,4-dichlorophenyl)cyclobuten-1-yl]acetamide

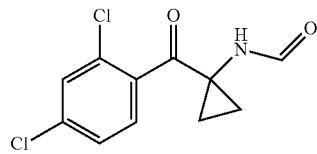

↓ a

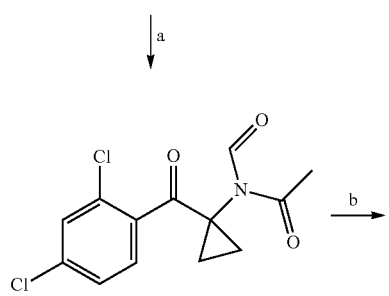

a. Preparation of N-[1-(2,4-dichlorobenzoyl)cyclopropyl]-N-formyl-acetamide

N-[(1-(2,4-Dichlorobenzoyl)cyclopropyl]-N-formyl-acetamide was prepared according the procedure described above for N-[(1-(2,4-difluorobenzoyl)cyclopropyl]-N-formyl-acetamide (example P7 a). ¹H NMR (400 MHz, CDCl3) δ ppm 1.82-2.00 (m, 2 H), 2.22 (s, 2 H), 2.40 (s, 3 H), 7.24 (d, J=8.44 Hz, 1H), 7.29 (dd, J=8.44, 2.20 Hz, 1H), 7.42 (d, J=1.83 Hz, 1 H), 9.19 (s, 1 H)

b. Preparation of N-[1-(2,4-dichlorobenzoyl)cyclopropyl]acetamide

N-[1-(2,4-Dichlorobenzoyl)cyclopropyl]acetamide was prepared according the procedure described above for N-[1-(2,4-difluorobenzoyl)cyclopropyl]acetamide (Example P7 b). ¹H NMR (400 MHz, CDCl3) δ ppm 1.30-1.35 (m, 2 H), 1.72 (s, 3 H), 1.83-1.88 (m, 2 H), 6.30 (br. s., 1 H), 7.29 (dd, J=8.07, 1.83 Hz, 1H), 7.33 (d, J=8.07 Hz, 1H), 7.36 (d, J=1.83 Hz, 1 H)

c. Preparation of N-[1-[(2,4-dichlorophenyl)-hydroxy-methyl]cyclopropyl]acetamide N-[1-[(2,4-Dichlorophenyl)-hydroxy-methyl]cyclopropyl]acetamide was prepared according to the procedure described above for N-[1-[(2,4-difluorophenyl)-hydroxy-methyl]cyclopropyl]acetamide (example P7 c). ¹H NMR (400 MHz, CDCl3) δ ppm 0.73-1.02 (m, 3H), 1.16-1.34 (m, 1H), 1.93 (s, 3H), 4.86 (s, 1 H), 5.86 (br. s., 1 H), 5.92 (br. s., 1 H), 7.25 (d, J=8.44 Hz, 1 H), 7.35 (s, 1 H), 7.52 (d, J=8.44 Hz, 1 H).

d. Preparation of N-[2-(2,4-dichlorophenyl)cyclobuten-1-yl]acetamide

N-[2-(2,4-Dichlorophenyl)cyclobuten-1-yl]acetamide was prepared according to the procedure described above for N-[2-(2,4-difluorophenyl)cyclobuten-1-yl]acetamide (Example P7 d1). ¹H NMR (400 MHz, CDCl3) δ ppm 2.06 (3H, s); 2.65 (2H, m); 3.06 (2H, m); 7.12 (1H, d); 7.19 (1H, d); 7.32 (1H, s); 7.58 (1H, br, s, NH).

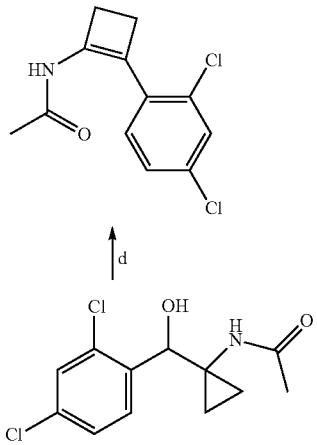

Example P10

Preparation of (1S,2S)-2-(2,4-difluorophenyl)cyclobutanamine hydrochloride

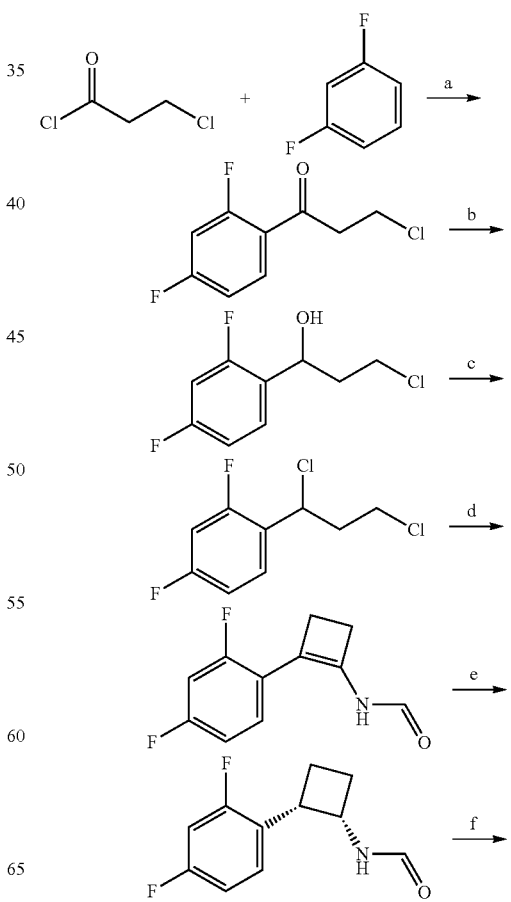

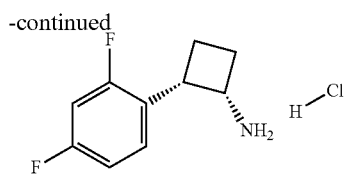

a. Preparation of 3-chloro-1-(2,4-difluorophenyl)propanone

To a stirred suspension of aluminium chloride (15.7 g, 118.1 mmol) in 1,3-difluorobenzene (11 ml, 118.1 mmol) heated to 50° C. was added 3-chloropropanoyl chloride (10 g, 78.7 mmol) by syringe over 10 min. The mixture was stirred at 50° C. for 1 h. The reaction mixture was poured onto ice water (200 ml) and stirred for 3 min. The mixture was next extracted with AcOEt (3×100 ml), and the combined organic layers were washed with NaHCO$_3$ (100 ml) and brine (100 ml). The organic layer was dried over Na$_2$SO$_4$ and the solvent was evaporated to give 3-chloro-1-(2,4-difluorophenyl)propanone as an oil $^1$H NMR (CDCl3) δ (ppm) 3.46 (d, 2H) 3.87-3.97 (m, 2H) 6.92 (ddd, 1H) 6.86-6.96 (m, 1H); 6.97-7.06 (m, 1H) 7.94-8.08 (m, 1H)

b. Preparation of 3-chloro-1-(2,4-difluorophenyl)propanol

To a solution of 3-chloro-1-(2,4-difluorophenyl)propanone (5 g, 24.4 mmol) in methanol (83 mL) was added sodium borohydride (1.70 g, 44.0 mmol) portionwise at 0° C. The mixture was diluted with saturated aqueous NH$_4$Cl (100 ml) and stirred for 10 min. It was extracted with AcOEt (3×100 ml), the combined organic layers were dried over Na$_2$SO$_4$ and the solvent was evaporated in vacuo. The crude product was purified by flash chromatography (Cyclohexane:AcOEt, 0-30% AcOEt) to yield 3-chloro-1-(2,4-difluorophenyl)propanol as a slightly yellow oil.

$^1$H NMR (CDCl$_3$) δ (ppm) 2.20-2.50 (m, 3H); 3.59-3.70 (m, 1H); 3.74-3.85 (m, 1H); 5.23 (m, 1H); 6.60-6.80 (m, 1H); 6.90-6.98 (m, 1H); 7.48 (d, 1H)

c. Preparation of 1-(1,3-dichloropropyl)-2,4-difluoro-benzene

To 3-chloro-1-(2,4-difluorophenyl)propanol (1 g, 4.65 mmol) was added concentrated hydrogen chloride (4.23 ml) and the resulting emulsion was stirred at room temperature for 30 min then at 60° C. for another 30 min. Water (20 ml) was then carefully added to the reaction mixture and it was extracted with cyclohexane (3×20 ml). The combined organic layers were dried over Na$_2$SO$_4$, filtered and the solvent was evaporated in vacuo to give 1-(1,3-dichloropropyl)-2,4-difluoro-benzene as an oil.

$^1$H NMR (CDCl$_3$) δ (ppm) 2.31-2.44 (m, 1H); 2.48-2.59 (m, 1H); 3.55-3.65 (m, 1H); 3.68-3.79 (m, 1H); 5.34-5.43 (m, 1H); 6.73-6.94 (m, 2H); 7.35-7.49 (m, 1H)

d. Preparation of N-[(2-(2,4-difluorophenyl)cyclobuten-1-yl]formamide

To a suspension of sodium hydroxide (0.43 g, 10.7 mmol) in DMSO (5.4 ml) was added a solution of toluenesulfonylmethyl isocyanide (0.47 g, 2.36 mmol) and 1-(1,3-dichloropropyl)-2,4-difluoro-benzene (0.51 g, 2.14 mmol) at room temperature for 4 h. Sodium hydroxide 5$_M$ (0.43 ml, 2.14 mmol) was then added and the resulting mixture was heated at 60° C. for 2 h then cooled down to r.t. Water (20 ml) was added to the reaction mixture and it was extracted with AcOEt (3×20 ml). The combined organic layers were dried over Na$_2$SO$_4$, filtered and the solvent was evaporated in vacuo. The crude product was purified by chromatography on silica (Cyclohexane:AcOEt, 0-40% AcOEt) to yield N-[2-(2,4-difluorophenyl)cyclobuten-1-yl]formamide as a brownish solid.

Major rotamer: $^1$H-NMR (400 MHz, CDCl$_3$): δ I 2.65-2.70 (m, 2 H), 2.85-2.89 (m, 2 H), 6.87-6.93 (m, 2 H), 7.10-7.15 (m, 1 H), 7.95 (bs, 1 H), 8.38-8.52 (m, 2 H).

Minor rotamer: $^1$H-NMR (400 MHz, CDCl$_3$): δ I 2.63-2.67 (m, 2 H), 3.14-3.20 (m, 2 H), 6.80-6.85 (m, 1 H), 7.10-7.16 (m, 2 H), 7.75 (bs, 1 H), 8.21-8.30 (m, 1 H).

e. Preparation of N-[(1S,2S)-2-(2,4-difluorophenyl)cyclobutyl]formamide

As performed in Example P6 step d.

f. Preparation of (1S,2S)-2-(2,4-difluorophenyl)cyclobutanamine hydrochloride N-[(1S,2S)-2-(2,4-difluorophenyl)cyclobutyl]formamide (0.497 mmol, 0.105 g) was introduced in a 10 ml round-bottom flask and diluted in methanol (5 ml). Hydrochloric acid 36% (4.97 mmol, 0.592 g, 0.497 ml) was added in one portion, then the reaction mixture was stirred at reflux for 2 hours. Methanol was evaporated, then some diethyl ether and water were added to the mixture. The phases were separated and the aqueous phase was washed with a small volume of diethyl ether. The aqueous phase was mixed with diethyl ether and cooled down to 0° C. whereupon sodium hydroxide (30% solution; 0.5 ml) was slowly added. The phases were separated again and the aqueous phase was extracted twice with diethyl ether. The organic layers were combined, dried over anhydrous sodium sulfate, filtered and concentrated to give an orange oil. The oil was diluted in diethyl ether and cooled down to 0° C. whereupon HCl (2M in diethyl ether) was added drop-wise. A solid precipitated. This solid was isolated by filtration, washed with diethyl ether and dried on high vacuum pump to afford a white powder corresponding to the desired product. This solid was analyzed via chiral HPLC (method Z) which showed an ee of 81.8% in favour of the desired enantiomer eluting at 4.99 min (minor enantiomer eluting at 5.68 min).

1H NMR (400 MHz, DMSO-d6) d ppm 8.04 (3 H, br. s.), 7.45-7.60 (1 H, m), 7.18-7.28 (1 H, m), 7.13 (1 H, td), 4.07 (1 H, q), 3.81-3.97 (1 H, m), 2.69-2.85 (1 H, m), 2.39-2.48 (1 H, m), 2.12-2.25 (1 H, m), 1.80-1.95 (1 H, m).

Example P11

Preparation of (1S,2S)-2-(2,4-dichlorophenyl)cyclobutanamine

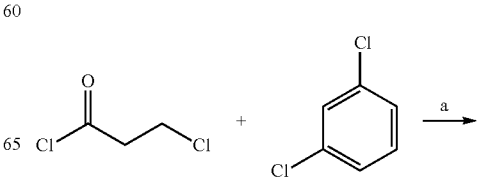

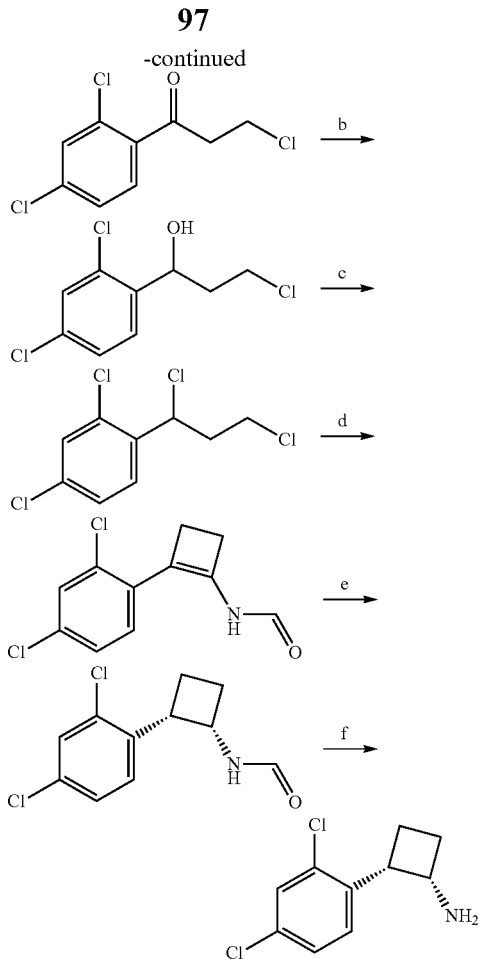

a. Preparation of 3-chloro-1-(2,4-dichlorophenyl)propanone

To a stirred suspension of aluminum chloride (12.6 g, 94.5 mmol) in 1,3-dichlorobenzene (13.5 ml, 118 mmol) was added 3-chloropropanoyl chloride (7.55 ml, 78.8 mmol) dropwise at 50° C. The resulting mixture was stirred at 50° C. for 2.5 h, then at 60° C. for 1.5 h. The reaction mixture was poured on ice and water (1:1, 500 ml) and it was stirred for 5 min. The mixture was then extracted with AcOEt (3×100 ml). The combined organic layers were washed with brine, dried over Na$_2$SO$_4$, filtered and the solvent was evaporated in vacuo. The crude product was further purified by distilling off remaining dichlorobenzene in vacuo (70° C., 10 mbar) to give 3-chloro-1-(2,4-dichlorophenyl)propanone.

$^1$H-NMR (400 MHz, CDCl$_3$): δ=3.34 (t, 2 H) 3.79 (t, 2 H), 7.21-7.26 (m, 1 H), 7.33-7.39 (m, 1 H) 7.40-7.50 (m, 1 H).

b. Preparation of 3-chloro-1-(2,4-dichlorophenyl)propanol

To a solution of 3-chloro-1-(2,4-dichlorophenyl)propanone (10 g, 35.8 mmol) in methanol (122 ml) was added sodium borohydride (1.37 g, 35.8 mmol) portionwise at 0° C. The resulting mixture was stirred at 0° C. for 2 h. An NH$_4$Cl aqueous solution (half-saturated, 200 ml) was added to the reaction mixture and it was extracted with AcOEt (3×100 ml). The combined organic layers were dried over Na$_2$SO$_4$, filtered and the solvent was evaporated in vacuo. The crude product was purified by column chromatography (cyclohexane:AcOEt 0-20%) to give 3-chloro-1-(2,4-dichlorophenyl)propanol as an oil.

$^1$H-NMR (400 MHz, CDCl$_3$): δ 2.05-2.25 (m, 3 H), 3.69-3.88 (m, 2 H), 5.31-5.38 (m, 1 H), 5.31-5.35 (m, 1 H), 5.40-5.43 (m, 1 H), 5.55-5.58 (m, 1 H).

c. Preparation of 1-(1,3-dichloropropyl)-2,4-dichloro-benzene

To a solution of lithium chloride (0.087 g, 2.05 mmol) in DMF (1.0 ml) was added 3-chloro-1-(2,4-dichlorophenyl)propanol (129 mg, 0.51 mmol) and thionyl chloride (0.112 ml, 1.54 mmol) at room temperature. The resulting mixture was stirred at room temperature for 2 h. Water (10 ml) was added to the reaction mixture and it was extracted with tBuOMe (1×10 ml). The combined organic layers were dried over Na$_2$SO$_4$, filtered and the solvent was evaporated in vacuo to give 1-(1,3-dichloropropyl)-2,4-dichloro-benzene as an oil.

$^1$H-NMR (400 MHz, CDCl$_3$): δ 2.25-2.38 (m, 2 H), 3.51-3.71 (m, 2 H), 5.49-5.52 (m, 1 H), 7.17-7.22 (m, 1 H), 7.30-7.33 (m, 1 H), 7.40-7.44 (m, 1 H).

d. Preparation of N-[2-(2,4-dichlorophenyl)cyclobuten-1-yl]formamide

To a suspension of potassium hydroxide (0.22 g, 3.89 mmol) in DMSO (2.0 ml) was added dropwise at RT a solution of 2,4-dichloro-1-(1,3-dichloropropyl)benzene (211 mg, 0.78 mmol) and 1-(isocyanomethylsulfonyl)-4-methylbenzene (168 mg, 0.86 mmol) in DMSO (1.0 ml). The resulting mixture was stirred for 3 h at room temperature and 5M aqueous potassium hydroxide (0.78 mL, 3.89 mmol) was added. The mixture was then stirred overnight. Water (20 ml) and aqueous NH$_4$Cl-solution (5 ml) was added to the reaction mixture and it was extracted with AcOEt (3×20 ml). The combined organic layers were washed with brine (10 ml), dried over Na$_2$SO$_4$, filtered and the solvent was evaporated. The crude product was purified by flash chromatography (Cyclohexane:AcOEt, 0-30% AcOEt) to yield the desired compound as a colourless solid.

Major rotamer: $^1$H-NMR (400 MHz, CDCl$_3$): δ=2.64-2.73 (m, 2 H), 7.09-7.16 (m, 1 H), 7.10-7.16 (m, 1 H), 7.23-7.31 (m, 1 H), 7.88-8.06 (m, 1 H), 8.25-8.34 (m, 1 H) ppm.

Minor rotamer: $^1$H-NMR (400 MHz, CDCl$_3$): δ=2.59-2.64 (m, 1 H), 2.96.3.03 (m, 1 H), 7.09-7.16 (m, 1 H), 7.10-7.16 (m, 1 H), 7.23-7.31 (m, 1 H), 7.51-7.62 (bs, 1 H), 8.09-8.13 (m, 1 H) ppm.

e. Preparation of N-[(1S,2S)-2-(2,4-dichlorophenyl)cyclobutyl]formamide

To an inert and degassed 2,2,2-trifluoroethanol (4 ml) was added (R)-1-[(S)-2-(Di-tert-butylphosphino)ferrocenyl]-ethyl-di-2-methylphenylphosphine (0.041 mmol, 24 mg) and bis(1,5-cyclooctadiene)rhodium(I) trifluoromethanesulfonate (0.038 mmol, 18 mg) at room temperature under an argon atmosphere over 10 minutes. The reaction mixture was then transferred into a 100 ml autoclave previously filled with argon and N-[2-(2,4-dichlorophenyl)cyclobuten-1-yl]formamide (0.38 mmol, 91 mg). The autoclave was tightly closed and submitted to hydrogen under 50 bar at 50° C. for 22 hours. The autoclave was opened then the reaction mixture was filtered through Celite and the solvent was evaporated in vacuo. The crude product was purified by chromatography on silica (dichloromethane:Methanol, 0-10% Methanol) to yield N-[(1S,2S)-2-(2,4-dichlorophenyl)cyclobutyl]formamide as an orange amorphous solid.

Major rotamer: $^1$H NMR (400 MHz, CDCl$_3$): d=1.95-2.04 (m, 1H), 2.26-2.40 (m, 2H), 2.50-2.66 (m, 1H), 4.12-4.21 (m, 1H), 4.95-5.02 (q, 1H), 5.13 (bs, 1H), 7.43-7.45 (d, 1H), 7.94 (s, 1H).

Minor rotamer: $^1$H NMR (400 MHz, CDCl$_3$): d=1.95-2.04 (m, 1H), 2.26-2.40 (m, 2H), 2.50-2.66 (m, 1H), 4.12-4.21 (m, 1H), 4.51-4.57 (q, 1H), 5.30 (bs, 1H), 7.40-7.43 (d, 1H), 7.96-7.99 (d, 1H).

f. Preparation of (1S,2S)-2-(2,4-dichlorophenyl)cyclobutanamine

To a solution of N-[2-(2,4-dichlorophenyl)cyclobutyl]formamide (66 mg, 0.24 mmol) in methanol (2.4 mL) was added 36% HCl (0.21 mL, 2.43 mmol) and the mixture was heated to 65° C. The mixture was heated for 2 h and then cooled to room temperature. The solvent was removed under reduced pressure. The residue was taken up in water (30 ml) and washed with MTBE (20 ml). The aqueous layer was basified with 5M NaOH (ca.1 ml) and extracted with MTBE (2×20 ml). The combined organic layers were dried over Na2SO4, filtered and the solvent was evaporated to yield a red oil. It was analysed via chiral HPLC (method Y) which showed an ee of 82% in favour of the desired enantiomer.

$^1$H-NMR (400 MHz, CDCl$_3$) ppm 0.95-1.28 (m, 2 H), 1.63-1.75 (m, 1 H), 2.14-2.28 (m, 1 H), 2.29-2.98 (m, 2 H), 3.89-4.03 (m, 2 H), 7.27-7.32 (m, 2 H), 7.41-7.43 (m, 1H) ppm.

Example P12

Preparation of 2,4-difluoro-1-(2-isocyanocyclobuten-1-yl)benzene

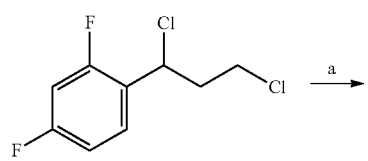

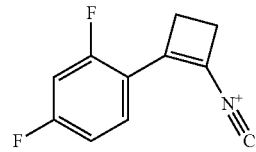

To a suspension of sodium hydride (0.056 g, 1.40 mmol) in DMSO (0.88 ml) and diethyl ether (0.32 ml) was added a solution of 1-(1,3-dichloropropyl)-2,4-difluoro-benzene (100 mg, 0.40 mmol) and toluenesulfonylmethyl isocyanide (0.097 g, 0.48 mmol) in DMSO (0.32 ml) and diethyl ether (0.12 ml) at room temperature over 1 min. The mixture was stirred for 5 h at room temperature and water (20 ml) was then added. The reaction mixture was extracted with pentane (3×20 ml). The combined organic layers were dried over Na$_2$SO$_4$, filtered and the solvent was carefully evaporated in light vacuo. $^1$H-NMR (400 MHz, CDCl$_3$): δ 2.64-2.74 (m, 2 H); 2.79-2.90 (m, 2 H); 6.73-7.00 (m, 2 H); 7.59-7.63 (m, 1 H) ppm

Example P13

Preparation of 2,4-difluoro-1-(2-isocyanocyclobuten-1-yl)benzene

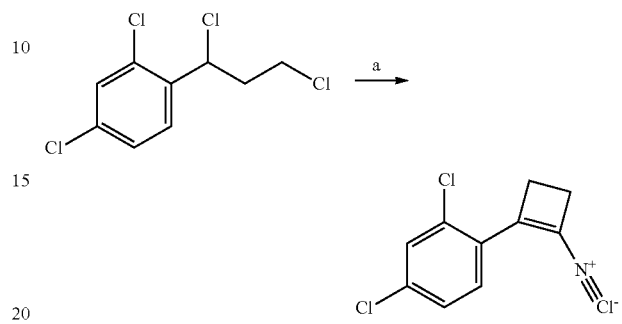

To a suspension of sodium hydride (108 mg, 2.71 mmol) in DMSO (2 ml) was added dropwise at room temperature a solution of 1-(isocyanomethylsulfonyl)-4-methyl-benzene (187 mg, 0.93 mmol) and 2,4-dichloro-1-(1,3-dichloropropyl)benzene (200 mg, 0.78 mmol) in DMSO (1 ml). The reaction mixture was stirred at room temperature for 2 h. Water (20 ml) was added to the reaction mixture and it was extracted with AcOEt (3×20 ml). The combined organic layers were dried over Na$_2$SO$_4$, filtered and the solvent was evaporated. The crude product was purified by flash chromatography (Cyclohexane:AcOEt, 0-50% AcOEt) to yield the desired compound as a brown solid. $^1$H-NMR (400 MHz, CDCl$_3$): δ=2.70-2.78 (m, 2 H); 2.80-2.87 (m, 2 H); 7.15-7.23 (m, 1 H); 7.29-7.32 (m, 1 H); 7.60-7.65 (m, 1 H).

Example P14

Preparation of N-[2-(2,4-difluorophenyl)cyclobuten-1-yl]-2-(trifluoromethyl)benzamide

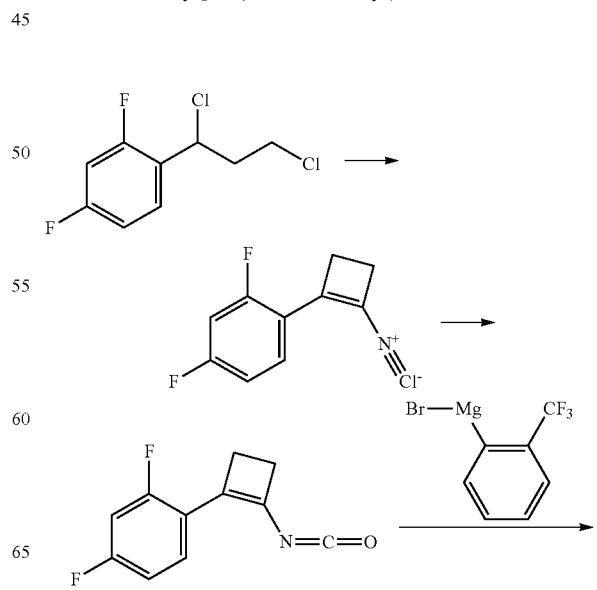

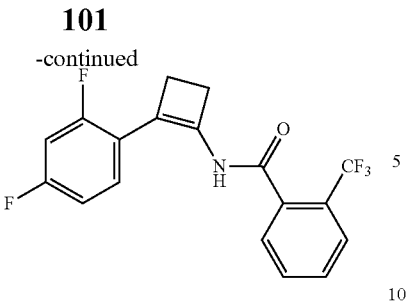

To a suspension of sodium hydroxide (0.42 g, 10.5 mmol) in DMSO (5 ml) was added a solution of toluenesulfonylmethyl isocyanide (0.46 g, 2.32 mmol) and 1-(1,3-dichloropropyl)-2,4-difluoro-benzene (500 mg, 2.11 mmol) in DMSO (3.4 mL) at room temperature. The mixture was then stirred at room temperature for 1.5 h. Water (20 ml) was added to the reaction mixture and it was extracted with hexane (2×20 mL). The combined organic layers were dried over $Na_2SO_4$ and filtered. The yellow solution was used in the next step without further purification.

The above solution was cooled to 0° C. and DMSO (0.16 ml, 2.32 mmol) was added, followed by trifluoroacetic anhydride (0.15 ml, 1.06 mmol). The mixture was stirred at 0° C. for 20 min.

A freshly prepared solution of 2-(trifluoromethyl)phenyl]magnesium bromide (from 1-bromo-2-(trifluoromethyl)benzene (500 mg, 2.22 mmol) in THF (6.7 ml) and (isopropyl) magnesium chloride (1.7 ml, 2.22 mmol) at 0° C. for 15 min then room temperature for 5 H) was then added and the reaction mixture was stirred at room temperature or 72 h. Water (50 ml) and $NaHCO_3$ aqueous solution (10 ml) were added to the reaction mixture and it was extracted with AcOEt (3×20 ml). The combined organic layers were dried over $Na_2SO_4$, filtered and the solvent was evaporated in vacuo. The resulting crude product was purified by flash chromatography (Cyclohexane:AcOEt, 0-10% AcOEt) to yield N-[2-(2,4-dichlorophenyl)cyclobuten-1-yl]-2-(trifluoromethyl)benzamide as a colorless solid.

$^1$H-NMR (400 MHz, $CDCl_3$): δ=2.63-2.69 (m, 2H); 3.21-3.28 (m, 2H); 6.71-6.81 (m, 1H); 6.84-6.92 (m, 1 H); 7.10-7.18 (m, 1H); 7.54-7.70 (m, 3H); 7.73-7.79 (m, 1H); 8.03-8.18 (m, 1H).

Example P15

Preparation of N-[2-(2,4-dichlorophenyl)cyclobuten-1-yl]formamide

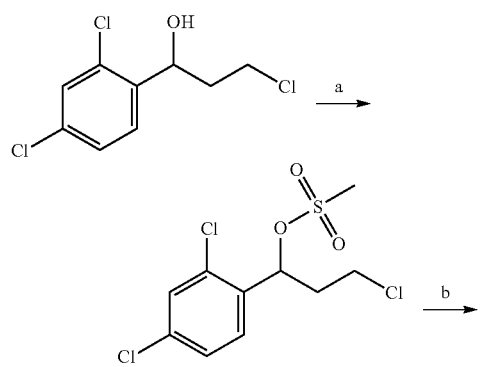

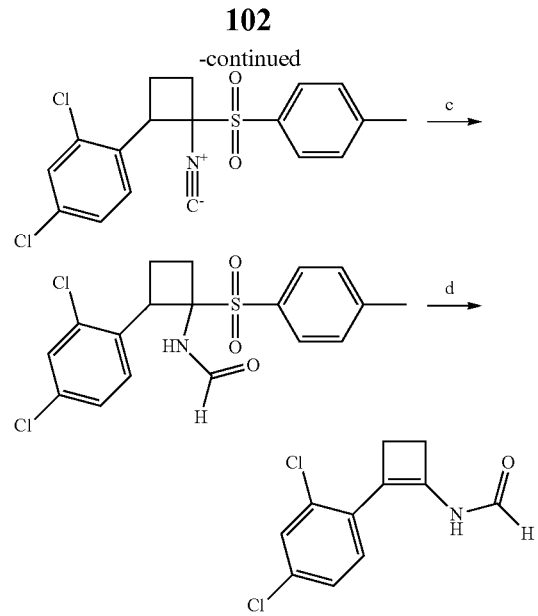

a. Preparation of 3-chloro-1-(2,4-dichlorophenyl) propyl]methanesulfonate

A solution of 3-chloro-1-(2,4-dichlorophenyl)propanol (2 g, 8.35 mmol) and triethylamine (1.76 ml, 1.28 g, 12.52 mmol) in dichloromethane (5 ml) was cooled to 0° C. and methanesulfonylchloride (0.714 ml, 1.05 g, 9.18 mmol) was added dropwise causing an exotherm. After the addition, the reaction mixture was stirred for 2 hours then poured onto ice and water. The mixture was extracted with tBuOMe, and the organic phase washed with HCl (1M), NaHCO3 (1M), and brine, then dried with Na2SO4 and evaporated to give [3-chloro-1-(2,4-dichlorophenyl)propyl]methanesulfonate as an oil.

$^1$H-NMR (400 MHz, $CDCl_3$): δ=2.23-2.44 (m, 2H); 2.94 (s, 3H); 3.62-3.77 (m, 2H); 6.17 (dd, 1H); 7.35 (dd, 1H); 7.44 (d, 1H); 7.50 (d, 1H)

b. Preparation of 2,4-dichloro-1-[2-isocyano-2-(p-tolylsulfonyl)cyclobutyl]benzene A mixture of [3-chloro-1-(2,4-dichlorophenyl)propyl] methanesulfonate (1.3 g, 4.1 mmol), toluenesulfonylmethyl isocyanide (820 mg, 4.1 mmol) and tetrabutylammonium iodide (760 mg, 2.0 mmol) in dichloromethane (ca 6 ml) was stirred with NaOH (ca 6 ml; 30% aq.) under argon at room temperature overnight. The mixture was shaken between EtOAc and water, dried with Na2SO4 and evaporated to yield the crude product as an oil, which was chromatographed on silica with EtOAc and cyclohexane to yield pure 2,4-dichloro-1-[2-isocyano-2-(p-tolylsulfonyl)cyclobutyl] benzene as white crystals m.p. 130-137.

$^1$H-NMR (400 MHz, $CDCl_3$): δ=2.30 (m, 1H); 2.40 (m, 1H); 2.46 (s, 3H); 2.59 (m, 1H); 4.97 (t, 1H); 7.32-7.48 (m, 5H); 7.88 (d, 2H).

c. Preparation of N-[(2-(2,4-dichlorophenyl)-1-(p-tolylsulfonyl)cyclobutyl]formamide To a solution of 2,4-dichloro-1-[2-isocyano-2-(p-tolylsulfonyl)cyclobutyl]benzene (100 mg, 0.26 mmol) in THF (0.5 ml) at room temperature was added HCl (2M, 0.26 mmol). The resulting mixture was stirred at room temperature for 5 h. Water and EtOAc were added. Layers were separated and the organic phase was further washed with aqueous NaHCO₃, brine, dried and concentrated in vacuo to afford N-[2-(2,4-dichlorophenyl)-1-(p-tolylsulfonyl)cyclobutyl]formamide. ¹H-NMR showed the compound to exist in CDCl3 solution as a mixture of two (major and minor) amide rotamers.

¹H-NMR (400 MHz, CDCl₃): δ=2.25-2.44 (m); 2.45 (2s, Me); 2.60-2.76 (m), 2.95 (m, minor); 3.08 (m, major); 3.20 (m, minor); 4.92 (dd, 1H, major); 5.04 (dd, 1H, minor); 5.31 (s, 1H, major); 5.33 (s, 1H, minor); 7.26-7.77 (m, 5H).

d. Preparation of N-[(2-(2,4-dichlorophenyl)cyclobuten-1-yl]formamide

N-[2-(2,4-Dichlorophenyl)-1-(p-tolylsulfonyl)cyclobutyl]formamide (46.0 mg, 0.115 mmol) was dissolved in THF (0.5 ml) and sodium tert-butoxide (2M in THF; 0.35 mmol) was added dropwise. The mixture became cloudy and brown. After the addition TLC (50% EtOAc in cyclohexane) showed complete reaction. Water was added and the mixture was extracted with EtOAc. The organic phase was washed with HCl (1M), aqueous NaHCO₃, brine, dried with Na2SO4, and concentrated in vacuo. The crude product was triturated with diethyl ether to afford N-[2-(2,4-dichlorophenyl)cyclobuten-1-yl]formamide as white solid. M.p. 132-137° C. ¹H-NMR showed the compound to exist in CDCl3 solution as a mixture of two (major and minor) amide rotamers.

¹H-NMR (400 MHz, CDCl₃): δ=2.70 (t, 2H, minor); 2.75 (t, 2H, major); 2.79 (t, 2H, major); 3.08 (t, 2H, minor); 7.12-7.38 (m, 3H major+minor); 7.57 (br s, 1H, minor); 7.86 (br s, 1H, major); 8.22 (s, 1H, minor); 8.40 (d, 1H, major).

Example P16

Preparation of N-[(1S,2S)-2-(2,4-difluorophenyl)cyclobutyl]-2-(trifluoromethyl)pyridine-3-carboxamide

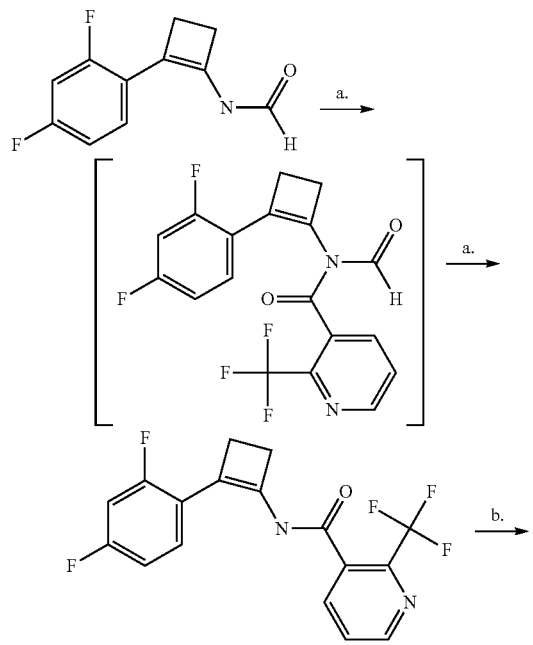

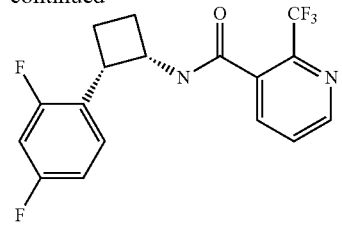

a. Preparation of N-[2-(2,4-difluorophenyl)cyclobuten-1-yl]-2-(trifluoromethyl)pyridine-3-carboxamide 2-(Trifluoromethyl)pyridine-3-carbonyl chloride solution: To a stirred solution of 2-(trifluoromethyl)pyridine-3-carboxylic acid (1.7 g, 8.9 mmol) and a catalytic amount of dimethylformamide in dichloromethane (10 ml), was added dropwise oxalylchloride (0.83 ml). The reaction mixture was stirred at room temperature for 18 hours, evaporated in vacuo and dissolved again in dichloromethane (10 ml).

2-(Trifluoromethyl)pyridine-3-carbonyl chloride solution (5.6 mmol, 2.2 equivalents) was added dropwise to a stirred suspension of N-[2-(2,4-difluorophenyl)cyclobuten-1-yl]formamide (537 mg) in toluene (8 ml) at 0° C. followed by addition of triethyl amine (0.79 ml). The reaction mixture was stirred at 0° C. for 90 minutes and at 40° C. for 1 hour. Another portion of 2-(trifluoromethyl)pyridine-3-carbonyl chloride solution (2.6 mmol, 1 equivalent), triethyl amine (0.4 ml) and a catalytic amount of 4-dimethylaminopyridine were added and the reaction mixture was stirred at room temperature for additional 16 hours.

LC/MS analysis reveals the presence of N-[2-(2,4-difluorophenyl)cyclobuten-1-yl]-N-formyl-2-(trifluoromethyl)pyridine-3-carboxamide intermediate:

LC-MS (ES+): m/z=383 (M+H) RT=1.69 (method G).

The mixture was taken up into ethyl acetate and the ethyl acetate solution was washed with saturated NaHCO₃, NH₄Cl, brine and it was dried (Na₂SO₄). Filtration and concentration by rotary evaporation gave a brown oil. It was dissolved in methanol (6 ml). Potassium carbonate (289 mmol) was added and the mixture was stirred for 75 minutes at room temperature, filtered and evaporated. The mixture was taken up into ethyl acetate and the ethyl acetate solution was washed with saturated NH₄Cl, brine and it was dried (Na₂SO₄). Filtration and concentration by rotary evaporation gave a brown solid.

N-[2-(2,4-difluorophenyl)cyclobuten-1-yl]-2-(trifluoromethyl)pyridine-3-carboxamide was isolated by column chromatography over silica gel (hexanes:ethyl acetate gradient) as an off-white solid.

m.p. 171-178° C.

¹H-NMR (CDCl₃, 400 Mhz): δ=8.82 (d, 1H, J=4.4 Hz), 8.07 (bd, 1H, J=12.8 Hz), 7.99 (d, 1H, J=7.7 Hz), 7.59-7.64 (m, 1H), 7.11-7.18 (m, 1H), 6.85-6.92 (m, 1H), 6.73-6.81 (m, 1H), 3.20-3.25 (m, 2H), 2.64-2.69 (m, 2H).

b. Preparation of N-[(1S,2S)-2-(2,4-difluorophenyl)cyclobutyl]-2-(trifluoromethyl)pyridine-3-carboxamide Bis(1,5-cyclooctadiene)rhodium(I) trifluoromethanesulfonate (3.3 mg) and (R)-1-[(S$_P$)-2-(Di-tert-butylphosphino)ferrocenyl]ethylbis(2-methyl phenyl)phosphine (4.0 mg) were dissolved in degassed methanol (5 ml) and the resulting catalyst solution was stirred for 30 min at room temperature under argon. Then, the catalysts solution (1 ml) and degassed methanol (4 ml) were transferred via syringe into a 100 ml stainless steel reactor containing N-[2-(2,4-difluorophenyl)cyclobuten-1-yl]-2-(trifluoromethyl)pyridine-3-carboxamide (50 mg) set under an atmosphere of argon. The reactor was purged 3 times with hydrogen (10 bar) and finally pressurized to 50 bar. The reaction mixture was stirred over 18 h at 50° C. After 18 h the autoclave was vented and the solvent was evaporated. N-[(1S,2S)-2-(2,4-difluorophenyl)cyclobutyl]-2-(trifluoromethyl)pyridine-3-carboxamide was isolated by column chromatography over silica gel (hexanes:ethyl acetate gradient) as a gum.

Chiral HPLC analysis (method C) showed a ee=50% in favour of the desired enantiomer eluting at 5.48 min (minor enantiomer eluting at 8.28 min).

$^1$H-NMR (CDCl$_3$, 400 MHz): δ=8.7 (d, 1H, J=4.4 Hz), 7.55-7.59 (m, 1H), 7.44-7.49 (m, 1H), 7.28-7.34 (m, 1H), 6.87-6.93 (m, 1H), 6.79-6.86 (m, 1H), 5.61 (bd, 1H, J=7.3 Hz), 4.95-5.04 (m, 1H), 4.11-4.19 (m, 1H), 2.58-2.69 (m, 1H), 2.29-2.43 (m, 2H), 2.07-2.18 (m, 1H).

Example P17

Preparation of (1R,4S)—N-[(1S,2S)-2-(4-chlorophenyl)cyclobutyl]-1,7,7-trimethyl-2-oxo-3-oxabicyclo[2.2.1]heptane-4-carboxamide

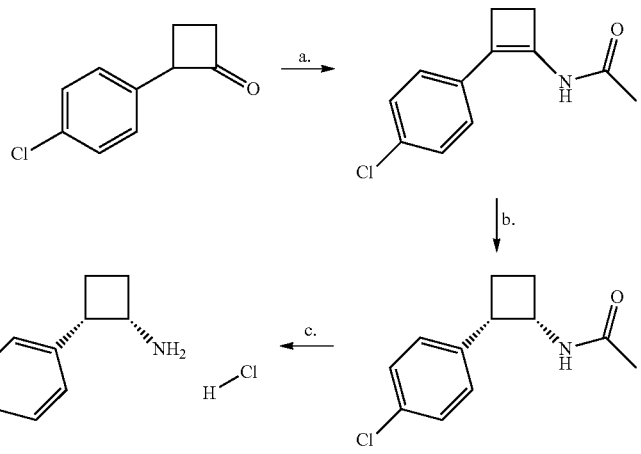

a. Preparation of N-[2-(4-chlorophenyl)cyclobuten-1-yl]acetamide

Dried acetamide (27.7 mmol, 1.67 g) and toluene-4-sulfonic acid monohydrate (0.0554 mmol, 0.0105 g) were introduced in a well dried 25 ml three-neck round-bottom flask equipped with a Dean Stark apparatus. Then 2-(4-chlorophenyl)cyclobutanone (5.54 mmol, 1.00 g; prepared as described in Example P3) was added as a solution in anhydrous toluene (11.1 ml), and the reaction mixture was submitted to an argon atmosphere and stirred at reflux. After overnight stirring at reflux (22 hours) with water collecting in the Dean Stark trap, the conversion of the starting material was almost complete. Water and ethyl acetate were added to the reaction mixture. A solid remained insoluble and was filtered off and discarded. The organic filtrate was washed with saturated sodium bicarbonate, dried with sodium sulfate and concentrated under vacuum to give a crude white solid. The crude was purified via recrystallization from AcOEt/cyclohexane to give the pure product.

1H-NMR (CDCl$_3$): 7.30 (2H, d), 7.11 (2H, d), 3.04 (2H, m), 2.56 (2H, m), 2.21 (1H, br s), 2.11 (3H, s).

b. Preparation of N-[(1S,2S)-2-(4-chlorophenyl)cyclobutyl]acetamide (R)-1-[(S)-2-(Di-tert-butylphosphino)ferrocenyl]-ethyl-di-2-methylphenylphosphine (0.0124 mmol, 0.00730 g) and bis(1,5-cyclooctadiene)rhodium(I) trifluoromethanesulfonate (0.0113 mmol, 0.00529 g) were weighted and transferred to a vial in an inert atmosphere. Methanol (5 ml) was introduced in a 25 ml round-bottom flask and degassed by flushing the flask several times with vacuum/argon cycles. Both catalyst and ligand were added, and the reaction mixture was stirred at room temperature under an argon atmosphere until everything was dissolved (15-20 minutes). In a 100 ml autoclave previously inerted with argon was introduced N-[2-(4-chlorophenyl)cyclobuten-1-yl]acetamide (2.26 mmol, 0.500 g). The catalyst/ligand solution was then introduced into the autoclave. The autoclave was tightly closed and submitted to hydrogen pressure (50 bar) at 50° C. during 4 hours. The reaction mixture was filtrated through Celite and a small layer of silica and concentrated to give an amber sticky oil which crystallized over time. This was the desired product, whose ee was determined with chiral HPLC (method V), ee=86% in favour of the desired enantiomer eluting at 4.20 min (minor enantiomer eluting at 3.72 min).

1H-NMR (CDCl3): 7.35 (2 H, d), 7.16 (2 H, d), 5.04 (1 H, br. s.), 4.79 (1 H, quin), 3.86 (1 H, m), 2.50 (1 H, m), 2.32-2.14 (2 H, m), 2.00 (1 H, m), 1.75 (3 H, s)

c. Preparation of (1S,2S)-2-(4-chlorophenyl)cyclobutanamine hydrochloride

N-[(1S,2S)-2-(4-chlorophenyl)cyclobutyl]acetamide (0.867 mmol, 0.194 g, ee=66%) was introduced in a 25 ml round-bottom flask and dissolved in methanol (5 ml). Hydrochloric acid 36% (43.4 mmol, 5.16 g, 4.34 ml) was added drop-wise. The reaction mixture was stirred at reflux overnight (16 hours). Methanol and hydrochloric acid were evaporated to give a dark solid. Some toluene was added and evaporated to distill off the remaining water. The solid was triturated in diethyl ether, filtrated and dried on high vacuum pump to afford a grey powder. This solid was analyzed via chiral HPLC (method W) which showed an ee=64% in favour of the desired enantiomer eluting at 4.00 min (minor enantiomer eluting at 4.56 min).

1H-NMR (DMSO d6): 8.04 (3H, br s) 7.45-7.24 (4H, m), 3.92 (2H, m), 2.64 (1H, m), 2.38 (1H, m), 2.23 (1H, m), 1.96 (1H, m).

d. Preparation of (1R,4S)—N-[(1S,2S)-2-(4-chlorophenyl)cyclobutyl]-1,7,7-trimethyl-2-oxo-3-oxabicyclo[2.2.1]heptane-4-carboxamide (1S,2S)-2-(4-chlorophenyl)cyclobutanamine hydrochloride (1.83 mmol, 0.400 g, ee=64%) was introduced in a 25 ml round-bottom flask and dissolved in dichloromethane (15 ml).

water (5 ml) and sodium bicarbonate (5.50 mmol, 0.462 g, 0.312 ml) were added subsequently, then the reaction mixture was cooled down to 0° C. (1S)-(−)-camphanic acid chloride (2.02 mmol, 0.437 g) was added drop-wise as a solution in dichloromethane (5 ml).

The ice bath was removed and the reaction mixture was stirred at room temperature during 3 hours. The organic phase was separated from the aqueous one, dried with anhydrous sodium sulfate, filtered and concentrated to give a pale yellow solid which was purified on silica gel chromatography. The major diastereoisomer was isolated pure and was crystallized from AcOEt/cyclohexane.

M.P: 148-149° C.

The stereochemistry of this compound was confirmed by X-ray crystallography under the conditions set out below and in Table 57. Bond lengths and angles for Example P17 are set out in Table 58 and the X-ray crystal structure is shown in FIGS. 1 and 2.

Sample Quality and Data Collection

Example P17 was crystallized from ethyl acetate/cyclohexane. The sample consisted of dry colorless rhombic prisms of up to several mm in length. A block of approx. 0.3×0.3×0.3 mm3 was broken off of a larger one and mounted in NVH oil for data collection. Diffraction data were collected at 100K to a resolution of 0.9 Å. The quality of the x-ray data was excellent, with an Rmerge value of 1.8 (see Appendix A). Structure solution and refinement were straightforward, resulting in a model with very good quality indices (R1=3.5%).

Structure

The Example P17 crystals belonged to the non-centrosymmetric space group P212121 with one molecule per asymmetric unit (FIG. 1, see FIG. 2 for the numbering scheme). The crystals were enantiopure as expected. All atoms were crystallographically well defined, with no sign of disorder or anisotropic movement. For technical reasons, the numbering scheme used in these structures does not correspond to systematic nomenclature.

Stereochemistry

The absolute configuration of Example P17 could be determined with a high degree of accuracy (Flack parameter 0.00+/−0.02). The absolute structure of Example P17 is given in below. The systematic name of the compound is (1R,4S)—N-[(1S,2S)-2-(4-chlorophenyl)cyclobutyl]-1,7,7-trimethyl-2-oxo-3-oxabicyclo[2.2.1]heptane-4-carboxamide.

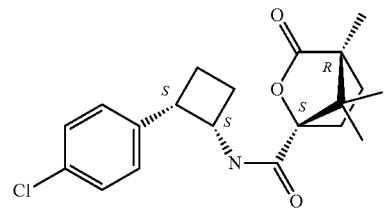

TABLE 57

X-ray data collection and refinement statistics for Example P17

| Crystal parameters | |
|---|---|
| Space group | P212121 |
| Unit cell | a = 6.5229(2) Å |
|  | b = 10.1198(8)Å |
|  | c = 28.4586(12) Å |
| Data collection statistics | |
| Resolution | 0.90 Å |
| # unique reflections | 2664 |
| Rmerge | 1.8% |
| Structure refinement | |
| R1/wR2 | 3.5%/8.5% |
| GooF | 0.997 |
| Refinement target/cutoff | F2/−3.0 L |
| Observable/parameter ratio | 11.6 |
| Min/max difference density | −0.23/+0.21 e−/Å3 |
| Max. shift/esd | 0.0001 |
| Flack parameter | 0.00 +/− 0.02 |
| Scatterers | C20H24Cl1N1O3 |

TABLE 58

Bond lengths and angles for Example P17

| Atoms | | Distance (Å) | Atoms | | | Bond angle (°) |
|---|---|---|---|---|---|---|
| Cl (1) | —C (2) | 1.742 (3) | Cl (1) | —C (2) | —C (3) | 119.5 (2) |
| C (2) | —C (3) | 1.379 (4) | Cl (1) | —C (2) | —C (7) | 119.6 (2) |
| C (2) | —C (7) | 1.375 (4) | C (3) | —C (2) | —C (7) | 120.9 (2) |
| C (3) | —C (4) | 1.384 (4) | C (2) | —C (3) | —C (4) | 119.0 (3) |
| C (4) | —C (5) | 1.385 (3) | C (3) | —C (4) | —C (5) | 121.6 (3) |
| C (5) | —C (6) | 1.398 (3) | C (4) | —C (5) | —C (6) | 117.9 (2) |
| C (5) | —C (8) | 1.494 (3) | C (4) | —C (5) | —C (8) | 119.3 (2) |
| C (6) | —C (7) | 1.381 (4) | C (6) | —C (5) | —C (8) | 122.8 (2) |
| C (8) | —C (9) | 1.570 (3) | C (5) | —C (6) | —C (7) | 121.0 (2) |
| C (8) | —C (25) | 1.550 (3) | C (2) | —C (7) | —C (6) | 119.6 (3) |
| C (9) | —N (10) | 1.443 (3) | C (5) | —C (8) | —C (9) | 114.53 (17) |
| C (9) | —C (24) | 1.530 (3) | C (5) | —C (8) | —C (25) | 118.7 (2) |
| N (10) | —C (11) | 1.337 (3) | C (9) | —C (8) | —C (25) | 86.82 (17) |

TABLE 58-continued
Bond lengths and angles for Example P17
| Atoms | | Distance (Å) | Atoms | | | Bond angle (°) |
|---|---|---|---|---|---|---|
| C (11) | —O (12) | 1.228 (3) | C (8) | —C (9) | —N (10) | 120.16 (18) |
| C (11) | —C (13) | 1.510 (3) | C (8) | —C (9) | —C (24) | 89.93 (17) |
| C (13) | —O (14) | 1.469 (3) | N (10) | —C (9) | —C (24) | 116.96 (19) |
| C (13) | —C (18) | 1.548 (3) | C (9) | —N (10) | —C (11) | 120.51 (19) |
| C (13) | —C (22) | 1.522 (3) | N (10) | —C (11) | —O (12) | 123.1 (2) |
| O (14) | —C (15) | 1.373 (3) | N (10) | —C (11) | —C (13) | 117.75 (19) |
| C (15) | —O (16) | 1.201 (3) | O (12) | —C (11) | —C (13) | 118.99 (19) |
| C (15) | —C (17) | 1.517 (3) | C (11) | —C (13) | —O (14) | 110.39 (17) |
| C (17) | —C (18) | 1.560 (3) | C (11) | —C (13) | —C (18) | 114.37 (18) |
| C (17) | —C (21) | 1.555 (3) | O (14) | —C (13) | —C (18) | 102.03 (16) |
| C (17) | —C (23) | 1.509 (3) | C (11) | —C (13) | —C (22) | 118.14 (18) |
| C (18) | —C (19) | 1.528 (3) | O (14) | —C (13) | —C (22) | 105.69 (17) |
| C (18) | —C (20) | 1.527 (3) | C (18) | —C (13) | —C (22) | 104.69 (17) |
| C (21) | —C (22) | 1.552 (3) | C (13) | —O (14) | —C (15) | 106.31 (16) |
| C (24) | —C (25) | 1.545 (3) | O (14) | —C (15) | —O (16) | 121.8 (2) |
| | | | O (14) | —C (15) | —C (17) | 106.98 (19) |
| | | | O (16) | —C (15) | —C (17) | 131.2 (2) |
| | | | C (15) | —C (17) | —C (18) | 99.02 (17) |
| | | | C (15) | —C (17) | —C (21) | 102.86 (18) |
| | | | C (18) | —C (17) | —C (21) | 102.15 (18) |
| | | | C (15) | —C (17) | —C (23) | 114.7 (2) |
| | | | C (18) | —C (17) | —C (23) | 119.54 (19) |
| | | | C (21) | —C (17) | —C (23) | 115.89 (19) |
| | | | C (13) | —C (18) | —C (17) | 91.66 (16) |
| | | | C (13) | —C (18) | —C (19) | 112.95 (17) |
| | | | C (17) | —C (18) | —C (19) | 114.02 (19) |
| | | | C (13) | —C (18) | —C (20) | 114.35 (19) |
| | | | C (17) | —C (18) | —C (20) | 113.83 (18) |
| | | | C (19) | —C (18) | —C (20) | 109.26 (19) |
| | | | C (17) | —C (21) | —C (22) | 104.28 (18) |
| | | | C (13) | —C (22) | —C (21) | 101.11 (18) |
| | | | C (9) | —C (24) | —C (25) | 88.40 (18) |
| | | | C (8) | —C (25) | —C (24) | 90.15 (17) |
Example P18
N-[(1,2 cis)-2-(2,3-difluorophenyl)cyclobutyl]-2-(trifluoromethyl)benzamide (racemic)
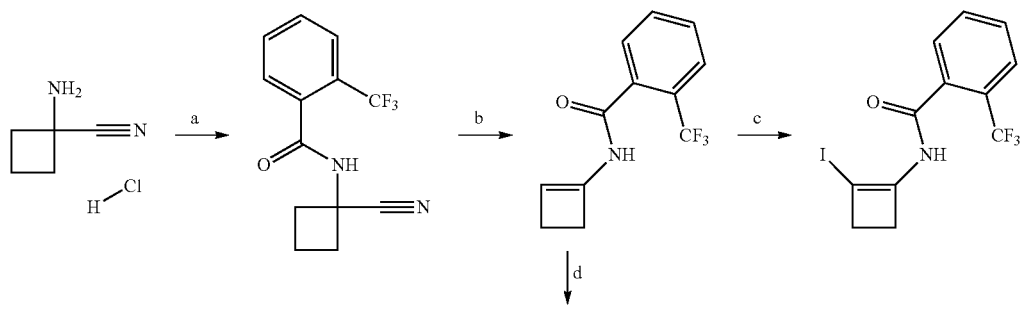
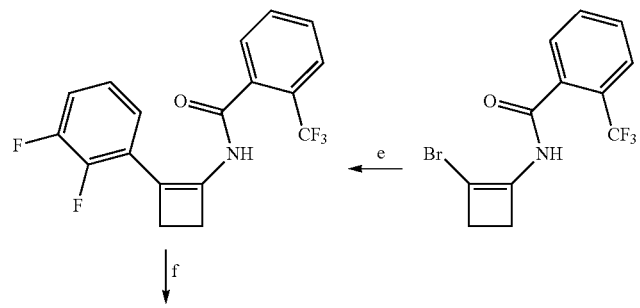

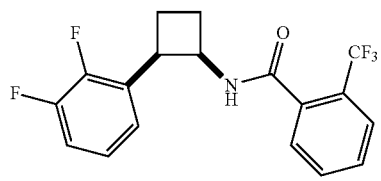

Step a. Preparation of N-(1-cyanocyclobutyl)-2-(trifluoromethyl)benzamide

1-Cyanocyclobutanamine hydrochloride (1 g, 7.54 mmol) was suspended in water (10 ml). Sodium carbonate (1.60 g, 15.1 mmol) was added with stirring followed by 2-(trifluoromethyl)benzoyl chloride (1.57 g, 7.54 mmol). The reaction mixture was stirred for one hour and then shaken between ethyl acetate and 2M HCl, then washed with 2M sodium carbonate, and then with saturated brine. The resulting organic layer was dried over MgSO4 and concentrated. The resulting solid was triturated with cold diethylether to afford pure N-(1-cyanocyclobutyl)-2-(trifluoromethyl)benzamide. Melting point: 148-154° C.
$^1$H NMR (CDCl3, 400 MHz) δ 7.75 (d, J=10 Hz, 1H), 7.60 (m, 3H), 6.15 (br s, 1H), 2.9 (m, 2H), 2.5 (m, 1H), 2.2 (m, 2H) ppm

Step b. Preparation of N-(cyclobuten-1-yl)-2-(trifluoromethyl)benzamide

N-(1-cyanocyclobutyl)-2-(trifluoromethyl)benzamide (268 mg, 1 mmol) was dissolved in dry THF (1 ml) in a dried flask under argon. Sodium tert-butoxide (2M in THF; 0.75 ml, 0.5 mmol) was then added and stirred at room temperature for four days. The reaction was diluted with TBME and then quenched with 1M solution of NaHCO3, followed by a solution of saturated brine. The resulting organic layer was dried over MgSO4, filtered and concentrated to afford the crude material (245 mg), which was chromatographed on silica to obtain pure N-(cyclobuten-1-yl)-2-(trifluoromethyl)benzamide.

Melting point: 129-133° C.
$^1$H NMR (CDCl3, 400 MHz) δ 7.75 (d, J=10 Hz, 1H), 7.6 (m, 3H), 7.15 (br s, 1H), 5.6 (s, 1H), 2.8 (m, 2H), 2.45 (m, 2H) ppm

Step c. Preparation of N-(2-iodocyclobuten-1-yl)-2-(trifluoromethyl)benzamide N-(cyclobuten-1-yl)-2-(trifluoromethyl)benzamide (15 mg, 0.0622 mmol) was dissolved in dichloromethane (0.200 ml). Triethylamine (0.0105 ml, 0.0746 mmol, 7.63 mg) was added. Under stirring N-iodosuccinimide (14.4 mg, 0.0622 mmol) was added. It dissolved quickly. TLC (50% EtOAc/cyclohexane) after 10 minutes at RT showed complete reaction. The reaction mixture was shaken between TBME and 1M NaHCO3, dried over MgSO4, and evaporated. Chromatography on silica with a 0 to 50% EtOAc/cyclohexane gradient gave pure N-(2-iodocyclobuten-1-yl)-2-(trifluoromethyl)benzamide.

1H-NMR (CDCl3) 2.78 (2H, t); 3.42 (2H, t); 7.20 (br s, NH); 7.61 (3H, m); 7.73 (1H, s).

Step d. Preparation of N-(2-bromocyclobuten-1-yl)-2-(trifluoromethyl)benzamide N-(cyclobuten-1-yl)-2-(trifluoromethyl)benzamide (3.86 g, 16 mmol) was stirred in dichloromethane (ca 30 ml) at ca 10° C. Na2CO3 (2M aq., ca 20 ml) was added and Hünigs's base (2.09 g, 16 mmol, 2.82 ml) was added, followed by N-bromosuccinimide (2.85 g). The organic phase was then dried with MgSO4, and evaporated to give the crude product, which was chromatographed on silica (120 g) with a gradient of 0 to 50% EtOAc in cyclohexane to yield N-(2-bromocyclobuten-1-yl)-2-(trifluoromethyl)benzamide. M.p. 112-113-5° C.

$^1$H NMR (300 MHz, CDCl3) δ 7.74 (d, 1H), 7.60 (m, 3H), 7.28 (br s, 1H), 3.21 (t, 2H), 2.78 (t, 2H) ppm

Step e. N-[2-(2,3-difluorophenyl)cyclobuten-1-yl]-2-(trifluoromethyl)benzamide To a solution of N-(2-bromocyclobuten-1-yl)-2-(trifluoromethyl)benzamide (50 mg, 150 µmol) in THF (2.25 ml) were added successively 2,3-difluoro-phenylboronic acid (300 µmol), a solution of potassium phosphate (65.6 mg) in water (0.75 ml) and chloro(2-dicyclohexylphosphino-2',4',6'-thisopropyl-1,1'-biphenyl)[2-(2'-amino-1,1-biphenyl)]palladium(II) (12 mg; 15 µmol). The reaction mixture was flushed with argon and stirred at 110° C. for 30 minutes in a microwave oven. Then the THF was evaporated. The crude mixture was diluted with water (10 ml) and extracted with ethyl acetate (3×10 ml). The organic phase was washed with brine, dried over Na2SO4, filtrated and evaporated. The crude material was purified via column chromatography using cyclohexane and AcOEt as eluants. The desired product was isolated as white crystals.

$^1$H NMR (400 MHz, CDCl3): 8.12 (br. d, 1H), 7.77 (d, 1H), 7.68-7.59 (m, 3H), 7.09-6.96 (m, 2H), 6.92 (t, 1H), 3.28 (t, 2H), 2.68 (t, 2H).

Step f. N-[(1,2 cis)-2-(2,3-difluorophenyl)cyclobutyl]-2-(trifluoromethyl)benzamide (racemic)

To a solution of N-[2-(2,3-difluorophenyl)cyclobuten-1-yl]-2-(trifluoromethyl)benzamide. (33 mg, 0.0915 mmol) in methanol (2 ml) was added (1,1'-bis(di-1-propylphosphino)ferrocene (1,5'-cyclooctadiene)rhodium (I) tetrafluoroborate (4 mg, 5.5 µmol) under inert atmosphere. The reaction mixture was placed in a stainless steel autoclave and was hydrogenated at 50 bar and ambient temperature for 22 hours. The crude mixture was concentrated and purified via column chromatography using cyclohexane and AcOEt as eluants. The desired product was isolated as white crystals.

1H-NMR (CDCl3, 400 MHz): 7.61 (m, 1H), 7.52-7.45 (m, 2H), 7.21 (d, 1H), 7.13-7.06 (m, 3H), 5.55 (br. d, 1H), 5.07 (quintet, 1H), 4.24 (q, 1H), 2.64 (m, 1H), 2.44-2.29 (m, 2H), 2.16 (m, 1H).

This method was used to prepare Compound No. 60-247 and 60-248.

Example P19

Preparation of
N-(cyclobuten-1-yl)-2-(trifluoromethyl)benzamide

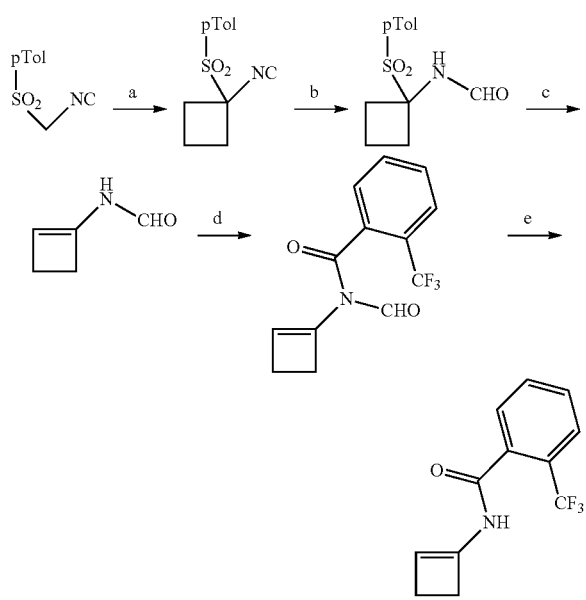

Step a. Preparation of 1-isocyano-1-(4-methylphenyl)sulfonyl-cyclobutane

Sodium hydride (3.1 g, 57% in oil, 74 mmol) was washed with hexane under argon. A mixture of DMSO and diethyl ether (3:1, 50 ml) was added. This was stirred well and a solution of 1,3-dibromopropane (3.1 ml, 6.1 g, 31 mmol) and 1-(isocyanomethylsulfonyl)-4-methyl-benzene (5.0 g, 26 mmol) in a mixture of DMSO and diethyl ether (3:1, 30 ml) was added dropwise, causing an exotherm to 43° C. The addition took about 30 minutes. After one hour stirring a precipitate of NaBr came out, and the temperature sank to room temperature. Water (60 ml) was slowly added, and the crude mixture extracted with diethylether, which was then dried over Na2SO4 and evaporated down to give the crude material. This was stirred with ether, cooled in an ice bath, and the crystals filtered off to yield 1-isocyano-1-(4-methylphenyl)sulfonyl-cyclobutane as light coloured crystals.
M.p. 94-97° C.

Step b. Preparation of N-(1-(4-methylphenyl)sulfonylcyclobutyl)formamide

Hydrochloric acid (19 ml, 2M, 36 mmol) as added to a solution of 1-(1-isocyanocyclobutyl)sulfonyl-4-methyl-benzene (8.5 g, 36 mmol) in THF (50 ml) at 0-5° C. which was cooled in an ice-water bath. After TLC in 50% EtOAc in hexane showed complete reaction, NaHCO3 (1M) was added to make the mixture lightly basic. The mixture was extracted with TBME, dried over Na2SO4, and evaporated to give the crude product, which was stirred in ether and left in the refrigerator at ca 0 to 5° C. The resulting solid was filtered off to yield N-(1-(4-methylphenyl)-sulfonyl-cyclobutyl)formamide as beige crystals.
M.p. 83-88° C.

Step c. Preparation of N-(cyclobuten-1-yl)formamide

A solution of N-[1-(p-tolylsulfonyl)cyclobutyl]formamide (500 mg, 1.97 mmol) in THF (3 ml) was cooled to 0° C. under argon. A solution of sodium butoxide in THF (2.96 ml, 2M, 5.92 mmol, 3 equiv.) was added slowly. After 30 minutes at 0° C. the mixture was extracted between diethylether and NaHCO3 (aq). The ether phase was evaporated to yield N-(cyclobuten-1-yl)formamide as an oil. 1H-NMR showed a mixture of rotamers.

$^1$H NMR (300 MHz, CDCl$_3$) δ 8.33 (d, 1H), 8.19 (s, 1H), 5.45 (s, 1H), 5.05 (s, 1H), 2.73 (m, 2H), 2.38 (m, 2H).

Step d. Preparation of N-(cyclobuten-1-yl)-N-formyl-2-(trifluoromethyl)benzamide A solution of N-(cyclobuten-1-yl)formamide (190 mg, 1.956 mmol) in ether and THF as a solution obtained as above before evaporation was cooled to 0° C. Triethylamine (300 mg, 2.935 mmol) and DMAP (23.9 mg, 0.1956 mmol) were added then 2-(trifluoromethyl)benzoyl chloride (449 mg, 2.152 mmol) was added dropwise. There was an exotherm to 7° C. and a precipitate came out of solution. The cool bath was removed and the mixture stirred for 2 hours then shaken between EtOAc and NaHCO3 (aq.), washed with brine, dried over Na2SO4, and evaporated to give N-(cyclobuten-1-yl)-N-formyl-2-(trifluoromethyl)benzamide as a crude product $^1$H NMR (300 MHz, CDCl$_3$) δ 8.88 (s, 1H), 5.82 (s, 1H), 2.83 (t, 2H), 2.38 (t, 2H)

Step e. Preparation of N-(cyclobuten-1-yl)-2-(trifluoromethyl)benzamide

N-(cyclobuten-1-yl)-N-formyl-2-(trifluoromethyl)benzamide (63 mg, 0.26 mmol) was dissolved in THF (1 ml) and cooled to 0° C. NaOH (2M, 1.2 equiv.) was added and stirred for 30 min at 0° C., then shaken between EtOAc and water, dried over Na2SO4, and evaporated to yield crude N-(cyclobuten-1-yl)-2-(trifluoromethyl)benzamide $^1$H NMR (CDCl3, 400 MHz) δ 7.75 (d, J=10 Hz, 1H), 7.6 (m, 3H), 7.15 (br s, 1H), 5.6 (s, 1H), 2.8 (m, 2H), 2.45 (m, 2H) ppm

Example P20

Preparation of N-(2-iodocyclobuten-1-yl)formamide

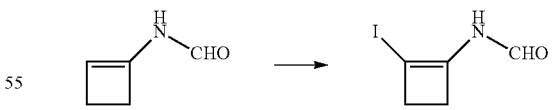

A solution of N-(cyclobuten-1-yl)formamide (82 mg, 0.8443 mmol) in ether and THF prepared as described above in example P3 was cooled to 0° C. A solution of K2CO3 (0.844 ml, 1.689 mmol, 2M, aq.) was added and Hünig's base (109 mg, 0.8443 mmol) was added. Under stirring iodine (214 mg, 0.8443 mmol) was added. After performing a TLC examination with 50% EtOAc/cyclohexane the mixture was shaken between EtOAc and water, washed with NaS2O3 (aq.), then HCl (aq), then NaHCO3 (aq), then brine. It was dried over Na2SO4, and evaporated to give crude product, which was chromatographed on silica with EtOAc/cyclohexane to yield N-(2-iodocyclobuten-1-yl)formamide ¹H NMR (CDCl3, 400 MHz, mixture of two rotamers) δ 8.43 (d, 1H), 8.18 (s, 1H), 3.30 (t, 2H), 3.00 (t, 2H), 2.74 (m, 2H).

Example P21

Preparation
N-(cyclobuten-1-yl)-4-methoxy-benzamide

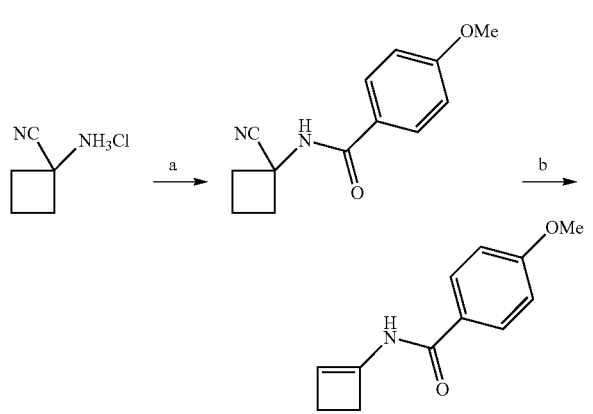

Step a. Preparation of
N-(1-cyanocyclobutyl)-4-methoxy-benzamide

1-Cyanocyclobutanamine chloride (200 mg, 1.5084 mmol) was dissolved in THF, the solution was then cooled down to 0° C. Triethylamine (305 mg, 3.0168 mmol) was then added and stirred for 15 min. 4-methoxybenzoyl chloride (257 mg, 1.5084 mmol) was then added and the reaction mixture warmed up to room temperature. After 17 hours the mixture is a suspension. It was shaken between EtOAc and water, washed with NaHCO3 (1 M, aq) and brine, dried over MgSO4 and evaporated to yield 255 mg of crude product, which was chromatographed on silica with EtOAc/cyclohexane to afforded N-(1-cyanocyclobutyl)-4-methoxy-benzamide as a white solid.

1H NMR (CDCl3, 400 MHz) δ 7.75 (d, J=10 Hz, 2H), 6.95 (d, J=10 Hz, 2H), 6.38 (br s, 1H), 2.9 (m, 2H), 2.5 (m, 1H), 2.3 (m, 1H), 2.15 (m, 1H)

Step b. Preparation of
N-(cyclobuten-1-yl)-4-methoxy-benzamide

A solution of sodium tert-butoxide in THF (0.938 ml, 2M, 1.876 mmol) was added to a solution of N-(1-cyanocyclobutyl)-4-methoxy-benzamide (144 mg, 0.6253 mmol) in THF (3 ml). After 24 hours at RT the mixture was shaken between TBME and NaHCO3 (1 M, aq.), dried over MgSO4 and the solvent evaporated to afford crude product, which was chromatographed on silica to afford N-(cyclobuten-1-yl)-4-methoxy-benzamide as a white solid.

M.p. 79-85° C.

¹H NMR (CDCl₃, 400 MHz) δ 7.75 (d, J=10 Hz, 2H), 7.5 (br s, 1H), 6.95 (d, J=10 Hz, 2H), 3.85 (s, 3H), 2.8 (m, 2H), 2.45 (m, 2H).

Example P22

Preparation N-(cyclobuten-1-yl)acetamide

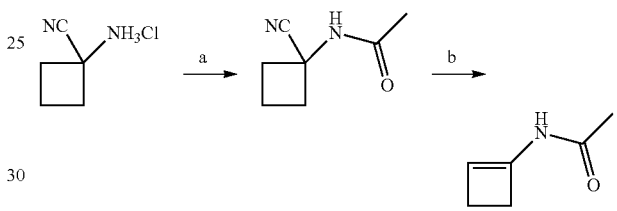

Step a. Preparation of
N-(1-cyanocyclobutyl)acetamide

Prepared according to example P21 step a to afford N-(1-cyanocyclobutyl)acetamide as a brown solid. Melting point: 70-72° C.

1H NMR (CDCl3, 400 MHz) δ 5.85 (br s, 1H), 2.7 (m, 2H), 2.3 (m, 2H), 2.15 (m, 1H), 2.05 (m, 1H), 1.95 (s, 3H)

Step b. Preparation of
N-(cyclobuten-1-yl)acetamide

Prepared according to example P21 step b to afford N-(cyclobuten-1-yl)acetamide as a pale yellow solid.

1H NMR (CDCl3, 400 MHz) δ 6.98 (br s, 1H), 5.40 (s, 1H), 2.68 (t, 2H), 2.48 (m, 2H), 2.01 (s 3H)

Example P23

Preparation of N-[(2-(4-chlorophenyl)cyclobuten-1-yl]-2-(trifluoromethyl)benzamide

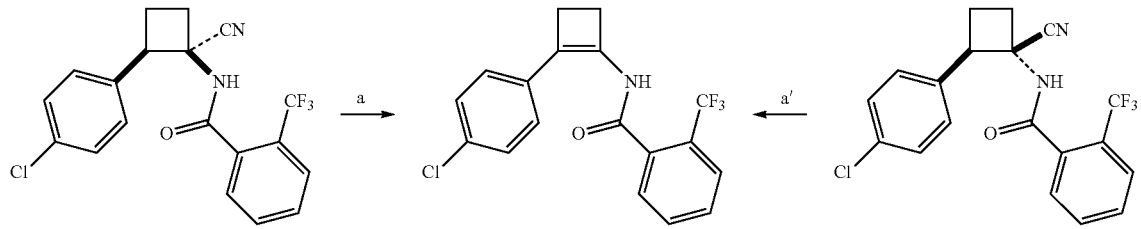 [SMILES: N#C[C@@]1(NC(=O)c2ccccc2C(F)(F)F)CC[C@@H]1c1ccc(Cl)cc1 ; O=C(NC1=C(c2ccc(Cl)cc2)CC1)c1ccccc1C(F)(F)F ; N#C[C@]1(NC(=O)c2ccccc2C(F)(F)F)CC[C@@H]1c1ccc(Cl)cc1]

Step a. Preparation of N-[(2-(4-chlorophenyl)cy-clobuten-1-yl]-2-(trifluoromethyl)benzamide A solution of racemic N-[(1,2 cis)-2-(4-chlorophenyl)-1-cyano-cyclobutyl]-2-(trifluoromethyl)benzamide (8 mg, 0.021 mmol) in THF was treated with a solution of sodium tert-butoxide (2M in THF; 0.211 ml, 0.422 mmol), and heated to 40° C. After 23 hours at 40° C., the reaction mixture was shaken between TBME and 1M NaHCO3 (aq), washed with brine, dried over MgSO4 and concentrated to give N-[2-(4-chlorophenyl)cyclobuten-1-yl]-2-(trifluoromethyl)benzamide, the NMR signals of which are identical to those described in example P4.

Step a'. Preparation of N-[(2-(4-chlorophenyl)cy-clobuten-1-yl]-2-(trifluoromethyl)benzamide From racemic N-[(1,2 trans)-2-(4-chlorophenyl)-1-cyano-cyclobutyl]-2-(trifluoromethyl)benzamide,
N-[2-(4-chlorophenyl)cyclobuten-1-yl]-2-(trifluoromethyl)benzamide was prepared according to the procedure described above for step a.

Example P24

Preparation of N-[2-(2,4-difluorophenyl)cyclobuten-1-yl]acetamide

Step a. Preparation of racemic (1,2 cis)-1-amino-2-(2,4-difluorophenyl)cyclobutanecarbonitrile and racemic (1,2 trans)-1-amino-2-(2,4-difluorophenyl)cyclobutanecarbonitrile A solution of 2-(2,4-difluorophenyl)cyclobutanone (1.2 g, 6.59 mmol) in methanol (20 ml) was treated under stirring under argon with ammonium acetate (762 mg, 9.88 mmol), then acetic acid (1.19 g, 19.76 mmol), then sodium cyanide (484 mg, 9.88 mmol), causing an exotherm to 28° C. After stirring overnight at 60° C., the mixture was shaken between TBME and 1M NaHCO3 (aq), then brine, then dried with Na2SO4, and the solvent evaporated to give 1.3 g of the crude mixture of products as a dark oil, which was chromatographed on silica with EtOAc/cyclohexane to yield racemic (1,2 cis)-1-amino-2-(2,4-difluorophenyl)cyclobutanecarbonitrile and racemic (1,2 trans)-1-amino-2-(2,4-difluorophenyl)cyclobutanecarbonitrile as oils.

racemic (1,2 cis)-1-amino-2-(2,4-difluorophenyl)cyclobutanecarbonitrile: $^1$H NMR (400 MHz, CDCl3) δ ppm 1.43 (br s, 2H), 2.05 (m, 1H), 2.31 (m, 1H), 2.67 (m, 2H), 4.12 (t, 1H), 6.84 (m, 1H), 6.92 (m, 1H), 7.26 (m, 1H)

racemic (1,2 trans)-1-amino-2-(2,4-difluorophenyl)cyclobutanecarbonitrile: $^1$H NMR (400 MHz, CDCl3) δ ppm 2.09 (br s, 2H), 2.13 (m, 2H), 2.23 (m, 1H), 2.57 (m, 1H), 3.73 (t, 1H), 6.85 (m, 1H), 6.92 (m, 1H), 7.24 (m, 1H).

Step b. Preparation of racemic N-[(1,2 cis)-1-cyano-2-(2,4-difluorophenyl)cyclobutyl]acetamide A solution of racemic (1,2 cis)-1-amino-2-(2,4-difluorophenyl)cyclobutanecarbonitrile (60 mg, 0.288 mmol) in 0.5 ml EtOAc was stirred with K2CO3 (79.7 mg, 0.576 mmol) and acetic anhydride (58.8 mg, 0.576 mmol) was added. The mixture was stirred for 3 days at room temperature then shaken between MTBE and water, dried and evaporated to yield racemic N-[(1,2 cis)-1-cyano-2-(2,4-difluorophenyl)cyclobutyl]acetamide as an oil.

$^1$H NMR (400 MHz, CDCl3) δ ppm 1.88 (s, 3H), 2.38 (m, 1H), 2.54 (m, 2H), 2.80 (m, 1H), 4.38 (t, 1H), 5.26 (br s, 1H), 6.92 (m, 1H), 6.98 (m, 1H), 7.26 (m, 1H).

Step c. Preparation of N-[2-(2,4-difluorophenyl)cyclobuten-1-yl]acetamide

A solution of racemic N-[(1,2 cis)-1-cyano-2-(2,4-difluorophenyl)cyclobutyl]acetamide (42 mg, 0.168 mmol) in THF (1 ml) was treated with a solution of sodium butoxide (2M in THF; 0.282 ml, 0.503 mmol) and the mixture heated overnight at 60° C. The mixture was then shaken between

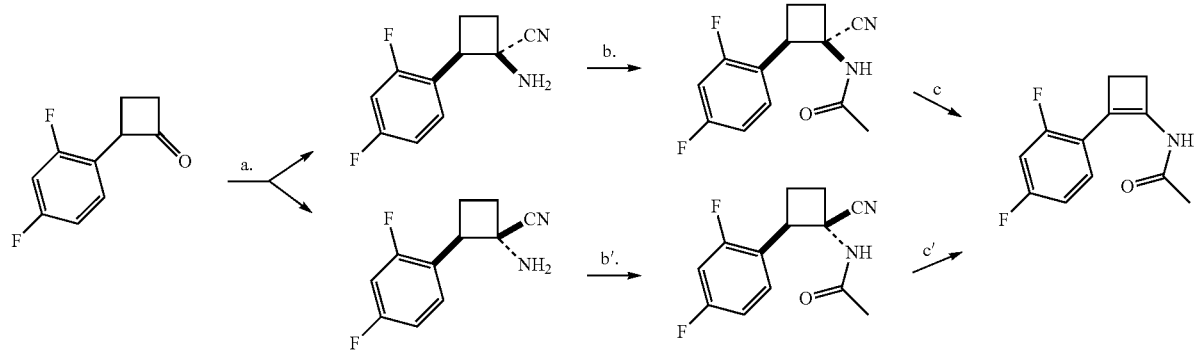

MTBE and brine, dried over Na2SO4, and the solvent evaporated to yield N-[2-(2,4-difluorophenyl)cyclobuten-1-yl]acetamide as beige crystals. M.p. 137-140° C.; NMR signals identical to those described in example P7, step d2.

Step b'. Preparation of racemic (1,2 trans)-1-amino-2-(2,4-difluorophenyl)cyclobutanecarbonitrile From racemic (1,2 trans)-1-amino-2-(2,4-difluorophenyl)cyclobutanecarbonitrile, racemic (1,2 trans)-1-amino-2-(2,4-difluorophenyl)cyclobutanecarbonitrile was prepared according to the procedure described in step b. M.p. 170-173° C.

$^1$H NMR (400 MHz, CDCl3) δ ppm 2.03 (s, 3H), 2.31 (m, 1H), 2.43 (m, 1H), 2.52 (m, 1H), 2.90 (m, 1H), 3.96 (t, 1H), 6.18 (br s, 1H), 6.88 (m, 1H), 6.98 (m, 1H), 7.33 (m, 1H).

Step c'. Preparation of N-[(2-(2,4-difluorophenyl)cyclobuten-1-yl]acetamide

From racemic (1,2 trans)-1-amino-2-(2,4-difluorophenyl)cyclobutanecarbonitrile, N-[2-(2,4-difluorophenyl)cyclobuten-1-yl]acetamide was prepared according to the procedure described in step c. The NMR signals were identical to those described in example P7, step d2.

Table 59: Compounds of Formula (XIIa)

Table 59 shows selected melting point, selected HPLC-MS, and selected NMR data for compounds of formula (XIIa) (or their hydrochloride salt) of the present invention. $CDCl_3$ was used as the solvent for NMR measurements, unless otherwise stated. No attempt is made to list all characterising data in all cases.

In Table 59 and throughout the description, temperatures are given in degrees Celsius; "NMR" means nuclear magnetic resonance spectrum; HPLC is high pressure liquid chromatography; MS stands for mass spectrum; "%" is percent by weight, unless corresponding concentrations are indicated in other units. The following abbreviations are used throughout this description:

m.p.=melting point [° C.] b.p.=boiling point.
S=singlet br=Broad
d=doublet dd=doublet of doublets
t=triplet q=Quartet
m=multiplet ppm=parts per million Table 60: Compounds of Formula (II)

Table 60 shows selected melting point, selected HPLC-MS, and selected NMR data for compounds of formula (II) of the present invention. $CDCl_3$ was used as the solvent for NMR measurements, unless otherwise stated. No attempt is made to list all characterising data in all cases.

Table 61: Compounds of Formula (I)

Table 61 shows selected melting point, selected HPLC-MS for compounds of formula (I) of the present invention. No attempt is made to list all characterising data in all cases.

RT refers to the retention time of the HPLC-MS method and RT' refers to the retention time of the desired enantiomer in the chiral HPLC method.

All the compounds from Table 61 were obtained through the enantioselective reduction of an enamide intermediate as described in the previous example protocols except compounds 100, 101, 102, 155, 156, 175 and 176 which were obtained through the resolution of racemates via preparative chiral HPLC.

Table 62: Compounds of Formula (XXXIII)

Table 62 shows selected melting point, selected HPLC-MS, and selected NMR data for compounds of formula (XXXIII) of the present invention. No attempt is made to list all characterising data in all cases.

NMR 59.27
δ (in ppm, 400 MHz, $CDCl_3$): 7.59 (1H, d); 7.35 (2H, m); 7.12 (1H, m); 3.98 (2H, m); 2.39 (2H, m), 2.20 (1H, m); 1.68 (1H, m); 1.42 (2H, br s)

NMR 60.13:
δ (in ppm, 400 MHz, $CDCl_3$): 2.11 (IH, m); 2.30 (2H, m); 2.61 (IH, m); 4.15 (IH, m); 5.02 (IH, m); 5.53 (1H, br d); 4.10 (1H, d); 7.10 (IH, m); 7.17 (2H, m); 7.27 (1H, m); 7.47 (2H, m); 7.61 (IH, d).

NMR 60.234:
δ (in ppm, 400 MHz, $CDCl_3$): 4.51 (1H, dd); 5.18 (1H, dd); 5.50 (1H, ddd); 5.69 (1H, br d); 6.08 (1H, d); 6.90 (1H, d); 7.35-7.77 (7H, m).

TABLE 59

| Entry | Name | RT (min) | [M + H] (measured) | Method | MP (° C.) |
|---|---|---|---|---|---|
| 59.1 | (1,2 cis)-2-(2,4-dichlorophenyl)cyclobutanamine hydrochloride | | | | 227-231 |
| 59.2 | (1,2 cis)-2-(2,4-dichloro-6-isopropoxy-phenyl)cyclobutanamine hydrochloride | | | | 70-73 |
| 59.3 | (1,2 cis)-2-(2,4-difluorophenyl)cyclobutanamine hydrochloride | | | | 242 |
| 59.4 | (1,2 cis)-2-[2-fluoro-4-(trifluoromethyl)phenyl]cyclobutanamine hydrochloride | | | | 239 |
| 59.5 | (1,2 cis)-2-[2-chloro-4-(trifluoromethyl)phenyl]cyclobutanamine hydrochloride | | | | 256 |
| 59.6 | (1,2 cis)-2-(3-chlorophenyl)cyclobutanamine hydrochloride | | | | 206-208 |
| 59.7 | (1,2 cis)-2-(3-bromophenyl)cyclobutanamine hydrochloride | | | | 217 |
| 59.8 | (1,2 cis)-2-(2,5-dichlorophenyl)cyclobutanamine hydrochloride | | | | 209 |
| 59.9 | (1,2 cis)-2-(3,4-dichlorophenyl)cyclobutanamine hydrochloride | | | | 239 |
| 59.10 | (1,2 cis)-2-(2-chlorophenyl)cyclobutanamine hydrochloride | | | | 240 |
| 59.11 | (1,2 cis)-2-(3,5-dichlorophenyl)cyclobutanamine hydrochloride | | | | 260-262 |
| 59.12 | (1,2 cis)-2-(2,6-dichlorophenyl)cyclobutanamine hydrochloride | | | | 217 |
| 59.13 | (1,2 cis)-2-(4-isopropoxyphenyl)cyclobutanamine hydrochloride | | | | 259-262 |
| 59.14 | (1,2 cis)-2-(2,3-dichlorophenyl)cyclobutanamine hydrochloride | | | | 249-252 |
| 59.15 | (1,2 cis)-2-(4-methylsulfonylphenyl)cyclobutanamine hydrochloride | | | | 251 |
| 59.16 | (1,2 cis)-2-(2,4-dichloro-6-methoxy-phenyl)cyclobutanamine hydrochloride | | | | 237-239 |
| 59.17 | (1,2 cis)-2-(2,4,6-trichlorophenyl)cyclobutanamine hydrochloride | | | | 262 |
| 59.18 | (1,2 cis)-2-(4-fluorophenyl)cyclobutanamine hydrochloride | 0.38 | 166 | G | |
| 59.19 | (1,2 cis)-2-(4-chlorophenyl)cyclobutanamine hydrochloride | 0.52 | 182 | B | |
| 59.20 | (1,2 cis)-2-(4-bromophenyl)cyclobutanamine hydrochloride | 0.53 | 226 | B | |
| 59.21 | (1,2 cis)-2-(2-bromo-4-fluoro-phenyl)cyclobutanamine | 0.52 | 244 | B | |
| 59.22 | (1,2 cis)-2-(4-bromo-2-fluoro-phenyl)cyclobutanamine | 0.54 | 244 | B | |
| 59.23 | (1,2 cis)-2-(2-fluorophenyl)cyclobutanamine | 0.36 | 166 | B | |
| 59.24 | (1,2 cis)-2-(4-bromo-2-chloro-phenyl)cyclobutanamine | 0.84 | 260 | G | |
| 59.25 | (1,2 cis)-2-[4-[3-(trifluoromethyl)pyrazol-1-yl]phenyl]cyclobutanamine hydrochloride | 0.97 | 282 | G | |
| 59.26 | (1,2 cis)-2-(2,4,6-trifluorophenyl)cyclobutanamine | 0.53 | 202 | B | |
| 59.27 | (1,2 cis)-2-(2-bromophenyl)cyclobutanamine | | | | |

TABLE 60

| Entry | Name | RT (min) | [M + H] (measured) | Method | MP (° C.) |
|---|---|---|---|---|---|
| 60.1 | 2,6-difluoro-N-[(1,2 cis)-2-[4-(trifluoromethoxy)phenyl]cyclobutyl]benzamide | | | | 110-112 |
| 60.2 | 3-(difluoromethyl)-1-methyl-N-[(1,2 cis)-2-[4-(trifluoromethoxy)phenyl]cyclobutyl]pyrazole-4-carboxamide | | | | 120-123 |
| 60.3 | N-[(1,2 cis)-2-[4-(trifluoromethoxy)phenyl]cyclobutyl]-2-(trifluoromethyl)benzamide | | | | 128-131 |
| 60.4 | N-[(1,2 cis)-2-(4-chlorophenyl)cyclobutyl]-2,6-difluorobenzamide | | | | 138-140 |
| 60.5 | N-[(1,2 cis)-2-(4-chlorophenyl)cyclobutyl]-2-(trifluoromethyl)benzamide | | | | 147-149 |
| 60.6 | N-[(1,2 cis)-2-(4-chlorophenyl)cyclobutyl]-2-(trifluoromethyl)pyridine-3-carboxamide | | | | 120-123 |
| 60.7 | N-[(1,2 cis)-2-(2,4-dichlorophenyl)cyclobutyl]-2,6-difluorobenzamide | | | | 124-126 |
| 60.8 | N-[(1,2 cis)-2-(2,4-dichlorophenyl)cyclobutyl]-2-(trifluoromethyl)benzamide | | | | 126-128 |
| 60.9 | N-[(1,2 cis)-2-(2,4-dichlorophenyl)cyclobutyl]-2-(trifluoromethyl)pyridine-3-carboxamide | | | | 157-159 |
| 60.10 | N-[(1,2 cis)-2-(2,4-dichlorophenyl)cyclobutyl]pyrimidine-2-carboxamide | | | | 148-149 |
| 60.11 | N-[(1,2 cis)-2-(4-chlorophenyl)cyclobutyl]pyrimidine-2-carboxamide | 1.29 | 288 | A | |
| 60.12 | N-[(1,2 cis)-2-(4-chloro-2-fluorophenyl)cyclobutyl]-2,6-difluorobenzamide | | | | 126-129 |
| 60.13 | N-[(1,2 cis)-2-(4-chloro-2-fluorophenyl)cyclobutyl]-2-(trifluoromethyl)benzamide | | | | |
| 60.14 | N-[(1,2 cis)-2-[4-(difluoromethoxy)phenyl]cyclobutyl]-2,6-difluorobenzamide | 1.71 | 354 | A | |
| 60.15 | N-[(1,2 cis)-2-[4-(difluoromethoxy)phenyl]cyclobutyl]-2-(trifluoromethyl)benzamide | 1.78 | 386 | A | |
| 60.16 | 2-chloro-N-[(1,2 cis)-2-(4-chlorophenyl)cyclobutyl]pyridine-3-carboxamide | | | | 98-101 |
| 60.17 | N-[(1,2 cis)-2-(4-chlorophenyl)cyclobutyl]-2-fluoropyridine-3-carboxamide | | | | 86-89 |
| 60.18 | N-[(1,2 cis)-2-(4-chlorophenyl)cyclobutyl]-3-(trifluoromethyl)pyridine-2-carboxamide | | | | 115-116 |
| 60.19 | N-[(1,2 cis)-2-(4-chlorophenyl)cyclobutyl]-3-fluoropyridine-2-carboxamide | | | | 80-82 |
| 60.20 | 3-chloro-N-[(1,2 cis)-2-(4-chlorophenyl)cyclobutyl]pyrazine-2-carboxamide | | | | 138-141 |
| 60.21 | N-[(1,2 cis)-2-(4-chlorophenyl)cyclobutyl]-3-(trifluoromethyl)pyrazine-2-carboxamide | | | | 156-158 |
| 60.22 | 3-chloro-N-[(1,2 cis)-2-(4-chlorophenyl)cyclobutyl]pyridine-2-carboxamide | | | | 122-124 |
| 60.23 | N-[(1,2 cis)-2-(2,4-dichlorophenyl)cyclobutyl]-3-(trifluoromethyl)pyridine-2-carboxamide | | | | 109-111 |
| 60.24 | N-[(1,2 cis)-2-(2,4-dichlorophenyl)cyclobutyl]-2-fluoropyridine-3-carboxamide | | | | 96-102 |
| 60.25 | 2-chloro-N-[(1,2 cis)-2-(2,4-dichlorophenyl)cyclobutyl]pyridine-3-carboxamide | | | | 124-128 |
| 60.26 | N-[(1,2 cis)-2-(2,4-dichlorophenyl)cyclobutyl]-3-fluoropyridine-2-carboxamide | | | | 119-121 |
| 60.27 | 3-chloro-N-[(1,2 cis)-2-(2,4-dichlorophenyl)cyclobutyl]pyrazine-2-carboxamide | | | | 92-94 |
| 60.28 | N-[(1,2 cis)-2-(2,4-dichlorophenyl)cyclobutyl]-3-(trifluoromethyl)pyrazine-2-carboxamide | | | | 141-143 |
| 60.29 | 3-chloro-N-[(1,2 cis)-2-(2,4-dichlorophenyl)cyclobutyl]pyridine-2-carboxamide | | | | 82-84 |
| 60.30 | 2,6-difluoro-N-[(1,2 cis)-2-(4-fluorophenyl)cyclobutyl]benzamide | | | | 134-135 |
| 60.31 | N-[(1,2 cis)-2-(4-fluorophenyl)cyclobutyl]-2-(trifluoromethyl)benzamide | | | | 143-144 |
| 60.32 | N-[(1,2 cis)-2-(4-bromophenyl)cyclobutyl]-2,6-difluorobenzamide | | | | 137-138 |
| 60.33 | N-[(1,2 cis)-2-(4-bromophenyl)cyclobutyl]-2-(trifluoromethyl)benzamide | | | | 144-145 |
| 60.34 | N-[(1,2 cis)-2-(4-fluorophenyl)cyclobutyl]-2-(trifluoromethyl)pyridine-3-carboxamide | | | | 156-157 |
| 60.35 | N-[(1,2 cis)-2-(4-bromophenyl)cyclobutyl]-2-(trifluoromethyl)pyridine-3-carboxamide | | | | 139-140 |
| 60.36 | N-[(1,2 cis)-2-(4-cyclopropylphenyl)cyclobutyl]-2-(trifluoromethyl)pyridine-3-carboxamide | | | | 157-158 |
| 60.37 | N-[(1,2 cis)-2-(4-cyanophenyl)cyclobutyl]-2-(trifluoromethyl)pyridine-3-carboxamide | | | | 170-174 |
| 60.38 | N-[(1,2 cis)-2-(2,4-dichlorophenyl)cyclobutyl]-2-(trifluoromethyl)pyridine-3-carboxamide | | | | 72-77 |
| 60.39 | N-[(1,2 cis)-2-(4-fluorophenyl)cyclobutyl]-3-(trifluoromethyl)pyridine-2-carboxamide | | | | 111-114 |
| 60.40 | 3-chloro-N-[(1,2 cis)-2-(4-fluorophenyl)cyclobutyl]pyridine-2-carboxamide | | | | 95-98 |
| 60.41 | 3-fluoro-N-[(1,2 cis)-2-(4-fluorophenyl)cyclobutyl]pyridine-2-carboxamide | | | | 75-80 |
| 60.42 | 3-chloro-N-[(1,2 cis)-2-(4-fluorophenyl)cyclobutyl]pyrazine-2-carboxamide | | | | 131-132 |
| 60.43 | N-[(1,2 cis)-2-(4-fluorophenyl)cyclobutyl]-3-(trifluoromethyl)pyrazine-2-carboxamide | | | | 122-124 |
| 60.44 | N-[(1,2 cis)-2-(4-bromophenyl)cyclobutyl]-3-chloropyrazine-2-carboxamide | | | | 167-169 |
| 60.45 | N-[(1,2 cis)-2-(4-bromophenyl)cyclobutyl]-3-(trifluoromethyl)pyrazine-2-carboxamide | | | | 166-170 |
| 60.46 | N-[(1,2 cis)-2-(2,4-difluorophenyl)cyclobutyl]-2-(trifluoromethyl)benzamide | | | | 106-108 |
| 60.47 | N-[(1,2 cis)-2-(2,4-difluorophenyl)cyclobutyl]-3-(trifluoromethyl)pyridine-2-carboxamide | | | | 124-126 |
| 60.48 | N-[(1,2 cis)-2-(2,4-difluorophenyl)cyclobutyl]-2-(trifluoromethyl)pyridine-3-carboxamide | | | | 146-147 |
| 60.49 | N-[(1,2 cis)-2-(2,4-difluorophenyl)cyclobutyl]-3-(trifluoromethyl)pyrazine-2-carboxamide | | | | 108-110 |
| 60.50 | N-[(1,2 cis)-2-[2-chloro-4-(trifluoromethyl)phenyl]cyclobutyl]-2-(trifluoromethyl)benzamide | | | | 131-133 |
| 60.51 | N-[(1,2 cis)-2-[2-chloro-4-(trifluoromethyl)phenyl]cyclobutyl]-3-(trifluoromethyl)pyridine-2-carboxamide | | | | 95-97 |
| 60.52 | N-[(1,2 cis)-2-[2-chloro-4-(trifluoromethyl)phenyl]cyclobutyl]-2-(trifluoromethyl)pyridine-3-carboxamide | | | | 137-139 |
| 60.53 | N-[(1,2 cis)-2-[2-chloro-4-(trifluoromethyl)phenyl]cyclobutyl]-3-(trifluoromethyl)pyrazine-2-carboxamide | | | | 112-114 |
| 60.54 | N-[(1,2 cis)-2-[2-fluoro-4-(trifluoromethyl)phenyl]cyclobutyl]-2-(trifluoromethyl)benzamide | | | | 110-112 |
| 60.55 | N-[(1,2 cis)-2-[2-fluoro-4-(trifluoromethyl)phenyl]cyclobutyl]-3-(trifluoromethyl)pyridine-2-carboxamide | | | | 109-111 |
| 60.56 | N-[(1,2 cis)-2-[2-fluoro-4-(trifluoromethyl)phenyl]cyclobutyl]-2-(trifluoromethyl)pyridine-3-carboxamide | | | | 151-153 |
| 60.57 | N-[(1,2 cis)-2-[2-fluoro-4-(trifluoromethyl)phenyl]cyclobutyl]-3-(trifluoromethyl)pyrazine-2-carboxamide | | | | 152-154 |
| 60.58 | 2-chloro-N-[(1,2 cis)-2-(2,4-dichlorophenyl)cyclobutyl]benzamide | 1.74 | 354 | A | |
| 60.59 | N-[(1,2 cis)-2-(2,4-dichlorophenyl)cyclobutyl]-2-methylbenzamide | 1.74 | 334 | A | |
| 60.60 | N-[(1,2 cis)-2-(2,4-dichlorophenyl)cyclobutyl]-2,4,6-trifluorobenzamide | 1.73 | 374 | A | |
| 60.61 | N-[(1,2 cis)-2-(2,4-dichlorophenyl)cyclobutyl]-2-methylfuran-3-carboxamide | 1.66 | 324 | A | |
| 60.62 | N-[(1,2 cis)-2-(2,4-dichlorophenyl)cyclobutyl]-2-fluorobenzamide | 1.76 | 338 | A | |
| 60.63 | 2-chloro-N-[(1,2 cis)-2-(2,4-dichlorophenyl)cyclobutyl]-6-fluorobenzamide | 1.74 | 372 | A | |
| 60.64 | N-[(1,2 cis)-2-(2,4-dichlorophenyl)cyclobutyl]-3-methylpyridine-2-carboxamide | 1.79 | 335 | A | |
| 60.65 | 2-cyano-N-[(1,2 cis)-2-(2,4-dichlorophenyl)cyclobutyl]benzamide | 1.58 | 345 | A | |
| 60.66 | N-[(1,2 cis)-2-(2,4-dichlorophenyl)cyclobutyl]-2-fluoro-6-methylbenzamide | 1.74 | 352 | A | |
| 60.67 | N-[(1,2 cis)-2-(2,4-dichlorophenyl)cyclobutyl]-3-methylpyrazine-2-carboxamide | 1.62 | 336 | A | |
| 60.68 | N-[(1,2 cis)-2-(2,4-dichlorophenyl)cyclobutyl]-2-iodobenzamide | 1.79 | 446 | A | |
| 60.69 | N-[(1,2 cis)-2-(2,4-dichlorophenyl)cyclobutyl]-2-(trifluoromethoxy)benzamide | 1.89 | 404 | A | |
| 60.70 | N-[(1,2 cis)-2-(2,4-dichlorophenyl)cyclobutyl]-2-fluoro-6-(trifluoromethyl)benzamide | 1.81 | 406 | A | |

TABLE 60-continued

| Entry | Name | RT (min) | [M + H] (measured) | Method | MP (° C.) |
|---|---|---|---|---|---|
| 60.71 | 2-bromo-N-[(1,2 cis)-2-(2,4-dichlorophenyl)cyclobutyl]benzamide | 1.75 | 397 | A | |
| 60.72 | N-[(1,2 cis)-2-(2,4-dichlorophenyl)cyclobutyl]-2-methylpyridine-3-carboxamide | 1.17 | 335 | A | |
| 60.73 | N-[(1,2 cis)-2-(2,4-dichlorophenyl)cyclobutyl]-2-(trifluoromethylsulfanyl)benzamide | 1.92 | 420 | A | |
| 60.74 | 5-chloro-N-[(1,2 cis)-2-(2,4-dichlorophenyl)cyclobutyl]pyrimidine-4-carboxamide | 1.58 | 356 | A | |
| 60.75 | N-[(1,2 cis)-2-(4-chlorophenyl)cyclobutyl]-2-methylbenzamide | 1.63 | 300 | A | |
| 60.76 | N-[(1,2 cis)-2-(4-chlorophenyl)cyclobutyl]-2,4,6-trifluorobenzamide | 1.62 | 340 | A | |
| 60.77 | N-[(1,2 cis)-2-(4-chlorophenyl)cyclobutyl]-2-methylfuran-3-carboxamide | 1.55 | 290 | A | |
| 60.78 | N-[(1,2 cis)-2-(4-chlorophenyl)cyclobutyl]-2-fluorobenzamide | 1.64 | 304 | A | |
| 60.79 | 2-chloro-N-[(1,2 cis)-2-(4-chlorophenyl)cyclobutyl]-6-fluorobenzamide | 1.63 | 338 | A | |
| 60.80 | N-[(1,2 cis)-2-(4-chlorophenyl)cyclobutyl]-3-methylpyridine-2-carboxamide | 1.65 | 301 | A | |
| 60.81 | N-[(1,2 cis)-2-(4-chlorophenyl)cyclobutyl]-2-cyanobenzamide | 1.45 | 310 | A | |
| 60.82 | N-[(1,2 cis)-2-(4-chlorophenyl)cyclobutyl]-2-fluoro-6-methoxybenzamide | 1.56 | 334 | A | |
| 60.83 | N-[(1,2 cis)-2-(4-chlorophenyl)cyclobutyl]-2-fluoro-6-methylbenzamide | 1.63 | 318 | A | |
| 60.84 | N-[(1,2 cis)-2-(4-chlorophenyl)cyclobutyl]-3-methylpyrazine-2-carboxamide | 1.49 | 301 | A | |
| 60.85 | 2,6-dichloro-N-[(1,2 cis)-2-(4-chlorophenyl)cyclobutyl]benzamide | 1.69 | 354 | A | |
| 60.86 | N-[(1,2 cis)-2-(4-chlorophenyl)cyclobutyl]-2-iodobenzamide | 1.68 | 411 | A | |
| 60.87 | N-[(1,2 cis)-2-(4-chlorophenyl)cyclobutyl]-2-(trifluoromethoxy)benzamide | 1.78 | 370 | A | |
| 60.88 | N-[(1,2 cis)-2-(4-chlorophenyl)cyclobutyl]-2-fluoro-6-(trifluoromethyl)benzamide | 1.71 | 372 | A | |
| 60.89 | 2-bromo-N-[(1,2 cis)-2-(4-chlorophenyl)cyclobutyl]benzamide | 1.64 | 364 | A | |
| 60.90 | N-[(1,2 cis)-2-(4-chlorophenyl)cyclobutyl]-2-methylpyridine-3-carboxamide | 1.03 | 301 | A | |
| 60.91 | N-[(1,2 cis)-2-(4-chlorophenyl)cyclobutyl]-2-(trifluoromethylsulfanyl)benzamide | 1.83 | 386 | A | |
| 60.92 | 5-chloro-N-[(1,2 cis)-2-(4-chlorophenyl)cyclobutyl]pyrimidine-4-carboxamide | 1.45 | 322 | A | |
| 60.93 | 3-chloro-N-[(1,2 cis)-2-(2,4-dichlorophenyl)cyclobutyl]pyridine-2-carboxamide | 1.66 | 355 | A | |
| 60.94 | 2-chloro-N-[(1,2 cis)-2-(4-chlorophenyl)cyclobutyl]benzamide | 1.62 | 320 | A | |
| 60.95 | N-[(1,2 cis)-2-(3-chlorophenyl)cyclobutyl]-2-(trifluoromethyl)benzamide | | | | 129-130 |
| 60.96 | N-[(1,2 cis)-2-(3-chlorophenyl)cyclobutyl]-2-(trifluoromethyl)pyridine-3-carboxamide | | | | 124-125 |
| 60.97 | N-[(1,2 cis)-2-(3-chlorophenyl)cyclobutyl]-3-(trifluoromethyl)pyridine-2-carboxamide | 1.06 | 355 | B | |
| 60.98 | N-[(1,2 cis)-2-(3-chlorophenyl)cyclobutyl]-3-(trifluoromethyl)pyrazine-2-carboxamide | | | | 110-111 |
| 60.99 | 2-chloro-N-[(1,2 cis)-2-(3-chlorophenyl)cyclobutyl]pyridine-3-carboxamide | | | | 131-132 |
| 60.100 | 3-chloro-N-[(1,2 cis)-2-(3-chlorophenyl)cyclobutyl]pyrazine-2-carboxamide | | | | 107-108 |
| 60.101 | N-[(1,2 cis)-2-(3-chlorophenyl)cyclobutyl]-2,6-difluorobenzamide | | | | 97-99 |
| 60.102 | 3-chloro-N-[(1,2 cis)-2-(3-chlorophenyl)cyclobutyl]pyridine-2-carboxamide | 1.01 | 321 | B | |
| 60.103 | N-[(1,2 cis)-2-(4-bromo-2-fluorophenyl)cyclobutyl]-2-(trifluoromethyl)benzamide | | | | 109.2-118.1 |
| 60.104 | N-[(1,2 cis)-2-(4-bromo-2-fluorophenyl)cyclobutyl]-2-(trifluoromethyl)pyridine-3-carboxamide | | | | 133.9-138 |
| 60.105 | N-[(1,2 cis)-2-(4-bromo-2-fluorophenyl)cyclobutyl]-3-(trifluoromethyl)pyrazine-2-carboxamide | | | | 144.3-149.1 |
| 60.106 | N-[(1,2 cis)-2-(4-bromo-2-fluorophenyl)cyclobutyl]-3-chloropyrazine-2-carboxamide | | | | 125.6-132.9 |
| 60.107 | N-[(1,2 cis)-2-(2-bromo-4-fluorophenyl)cyclobutyl]-2-(trifluoromethyl)benzamide | | | | 96.5-105.6 |
| 60.108 | N-[(1,2 cis)-2-(2-bromo-4-fluorophenyl)cyclobutyl]-2-(trifluoromethyl)pyridine-3-carboxamide | | | | 140.2-148.3 |
| 60.109 | N-[(1,2 cis)-2-(2-bromo-4-fluorophenyl)cyclobutyl]-3-chloropyrazine-2-carboxamide | 0.98 | 384 | B | |
| 60.110 | N-[(1,2 cis)-2-(2,5-dichlorophenyl)cyclobutyl]-2-(trifluoromethyl)benzamide | | | | 123-124 |
| 60.111 | N-[(1,2 cis)-2-(2,5-dichlorophenyl)cyclobutyl]-2-(trifluoromethyl)pyridine-3-carboxamide | | | | 177-178 |
| 60.112 | N-[(1,2 cis)-2-(2,5-dichlorophenyl)cyclobutyl]-3-(trifluoromethyl)pyridine-2-carboxamide | 1.11 | 389 | B | |
| 60.113 | N-[(1,2 cis)-2-(3-bromophenyl)cyclobutyl]-2-(trifluoromethyl)benzamide | | | | 121-121 |
| 60.114 | N-[(1,2 cis)-2-(3-bromophenyl)cyclobutyl]-3-(trifluoromethyl)pyridine-2-carboxamide | | | | 75-75 |
| 60.115 | N-[(1,2 cis)-2-(3-bromophenyl)cyclobutyl]-2-(trifluoromethyl)pyridine-3-carboxamide | | | | 129-129 |
| 60.116 | N-[(1,2 cis)-2-(3-bromophenyl)cyclobutyl]-3-(trifluoromethyl)pyrazine-2-carboxamide | | | | 115-115 |
| 60.117 | N-[(1,2 cis)-2-(3-bromophenyl)cyclobutyl]-2-chloropyridine-3-carboxamide | | | | 140-140 |
| 60.118 | N-[(1,2 cis)-2-(3-bromophenyl)cyclobutyl]-3-chloropyrazine-2-carboxamide | | | | 105-105 |
| 60.119 | N-[(1,2 cis)-2-(3-bromophenyl)cyclobutyl]-2,6-difluorobenzamide | | | | 103-103 |
| 60.120 | N-[(1,2 cis)-2-(3-bromophenyl)cyclobutyl]-3-chloropyridine-2-carboxamide | 1.02 | 365 | B | |
| 60.121 | N-[(1,2 cis)-2-(2,5-dichlorophenyl)cyclobutyl]-3-(trifluoromethyl)pyrazine-2-carboxamide | | | | 153-154 |
| 60.122 | 2-chloro-N-[(1,2 cis)-2-(2,5-dichlorophenyl)cyclobutyl]pyridine-3-carboxamide | | | | 130-131 |
| 60.123 | 3-chloro-N-[(1,2 cis)-2-(2,5-dichlorophenyl)cyclobutyl]pyrazine-2-carboxamide | 1.03 | 356 | B | |
| 60.124 | N-[(1,2 cis)-2-(2,5-dichlorophenyl)cyclobutyl]-2,6-difluorobenzamide | | | | 150-151 |
| 60.125 | 3-chloro-N-[(1,2 cis)-2-(2,5-dichlorophenyl)cyclobutyl]pyridine-2-carboxamide | | | | 110-111 |
| 60.126 | N-[(1,2 cis)-2-(2-chlorophenyl)cyclobutyl]-2-(trifluoromethyl)benzamide | 1.06 | 354 | B | |
| 60.127 | N-[(1,2 cis)-2-(2-chlorophenyl)cyclobutyl]-3-(trifluoromethyl)pyridine-2-carboxamide | 1.05 | 355 | B | |
| 60.128 | N-[(1,2 cis)-2-(2-chlorophenyl)cyclobutyl]-2-(trifluoromethyl)pyridine-3-carboxamide | | | | 167-167 |
| 60.129 | N-[(1,2 cis)-2-(2-chlorophenyl)cyclobutyl]-3-(trifluoromethyl)pyrazine-2-carboxamide | | | | 133-133 |
| 60.130 | 2-chloro-N-[(1,2 cis)-2-(2-chlorophenyl)cyclobutyl]pyridine-3-carboxamide | | | | 148-148 |
| 60.131 | 3-chloro-N-[(1,2 cis)-2-(2-chlorophenyl)cyclobutyl]pyrazine-2-carboxamide | | | | 133-133 |
| 60.132 | N-[(1,2 cis)-2-(2-chlorophenyl)cyclobutyl]-2,6-difluorobenzamide | | | | 164-164 |
| 60.133 | 3-chloro-N-[(1,2 cis)-2-(2-chlorophenyl)cyclobutyl]pyridine-2-carboxamide | | | | 82-82 |
| 60.134 | 3-chloro-N-[(1,2 cis)-2-[2-fluoro-4-(trifluoromethyl)phenyl]cyclobutyl]pyrazine-2-carboxamide | | | | 125-127 |
| 60.135 | 2-chloro-N-[(1,2 cis)-2-[2-fluoro-4-(trifluoromethyl)phenyl]cyclobutyl]pyridine-3-carboxamide | | | | 109-111 |
| 60.136 | N-[(1,2 cis)-2-[2-fluoro-4-(trifluoromethyl)phenyl]cyclobutyl]-2-methylpyridine-3-carboxamide | | | | 135-138 |
| 60.137 | N-[(1,2 cis)-2-(2-bromophenyl)cyclobutyl]-3-(trifluoromethyl)pyridine-2-carboxamide | | | | 170-170 |
| 60.138 | N-[(1,2 cis)-2-(2-bromophenyl)cyclobutyl]-2-(trifluoromethyl)benzamide | | | | 169-169 |
| 60.139 | N-[(1,2 cis)-2-(2-bromophenyl)cyclobutyl]-2-(trifluoromethyl)pyridine-3-carboxamide | | | | 172-172 |
| 60.140 | N-[(1,2 cis)-2-(2-bromophenyl)cyclobutyl]-3-(trifluoromethyl)pyrazine-2-carboxamide | | | | 171-171 |
| 60.141 | N-[(1,2 cis)-2-(3,4-dichlorophenyl)cyclobutyl]-2-(trifluoromethyl)benzamide | | | | 167-169 |
| 60.142 | N-[(1,2 cis)-2-(3,4-dichlorophenyl)cyclobutyl]-2-(trifluoromethyl)pyridine-3-carboxamide | | | | 124-126 |
| 60.143 | N-[(1,2 cis)-2-(3,4-dichlorophenyl)cyclobutyl]-3-(trifluoromethyl)pyridine-2-carboxamide | | | | 107-108 |
| 60.144 | N-[(1,2 cis)-2-(3,4-dichlorophenyl)cyclobutyl]-3-(trifluoromethyl)pyrazine-2-carboxamide | | | | 104-105 |
| 60.145 | 2-chloro-N-[(1,2 cis)-2-(3,4-dichlorophenyl)cyclobutyl]pyridine-3-carboxamide | | | | 102-104 |
| 60.146 | 3-chloro-N-[(1,2 cis)-2-(3,4-dichlorophenyl)cyclobutyl]pyrazine-2-carboxamide | | | | 117-118 |
| 60.147 | N-[(1,2 cis)-2-(3,4-dichlorophenyl)cyclobutyl]-2,6-difluorobenzamide | | | | 138-140 |

TABLE 60-continued

| Entry | Name | RT (min) | [M + H] (measured) | Method | MP (° C.) |
|---|---|---|---|---|---|
| 60.148 | 3-chloro-N-[(1,2 cis)-2-(3,4-dichlorophenyl)cyclobutyl]pyridine-2-carboxamide | 1.07 | 355 | B | |
| 60.149 | N-[(1,2 cis)-2-(2,6-dichlorophenyl)cyclobutyl]-2-(trifluoromethyl)benzamide | | | | 122-122 |
| 60.150 | N-[(1,2 cis)-2-(2,6-dichlorophenyl)cyclobutyl]-3-(trifluoromethyl)pyridine-2-carboxamide | | | | 139-139 |
| 60.151 | N-[(1,2 cis)-2-(2,6-dichlorophenyl)cyclobutyl]-2-(trifluoromethyl)pyridine-3-carboxamide | | | | 191-191 |
| 60.152 | N-[(1,2 cis)-2-(2,6-dichlorophenyl)cyclobutyl]-3-(trifluoromethyl)pyrazine-2-carboxamide | | | | 177-177 |
| 60.153 | 2-chloro-N-[(1,2 cis)-2-(2,6-dichlorophenyl)cyclobutyl]pyridine-3-carboxamide | | | | 187-187 |
| 60.154 | 3-chloro-N-[(1,2 cis)-2-(2,6-dichlorophenyl)cyclobutyl]pyrazine-2-carboxamide | | | | 173-173 |
| 60.155 | N-[(1,2 cis)-2-(2,6-dichlorophenyl)cyclobutyl]-2,6-difluorobenzamide | | | | 137-137 |
| 60.156 | 3-chloro-N-[(1,2 cis)-2-(2,6-dichlorophenyl)cyclobutyl]pyridine-2-carboxamide | | | | 116-116 |
| 60.157 | N-[(1,2 cis)-2-(3,5-dichlorophenyl)cyclobutyl]-2-(trifluoromethyl)benzamide | | | | 172-174 |
| 60.158 | N-[(1,2 cis)-2-(3,5-dichlorophenyl)cyclobutyl]-2-(trifluoromethyl)pyridine-3-carboxamide | | | | 156-157 |
| 60.159 | N-[(1,2 cis)-2-(3,5-dichlorophenyl)cyclobutyl]-3-(trifluoromethyl)pyridine-2-carboxamide | 1.14 | 389 | B | |
| 60.160 | 2-chloro-N-[(1,2 cis)-2-(3,5-dichlorophenyl)cyclobutyl]pyridine-3-carboxamide | | | | 136-137 |
| 60.161 | 3-chloro-N-[(1,2 cis)-2-(3,5-dichlorophenyl)cyclobutyl]pyrazine-2-carboxamide | | | | 141-142 |
| 60.162 | N-[(1,2 cis)-2-(3,5-dichlorophenyl)cyclobutyl]-2,6-difluorobenzamide | | | | 120-121 |
| 60.163 | N-[(1,2 cis)-2-(3,5-dichlorophenyl)cyclobutyl]-3-(trifluoromethyl)pyrazine-2-carboxamide | | | | 120-121 |
| 60.164 | 3-chloro-N-[(1,2 cis)-2-(3,5-dichlorophenyl)cyclobutyl]pyridine-2-carboxamide | | | | 129-130 |
| 60.165 | N-[(1,2 cis)-2-(4-propan-2-yloxyphenyl)cyclobutyl]-2-(trifluoromethyl)benzamide | | | | 124-125 |
| 60.166 | 2-chloro-N-[(1,2 cis)-2-(4-propan-2-yloxyphenyl)cyclobutyl]pyridine-3-carboxamide | | | | 121-122 |
| 60.167 | 2,6-difluoro-N-[(1,2 cis)-2-(4-propan-2-yloxyphenyl)cyclobutyl]benzamide | | | | 119-120 |
| 60.168 | N-[(1,2 cis)-2-(4-methylsulfonylphenyl)cyclobutyl]-2-(trifluoromethyl)benzamide | | | | 174-174 |
| 60.169 | N-[(1,2 cis)-2-(4-methylsulfonylphenyl)cyclobutyl]-3-(trifluoromethyl)pyridine-2-carboxamide | | | | 169-169 |
| 60.170 | N-[(1,2 cis)-2-(4-methylsulfonylphenyl)cyclobutyl]-2-(trifluoromethyl)pyridine-3-carboxamide | | | | 197-197 |
| 60.171 | N-[(1,2 cis)-2-(4-methylsulfonylphenyl)cyclobutyl]-3-(trifluoromethyl)pyrazine-2-carboxamide | | | | 178-178 |
| 60.172 | 2-chloro-N-[(1,2 cis)-2-(4-methylsulfonylphenyl)cyclobutyl]pyridine-3-carboxamide | | | | 169-169 |
| 60.173 | 3-chloro-N-[(1,2 cis)-2-(4-methylsulfonylphenyl)cyclobutyl]pyrazine-2-carboxamide | | | | 173-173 |
| 60.174 | 2,6-difluoro-N-[(1,2 cis)-2-(4-methylsulfonylphenyl)cyclobutyl]benzamide | | | | 177-177 |
| 60.175 | 3-chloro-N-[(1,2 cis)-2-(4-methylsulfonylphenyl)cyclobutyl]pyridine-2-carboxamide | | | | 152-152 |
| 60.176 | N-[(1,2 cis)-2-(2,4,6-trichlorophenyl)cyclobutyl]-2-(trifluoromethyl)benzamide | | | | 102-102 |
| 60.177 | N-[(1,2 cis)-2-(2,4,6-trichlorophenyl)cyclobutyl]-3-(trifluoromethyl)pyridine-2-carboxamide | | | | 117-117 |
| 60.178 | N-[(1,2 cis)-2-(2,3-dichlorophenyl)cyclobutyl]-2-(trifluoromethyl)benzamide | | | | 109-110 |
| 60.179 | N-[(1,2 cis)-2-(4-propan-2-yloxyphenyl)cyclobutyl]-2-(trifluoromethyl)pyridine-3-carboxamide | | | | 152-153 |
| 60.180 | N-[(1,2 cis)-2-(2,3-dichlorophenyl)cyclobutyl]-2-(trifluoromethyl)pyridine-3-carboxamide | | | | 149-150 |
| 60.181 | N-[(1,2 cis)-2-(4-propan-2-yloxyphenyl)cyclobutyl]-3-(trifluoromethyl)pyridine-2-carboxamide | | | | 105-106 |
| 60.182 | N-[(1,2 cis)-2-(2,3-dichlorophenyl)cyclobutyl]-3-(trifluoromethyl)pyridine-2-carboxamide | | | | 82-83 |
| 60.183 | N-[(1,2 cis)-2-(4-propan-2-yloxyphenyl)cyclobutyl]-3-(trifluoromethyl)pyrazine-2-carboxamide | | | | 128-129 |
| 60.184 | N-[(1,2 cis)-2-(2,3-dichlorophenyl)cyclobutyl]-3-(trifluoromethyl)pyrazine-2-carboxamide | | | | 113-114 |
| 60.185 | 2-chloro-N-[(1,2 cis)-2-(2,3-dichlorophenyl)cyclobutyl]pyridine-3-carboxamide | | | | 150-151 |
| 60.186 | 3-chloro-N-[(1,2 cis)-2-(4-propan-2-yloxyphenyl)cyclobutyl]pyrazine-2-carboxamide | | | | 108-109 |
| 60.187 | 3-chloro-N-[(1,2 cis)-2-(2,3-dichlorophenyl)cyclobutyl]pyrazine-2-carboxamide | | | | 109-110 |
| 60.188 | N-[(1,2 cis)-2-(2,3-dichlorophenyl)cyclobutyl]-2,6-difluorobenzamide | | | | 162-163 |
| 60.189 | 3-chloro-N-[(1,2 cis)-2-(4-propan-2-yloxyphenyl)cyclobutyl]pyridine-2-carboxamide | | | | 101-102 |
| 60.190 | 3-chloro-N-[(1,2 cis)-2-(2,3-dichlorophenyl)cyclobutyl]pyridine-2-carboxamide | | | | 117-118 |
| 60.191 | N-[(1,2 cis)-2-(4-bromo-2-chlorophenyl)cyclobutyl]-2-(trifluoromethyl)pyridine-3-carboxamide | | | | 146-150 |
| 60.192 | N-[(1,2 cis)-2-(4-bromo-2-chlorophenyl)cyclobutyl]-3-(trifluoromethyl)pyrazine-2-carboxamide | | | | 130-133 |
| 60.193 | N-[(1,2 cis)-2-(4-bromo-2-chlorophenyl)cyclobutyl]-3-chloropyrazine-2-carboxamide | 1.67 | 400 | G | |
| 60.194 | N-[(1,2 cis)-2-(4-bromo-2-chlorophenyl)cyclobutyl]-3-(trifluoromethyl)pyridine-2-carboxamide | 1.86 | 433 | G | |
| 60.195 | N-[(1,2 cis)-2-(4-bromo-2-chlorophenyl)cyclobutyl]-2-(trifluoromethyl)benzamide | 1.88 | 432 | G | |
| 60.196 | N-[(1,2 cis)-2-(2,4-dichloro-6-methoxyphenyl)cyclobutyl]-2-(trifluoromethyl)benzamide | | | | 120-121 |
| 60.197 | N-[(1,2 cis)-2-(2,4-dichloro-6-methoxyphenyl)cyclobutyl]-2-(trifluoromethyl)pyridine-3-carboxamide | | | | 162-164 |
| 60.198 | N-[(1,2 cis)-2-(2,4-dichloro-6-methoxyphenyl)cyclobutyl]-3-(trifluoromethyl)pyridine-2-carboxamide | | | | 177-179 |
| 60.199 | N-[(1,2 cis)-2-(2,4,6-trichlorophenyl)cyclobutyl]-2-(trifluoromethyl)pyridine-3-carboxamide | | | | 161-161 |
| 60.200 | N-[(1,2 cis)-2-(2,4,6-trichlorophenyl)cyclobutyl]-3-(trifluoromethyl)pyrazine-2-carboxamide | | | | 138-138 |
| 60.201 | 2-chloro-N-[(1,2 cis)-2-(2,4,6-trichlorophenyl)cyclobutyl]pyridine-3-carboxamide | | | | 143-143 |
| 60.202 | 3-chloro-N-[(1,2 cis)-2-(2,4,6-trichlorophenyl)cyclobutyl]pyrazine-2-carboxamide | | | | 125-125 |
| 60.203 | 2,6-difluoro-N-[(1,2 cis)-2-(2,4,6-trichlorophenyl)cyclobutyl]benzamide | | | | 113-113 |
| 60.204 | 3-chloro-N-[(1,2 cis)-2-(2,4,6-trichlorophenyl)cyclobutyl]pyridine-2-carboxamide | | | | 133-133 |
| 60.205 | 2-(trifluoromethyl)-N-[(1,2 cis)-2-[4-[3-(trifluoromethyl)pyrazol-1-yl]phenyl]cyclobutyl]benzamide | 1.11 | 454 | B | |
| 60.206 | N-[(1,2 cis)-2-(2,4-dichloro-6-methoxyphenyl)cyclobutyl]-3-(trifluoromethyl)pyrazine-2-carboxamide | | | | 147-148 |
| 60.207 | 2-chloro-N-[(1,2 cis)-2-(2,4-dichloro-6-methoxyphenyl)cyclobutyl]pyridine-3-carboxamide | | | | 135-136 |
| 60.208 | 3-chloro-N-[(1,2 cis)-2-(2,4-dichloro-6-methoxyphenyl)cyclobutyl]pyrazine-2-carboxamide | | | | 130-132 |
| 60.209 | N-[(1,2 cis)-2-(2,4-dichloro-6-methoxyphenyl)cyclobutyl]-2,6-difluorobenzamide | | | | 132-135 |
| 60.210 | 3-chloro-N-[(1,2 cis)-2-(2,4-dichloro-6-methoxyphenyl)cyclobutyl]pyridine-2-carboxamide | | | | 165-167 |
| 60.211 | 2-(trifluoromethyl)-N-[(1,2 cis)-2-[4-[3-(trifluoromethyl)pyrazol-1-yl]phenyl]cyclobutyl]pyridine-3-carboxamide | | | | 191-192 |
| 60.212 | 2-chloro-N-[(1,2 cis)-2-[4-[3-(trifluoromethyl)pyrazol-1-yl]phenyl]cyclobutyl]pyridine-3-carboxamide | | | | 146-147 |
| 60.213 | 3-(trifluoromethyl)-N-[(1,2 cis)-2-[4-[3-(trifluoromethyl)pyrazol-1-yl]phenyl]cyclobutyl]pyridine-2-carboxamide | | | | 132-133 |
| 60.214 | 3-chloro-N-[(1,2 cis)-2-(2,4-difluorophenyl)cyclobutyl]pyrazine-2-carboxamide | | | | 98-99.5 |
| 60.215 | N-[(1,2 cis)-2-(2,4-dichloro-6-propan-2-yloxyphenyl)cyclobutyl]-2-(trifluoromethyl)benzamide | | | | 124-125 |
| 60.216 | N-[(1,2 cis)-2-(2,4-dichloro-6-propan-2-yloxyphenyl)cyclobutyl]-2-(trifluoromethyl)pyridine-3-carboxamide | | | | 113-115 |

TABLE 60-continued

| Entry | Name | RT (min) | [M + H] (measured) | Method | MP (° C.) |
|---|---|---|---|---|---|
| 60.217 | N-[(1,2 cis)-2-(2,4-dichloro-6-propan-2-yloxyphenyl)cyclobutyl]-3-(trifluoromethyl)pyridine-2-carboxamide | | | | 170-172 |
| 60.218 | N-[(1,2 cis)-2-(2,4-dichloro-6-propan-2-yloxyphenyl)cyclobutyl]-3-(trifluoromethyl)pyrazine-2-carboxamide | | | | 156-158 |
| 60.219 | N-[(1,2 cis)-2-(2-fluorophenyl)cyclobutyl]-2-(trifluoromethyl)benzamide | | | | 136-138 |
| 60.220 | 2-chloro-N-[(1,2 cis)-2-(2,4-dichloro-6-propan-2-yloxyphenyl)cyclobutyl]pyridine-3-carboxamide | 1.17 | 413 | B | |
| 60.221 | 3-chloro-N-[(1,2 cis)-2-(2,4-dichloro-6-propan-2-yloxyphenyl)cyclobutyl]pyrazine-2-carboxamide | | | | 122-123 |
| 60.222 | 3-chloro-N-[(1,2 cis)-2-(2,4-difluorophenyl)cyclobutyl]pyridazine-4-carboxamide | | | | 135-136 |
| 60.223 | 3-chloro-N-[(1,2 cis)-2-(2-fluorophenyl)cyclobutyl]pyridazine-4-carboxamide | | | | 125-126 |
| 60.224 | 4-chloro-N-[(1,2 cis)-2-(2,4-difluorophenyl)cyclobutyl]-2-(trifluoromethyl)pyridine-3-carboxamide | | | | 157-158 |
| 60.225 | N-[(1,2 cis)-2-(2-fluorophenyl)cyclobutyl]-2-(trifluoromethyl)pyridine-3-carboxamide | | | | 123-124 |
| 60.226 | 2-chloro-N-[(1,2 cis)-2-(2-fluorophenyl)cyclobutyl]pyridine-3-carboxamide | | | | 155-156 |
| 60.227 | N-[(1,2 cis)-2-(2-fluorophenyl)cyclobutyl]-3-(trifluoromethyl)pyrazine-2-carboxamide | | | | 124-125 |
| 60.228 | N-[(1,2 cis)-2-(2-fluorophenyl)cyclobutyl]-3-(trifluoromethyl)pyridine-2-carboxamide | | | | 133-134 |
| 60.229 | N-[(1,2 cis)-2-(2,4-difluorophenyl)cyclobutyl]-4-(trifluoromethyl)pyridazine-3-carboxamide | | | | 123-126 |
| 60.230 | N-[(1,2 cis)-2-(2,4-difluorophenyl)cyclobutyl]-3-(trifluoromethyl)pyridazine-4-carboxamide | | | | 152-155 |
| 60.231 | N-[(1,2 cis)-2-(2-fluorophenyl)cyclobutyl]-3-(trifluoromethyl)pyridazine-4-carboxamide | | | | 133-136 |
| 60.232 | 4-chloro-N-[(1,2 cis)-2-(2,4-difluorophenyl)cyclobutyl]-3-(trifluoromethyl)pyridine-2-carboxamide | | | | 101-103 |
| 60.233 | N-[(2,3 cis)-2-phenyloxetan-3-yl]-2-(trifluoromethyl)benzamide | | | | 158-167 |
| 60.234 | N-[(2,3 cis)-2-(4-chlorophenyl)oxetan-3-yl]-2-(trifluoromethyl)benzamide | | | | |
| 60.235 | N-[(2,3 cis)-2-(4-fluorophenyl)oxetan-3-yl]-2-(trifluoromethyl)benzamide | 0.88 | 340 | A | |
| 60.236 | 2-(trifluoromethyl)-N-[(2,3 cis)-2-(2,4,6-trifluorophenyl)oxetan-3-yl]benzamide | 0.89 | 376 | A | |
| 60.237 | N-[(2,3 cis)-2-[4-(difluoromethoxy)phenyl]oxetan-3-yl]-2-(trifluoromethyl)benzamide | | | | 115-120 |
| 60.238 | 2-(trifluoromethyl)-N-[(2,3 cis)-2[4-(trifluoromethyl)phenyl]oxetan-3-yl]benzamide | | | | 123-125 |
| 60.239 | N-[(2,3 cis)-2-[2-fluoro-4-(trifluoromethyl)phenyl]oxetan-3-yl]-2-(trifluoromethyl)benzamide | | | | 99-108 |
| 60.240 | N-[(2,3 cis)-2-(2,4-difluorophenyl)oxetan-3-yl]-2,6-difluorobenzamide | | | | 125-130 |
| 60.241 | 2,6-difluoro-N-[(2,3 cis)-2-(2,4,6-trifluorophenyl)oxetan-3-yl]benzamide | | | | 130-136 |
| 60.242 | 2,6-difluoro-N-[(2,3 cis)-2-(4-fluorophenyl)oxetan-3-yl]benzamide | | | | 95-101 |
| 60.243 | N-[(2,3 cis)-2-(4-fluorophenyl)oxetan-3-yl]-2-(trifluoromethyl)pyridine-3-carboxamide | | | | 107-127 |
| 60.244 | N-[(2,3 cis)-2-(2,4-difluorophenyl)oxetan-3-yl]-2-(trifluoromethyl)benzamide | | | | 129-132 |
| 60.245 | N-[(2,3 cis)-2-(2,4-difluorophenyl)oxetan-3-yl]-2-(trifluoromethyl)pyridine-3-carboxamide | | | | 131-134 |
| 60.246 | 2-(trifluoromethyl)-N-[(2,3 cis)-2-(2,4,6-trifluorophenyl)oxetan-3-yl]pyridine-3-carboxamide | | | | 143-146 |
| 60.247 | N-[(1,2 cis)-2-(2,3-difluorophenyl)cyclobutyl]-2-(trifluoromethyl)benzamide | 1.01 | 356 | | |
| 60.248 | N-[(1,2 cis)-2-(3,4-difluorophenyl)cyclobutyl]-2-(trifluoromethyl)benzamide | 1.03 | 356 | | |

TABLE 61

| Entry | Name | RT (min) | [M + H] (measured) | Method | RT' (min) | Chiral Method | MP (° C.) |
|---|---|---|---|---|---|---|---|
| 61.1 | N-[(1S,2S)-2-(2,4-dichlorophenyl)cyclobutyl]-2-(trifluoromethyl)pyridine-3-carboxamide | | | | 4.81 | C | 12-124 |
| 61.2 | N-[(1S,2S)-2-(2,4-dichlorophenyl)cyclobutyl]-3-(trifluoromethyl)pyrazine-2-carboxamide | | | | | | 91-93 |
| 61.3 | 3-chloro-N-[(1S,2S)-2-(2,4-dichlorophenyl)cyclobutyl]pyrazine-2-carboxamide | 1.03 | 356 | B | 6.46 | D | |
| 61.4 | N-[(1S,2S)-2-(2,4-dichlorophenyl)cyclobutyl]-3-(trifluoromethyl)pyridine-2-carboxamide | 1.11 | 389 | B | 7.27 | K | |
| 61.5 | 3-chloro-N-[(1S,2S)-2-(2,4-dichlorophenyl)cyclobutyl]pyridine-2-carboxamide | | | | | | 85-87 |
| 61.6 | 2-chloro-N-[(1S,2S)-2-(4-chlorophenyl)cyclobutyl]benzamide | | | | | | 115-117 |
| 61.7 | N-[(1S,2S)-2-(2,4-dichlorophenyl)cyclobutyl]-2-methylpyridine-3-carboxamide | 0.86 | 335 | B | | | |
| 61.8 | 2-bromo-N-[(1S,2S)-2-(2,4-dichlorophenyl)cyclobutyl]benzamide | 1.11 | 398 | B | | | |
| 61.9 | N-[(1S,2S)-2-(2,4-dichlorophenyl)cyclobutyl]-2-iodobenzamide | | | | | | 119-121 |
| 61.10 | N-[(1S,2S)-2-(2,4-difluorophenyl)cyclobutyl]-2-(trifluoromethyl)pyridine-3-carboxamide | | | | 5.48 | C | 108-110 |
| 61.11 | N-[(1S,2S)-2-(4-chlorophenyl)cyclobutyl]-3-methoxypyridine-2-carboxamide | 1.32 | 317.06 | R | | | |
| 61.12 | N-[(1S,2S)-2-(4-chlorophenyl)cyclobutyl]-5-cyclopropyl-1,2-oxazole-4-carboxamide | 1.89 | 317.07 | R | | | |
| 61.13 | N-[(1S,2S)-2-(4-chlorophenyl)cyclobutyl]-2-methoxybenzamide | 1.67 | 316.07 | R | | | |
| 61.14 | 3-bromo-N-[(1S,2S)-2-(4-chlorophenyl)cyclobutyl]thiophene-2-carboxamide | 1.77 | 369.92 | R | | | |
| 61.15 | 3-bromo-N-[(1S,2S)-2-(4-chlorophenyl)cyclobutyl]pyridine-2-carboxamide | 1.54 | 364.94 | R | | | 132-134 |
| 61.16 | N-[(1S,2S)-2-(4-chlorophenyl)cyclobutyl]-2-(trifluoromethylsulfanyl)benzamide | 1.80 | 386.02 | R | | | |
| 61.17 | N-[(1S,2S)-2-(4-chlorophenyl)cyclobutyl]-2-methylbenzamide | 1.60 | 300.06 | R | | | |
| 61.18 | N-[(1S,2S)-2-(4-chlorophenyl)cyclobutyl]-4-cyclopropylthiadiazole-5-carboxamide | 1.62 | 334.02 | R | | | |
| 61.19 | N-[(1S,2S)-2-(4-chlorophenyl)cyclobutyl]-2-methylfuran-3-carboxamide | 1.52 | 290.05 | R | | | |
| 61.20 | N-[(1S,2S)-2-(4-chlorophenyl)cyclobutyl]-2-fluorobenzamide | 1.62 | 304.04 | R | | | |
| 61.21 | 2-bromo-N-[(1S,2S)-2-(4-chlorophenyl)cyclobutyl]benzamide | 1.61 | 363.96 | R | | | 127-132 |
| 61.22 | 2-chloro-N-[(1S,2S)-2-(4-chlorophenyl)cyclobutyl]-6-fluorobenzamide | 1.61 | 338.02 | R | | | |
| 61.23 | N-[(1S,2S)-2-(4-chlorophenyl)cyclobutyl]-2-methylpyridine-3-carboxamide | 1.02 | 301.06 | R | | | |
| 61.24 | N-[(1S,2S)-2-(4-chlorophenyl)cyclobutyl]-2-fluoro-6-methoxybenzamide | 1.54 | 334.07 | R | | | |

TABLE 61-continued

| Entry | Name | RT (min) | [M + H] (measured) | Method | RT' (min) | Chiral Method | MP (° C.) |
|---|---|---|---|---|---|---|---|
| 61.25 | N-[(1S,2S)-2-(4-chlorophenyl)cyclobutyl]-2-fluoro-6-methylbenzamide | 1.61 | 318.05 | R | | | |
| 61.26 | N-[(1S,2S)-2-(4-chlorophenyl)cyclobutyl]-3-methylpyrazine-2-carboxamide | 1.47 | 302.06 | R | | | 123-128 |
| 61.27 | 2,6-dichloro-N-[(1S,2S)-2-(4-chlorophenyl)cyclobutyl]benzamide | 1.67 | 353.98 | R | | | |
| 61.28 | N-[(1S,2S)-2-(4-chlorophenyl)cyclobutyl]-1H-pyrrole-2-carboxamide | 1.39 | 275.07 | R | | | |
| 61.29 | N-[(1S,2S)-2-(4-chlorophenyl)cyclobutyl]-4-methyl-1,3-oxazole-5-carboxamide | 1.33 | 291.02 | R | | | |
| 61.30 | N-[(1S,2S)-2-(4-chlorophenyl)cyclobutyl]-3-methyl-1,2-thiazole-4-carboxamide | 1.40 | 307.04 | R | | | |
| 61.31 | 6-chloro-N-[(1S,2S)-2-(4-chlorophenyl)cyclobutyl]-1-oxidopyridin-1-ium-2-carboxamide | 1.49 | 337.02 | R | | | |
| 61.32 | N-[(1S,2S)-2-(4-chlorophenyl)cyclobutyl]-2-iodobenzamide | 1.66 | 411.94 | R | | | |
| 61.33 | N-[(1S,2S)-2-(4-chlorophenyl)cyclobutyl]-1-methylpyrrole-2-carboxamide | 1.54 | 289.06 | R | | | |
| 61.34 | N-[(1S,2S)-2-(4-chlorophenyl)cyclobutyl]-3-(difluoromethyl)-1-methylpyrazole-4-carboxamide | 1.41 | 340.07 | R | | | |
| 61.35 | N-[(1S,2S)-2-(4-chlorophenyl)cyclobutyl]-4-methylthiadiazole-5-carboxamide | 1.44 | 308.03 | R | | | |
| 61.36 | 3-chloro-N-[(1S,2S)-2-(4-chlorophenyl)cyclobutyl]thiophene-2-carboxamide | 1.75 | 325.96 | R | | | |
| 61.37 | N-[(1S,2S)-2-(4-chlorophenyl)cyclobutyl]thiadiazole-4-carboxamide | 1.44 | 293.99 | R | | | |
| 61.38 | N-[(1S,2S)-2-(4-chlorophenyl)cyclobutyl]-2-(trifluoromethoxy)benzamide | 1.76 | 370.03 | R | | | |
| 61.39 | N-[(1S,2S)-2-(4-chlorophenyl)cyclobutyl]-4-methoxythiophene-3-carboxamide | 1.64 | 322.02 | R | | | |
| 61.40 | N-[(1S,2S)-2-(4-chlorophenyl)cyclobutyl]-5-methyl-1,2-oxazole-4-carboxamide | 1.66 | 291.02 | R | | | |
| 61.41 | N-[(1S,2S)-2-(4-chlorophenyl)cyclobutyl]-2-fluoro-6-(trifluoromethyl)benzamide | 1.69 | 372.04 | R | | | 114-125 |
| 61.42 | N-[(1S,2S)-2-(4-chlorophenyl)cyclobutyl]-6-(trifluoromethyl)-2,3-dihydro-1,4-oxathiine-5-carboxamide | 1.60 | 378 | R | | | |
| 61.43 | N-[(1S,2S)-2-(4-chlorophenyl)cyclobutyl]-6-methyl-2,3-dihydro-1,4-oxathiine-5-carboxamide | 1.56 | 324.04 | R | | | |
| 61.44 | 2-bromo-N-[(1S,2S)-2-(4-chlorophenyl)cyclobutyl]thiophene-3-carboxamide | 1.68 | 369.94 | R | | | |
| 61.45 | N-[(1S,2S)-2-(4-chlorophenyl)cyclobutyl]-1,3-thiazole-4-carboxamide | 1.43 | 293 | R | | | |
| 61.46 | 3-chloro-N-[(1S,2S)-2-(4-chlorophenyl)cyclobutyl]pyridine-2-carboxamide | 1.52 | 321.01 | R | | | |
| 61.47 | N-[(1S,2S)-2-(4-chlorophenyl)cyclobutyl]pyrimidine-2-carboxamide | 1.27 | 288.05 | R | | | |
| 61.48 | N-[(1S,2S)-2-(4-chlorophenyl)cyclobutyl]-2-cyanobenzamide | 1.43 | 311.06 | R | | | |
| 61.49 | N-[(1S,2S)-2-(4-chlorophenyl)cyclobutyl]-3-methylpyridine-2-carboxamide | 1.63 | 301.06 | R | | | |
| 61.50 | N-[(1S,2S)-2-(4-chlorophenyl)cyclobutyl]-2-methyl-4-(trifluoromethyl)-1,3-thiazole-5-carboxamide | 1.61 | 375.01 | R | | | |
| 61.51 | 5-chloro-N-[(1S,2S)-2-(4-chlorophenyl)cyclobutyl]thiophene-2-carboxamide | 1.71 | 325.97 | R | | | |
| 61.52 | 2-chloro-N-[(1S,2S)-2-(4-chlorophenyl)cyclobutyl]thiophene-3-carboxamide | 1.68 | 325.96 | R | | | |
| 61.53 | N-[(1S,2S)-2-(4-chlorophenyl)cyclobutyl]-2-iodothiophene-3-carboxamide | 1.67 | 417.88 | R | | | 130-132 |
| 61.54 | N-[(1S,2S)-2-(4-chlorophenyl)cyclobutyl]-2-(trifluoromethyl)thiophene-3-carboxamide | 1.68 | 360 | R | | | |
| 61.55 | 5-bromo-N-[(1S,2S)-2-(4-chlorophenyl)cyclobutyl]-1,3-thiazole-4-carboxamide | 1.60 | 370.92 | R | | | |
| 61.56 | N-[(1S,2S)-2-(2,4-dichlorophenyl)cyclobutyl]-3-methoxypyridine-2-carboxamide | 1.43 | 351.01 | R | | | |
| 61.57 | 5-cyclopropyl-N-[(1S,2S)-2-(2,4-dichlorophenyl)cyclobutyl]-1,2-oxazole-4-carboxamide | 1.42 | 351.04 | R | | | |
| 61.58 | N-[(1S,2S)-2-(2,4-dichlorophenyl)cyclobutyl]-2-methoxybenzamide | 1.76 | 350.03 | R | | | |
| 61.59 | 3-bromo-N-[(1S,2S)-2-(2,4-dichlorophenyl)cyclobutyl]thiophene-2-carboxamide | 1.87 | 403.89 | R | | | |
| 61.60 | 3-bromo-N-[(1S,2S)-2-(2,4-dichlorophenyl)cyclobutyl]pyridine-2-carboxamide | 1.66 | 398.9 | R | | | |
| 61.61 | N-[(1S,2S)-2-(2,4-dichlorophenyl)cyclobutyl]-2-(trifluoromethylsulfanyl)benzamide | 1.89 | 419.96 | R | | | |
| 61.62 | N-[(1S,2S)-2-(2,4-dichlorophenyl)cyclobutyl]-2-methylbenzamide | 1.71 | 334.03 | R | | | |
| 61.63 | 4-cyclopropyl-N-[(1S,2S)-2-(2,4-dichlorophenyl)cyclobutyl]thiadiazole-5-carboxamide | 1.74 | 368.02 | R | | | |
| 61.64 | N-[(1S,2S)-2-(2,4-dichlorophenyl)cyclobutyl]-2-methylfuran-3-carboxamide | 1.63 | 324.01 | R | | | 120-120 |
| 61.65 | N-[(1S,2S)-2-(2,4-dichlorophenyl)cyclobutyl]-2-fluorobenzamide | 1.73 | 338.02 | R | | | |
| 61.66 | 2-chloro-N-[(1S,2S)-2-(2,4-dichlorophenyl)cyclobutyl]-6-fluorobenzamide | 1.71 | 371.98 | R | | | 84-85 |
| 61.67 | N-[(1S,2S)-2-(2,4-dichlorophenyl)cyclobutyl]thiophene-2-carboxamide | 1.61 | 325.96 | R | | | |
| 61.68 | N-[(1S,2S)-2-(2,4-dichlorophenyl)cyclobutyl]-2-fluoro-6-methoxybenzamide | 1.64 | 368.03 | R | | | |
| 61.69 | N-[(1S,2S)-2-(2,4-dichlorophenyl)cyclobutyl]-2-fluoro-6-methylbenzamide | 1.72 | 352.02 | R | | | |
| 61.70 | N-[(1S,2S)-2-(2,4-dichlorophenyl)cyclobutyl]-3-methylpyrazine-2-carboxamide | 1.60 | 336.03 | R | | | |
| 61.71 | 2,6-dichloro-N-[(1S,2S)-2-(2,4-dichlorophenyl)cyclobutyl]benzamide | 1.76 | 387.94 | R | | | |
| 61.72 | N-[(1S,2S)-2-(2,4-dichlorophenyl)cyclobutyl]-1H-pyrrole-2-carboxamide | 1.50 | 309.01 | R | | | |
| 61.73 | N-[(1S,2S)-2-(2,4-dichlorophenyl)cyclobutyl]-4-methyl-1,3-oxazole-5-carboxamide | 1.47 | 325.03 | R | | | |
| 61.74 | N-[(1S,2S)-2-(2,4-dichlorophenyl)cyclobutyl]-3-methyl-1,2-thiazole-4-carboxamide | 1.52 | 340.99 | R | | | 98-99 |
| 61.75 | 6-chloro-N-[(1S,2S)-2-(2,4-dichlorophenyl)cyclobutyl]-1-oxidopyridin-1-ium-2-carboxamide | 1.63 | 370.99 | R | | | |
| 61.76 | N-[(1S,2S)-2-(2,4-dichlorophenyl)cyclobutyl]-1-methylpyrrole-2-carboxamide | 1.65 | 323.03 | R | | | |
| 61.77 | N-[(1S,2S)-2-(2,4-dichlorophenyl)cyclobutyl]-3-(difluoromethyl)-1-methylpyrazole-4-carboxamide | 1.54 | 374.02 | R | | | |
| 61.78 | N-[(1S,2S)-2-(2,4-dichlorophenyl)cyclobutyl]-4-methylthiadiazole-5-carboxamide | 1.57 | 341.98 | R | | | |
| 61.79 | 3-chloro-N-[(1S,2S)-2-(2,4-dichlorophenyl)cyclobutyl]thiophene-2-carboxamide | 1.86 | 359.92 | R | | | |
| 61.80 | N-[(1S,2S)-2-(2,4-dichlorophenyl)cyclobutyl]thiadiazole-4-carboxamide | 1.57 | 327.98 | R | | | |
| 61.81 | N-[(1S,2S)-2-(2,4-dichlorophenyl)cyclobutyl]-2-(trifluoromethoxy)benzamide | 1.86 | 403.98 | R | | | |
| 61.82 | N-[(1S,2S)-2-(2,4-dichlorophenyl)cyclobutyl]-4-methoxythiophene-3-carboxamide | 1.73 | 355.99 | R | | | |
| 61.83 | N-[(1S,2S)-2-(2,4-dichlorophenyl)cyclobutyl]-5-methyl-1,2-oxazole-4-carboxamide | 1.52 | 325.02 | R | | | |
| 61.84 | N-[(1S,2S)-2-(2,4-dichlorophenyl)cyclobutyl]-2-fluoro-6-(trifluoromethyl)benzamide | 1.78 | 406.01 | R | | | |

TABLE 61-continued

| Entry | Name | RT (min) | [M + H] (measured) | Method | RT' (min) | Chiral Method | MP (° C.) |
|---|---|---|---|---|---|---|---|
| 61.85 | N-[(1S,2S)-2-(2,4-dichlorophenyl)cyclobutyl]-6-(trifluoromethyl)-2,3-dihydro-1,4-oxathiine-5-carboxamide | 1.70 | 411.97 | R | | | |
| 61.86 | N-[(1S,2S)-2-(2,4-dichlorophenyl)cyclobutyl]-6-methyl-2,3-dihydro-1,4-oxathiine-5-carboxamide | 1.67 | 358 | R | | | 79-84 |
| 61.87 | 2-bromo-N-[(1S,2S)-2-(2,4-dichlorophenyl)cyclobutyl]thiophene-3-carboxamide | 1.79 | 403.89 | R | | | |
| 61.88 | N-[(1S,2S)-2-(2,4-dichlorophenyl)cyclobutyl]-1,3-thiazole-4-carboxamide | 1.55 | 326.97 | R | | | |
| 61.89 | 2-chloro-N-[(1S,2S)-2-(2,4-dichlorophenyl)cyclobutyl]benzamide | 1.71 | 353.98 | R | | | |
| 61.90 | N-[(1S,2S)-2-(2,4-dichlorophenyl)cyclobutyl]pyrimidine-2-carboxamide | 1.39 | 322 | R | | | |
| 61.91 | 2-cyano-N-[(1S,2S)-2-(2,4-dichlorophenyl)cyclobutyl]benzamide | 1.55 | 345.01 | R | | | |
| 61.92 | N-[(1S,2S)-2-(2,4-dichlorophenyl)cyclobutyl]-3-methylpyridine-2-carboxamide | 1.76 | 335.02 | R | | | |
| 61.93 | N-[(1S,2S)-2-(2,4-dichlorophenyl)cyclobutyl]-2-methyl-4-(trifluoromethyl)-1,3-thiazole-5-carboxamide | 1.72 | 408.97 | R | | | |
| 61.94 | 5-chloro-N-[(1S,2S)-2-(2,4-dichlorophenyl)cyclobutyl]thiophene-2-carboxamide | 1.81 | 359.97 | R | | | |
| 61.95 | 2-chloro-N-[(1S,2S)-2-(2,4-dichlorophenyl)cyclobutyl]thiophene-3-carboxamide | 1.79 | 359.93 | R | | | |
| 61.96 | N-[(1S,2S)-2-(2,4-dichlorophenyl)cyclobutyl]-2-iodothiophene-3-carboxamide | 1.77 | 451.84 | R | | | |
| 61.97 | N-[(1S,2S)-2-(2,4-dichlorophenyl)cyclobutyl]-2-(trifluoromethyl)thiophene-3-carboxamide | 1.78 | 393.94 | R | | | |
| 61.98 | 5-bromo-N-[(1S,2S)-2-(2,4-dichlorophenyl)cyclobutyl]-1,3-thiazole-4-carboxamide | 1.73 | 404.88 | R | | | |
| 61.99 | N-[(1S,2S)-2-(2,4-difluorophenyl)cyclobutyl]-3-(trifluoromethyl)pyrazine-2-carboxamide | | | | 6.29 | J | 128-129 |
| 61.100 | N-[(1S,2S)-2-[2-chloro-4-(trifluoromethyl)phenyl]cyclobutyl]-3-(trifluoromethyl)pyridine-2-carboxamide | | | | 5.46 | I | 74-75 |
| 61.101 | N-[(1S,2S)-2-[2-chloro-4-(trifluoromethyl)phenyl]cyclobutyl]-2-(trifluoromethyl)pyridine-3-carboxamide | | | | 4.66 | H | |
| 61.102 | N-[(1S,2S)-2-[2-fluoro-4-(trifluoromethyl)phenyl]cyclobutyl]-2-(trifluoromethyl)pyridine-3-carboxamide | | | | 5.45 | L | 120-121 |
| 61.103 | N-[(1S,2S)-2-(2,4-dichlorophenyl)cyclobutyl]-2,6-difluorobenzamide | | | | 3.00 | M | 102-104 |
| 61.104 | N-[(1S,2S)-2-(2,4-dichlorophenyl)cyclobutyl]-2-(trifluoromethyl)benzamide | | | | 2.89 | N | 89-91 |
| 61.105 | N-[(1S,2S)-2-(4-chlorophenyl)cyclobutyl]-4-methylfuran-3-carboxamide | | | | | | 65-67 |
| 61.106 | N-[(1S,2S)-2-(2,4-dichlorophenyl)cyclobutyl]-4-methylfuran-3-carboxamide | | | | | | 93-94 |
| 61.107 | N-[(1S,2S)-2-(2,4-dichlorophenyl)cyclobutyl]-2,4-dimethylfuran-3-carboxamide | | | | | | 94-96 |
| 61.108 | N-[(1S,2S)-2-(2,4-difluorophenyl)cyclobutyl]-3-methylpyridine-2-carboxamide | 1.58 | 303.02 | A | | | |
| 61.109 | N-[(1S,2S)-2-(2,4-difluorophenyl)cyclobutyl]-2-methylbenzamide | 1.55 | 302.02 | A | | | |
| 61.110 | N-[(1S,2S)-2-(2,4-difluorophenyl)cyclobutyl]pyrimidine-2-carboxamide | 1.23 | 289.98 | A | | | |
| 61.111 | N-[(1S,2S)-2-(4-chlorophenyl)cyclobutyl]-2-(trifluoromethyl)furan-3-carboxamide | | | | | | 128-130 |
| 61.112 | 5-chloro-N-[(1S,2S)-2-(2,4-difluorophenyl)cyclobutyl]pyrimidine-4-carboxamide | 1.38 | 323.99 | A | | | |
| 61.113 | 2-chloro-N-[(1S,2S)-2-(2,4-difluorophenyl)cyclobutyl]benzamide | 1.55 | 321.99 | A | | | |
| 61.114 | N-[(1S,2S)-2-(2,4-difluorophenyl)cyclobutyl]-4-(trifluoromethyl)pyridine-3-carboxamide | 1.43 | 357.15 | A | | | |
| 61.115 | N-[(1S,2S)-2-(2,4-difluorophenyl)cyclobutyl]thiophene-2-carboxamide | 1.43 | 293.95 | A | | | |
| 61.116 | 2-bromo-N-[(1S,2S)-2-(2,4-difluorophenyl)cyclobutyl]benzamide | 1.57 | 365.94 | A | | | |
| 61.117 | 2-chloro-N-[(1S,2S)-2-(2,4-difluorophenyl)cyclobutyl]-6-fluorobenzamide | 1.55 | 339.99 | A | | | |
| 61.118 | N-[(1S,2S)-2-(2,4-difluorophenyl)cyclobutyl]-2-fluoro-6-methylbenzamide | 1.57 | 320.03 | A | | | |
| 61.119 | N-[(1S,2S)-2-(2,4-difluorophenyl)cyclobutyl]-3-methylpyrazine-2-carboxamide | 1.41 | 304.02 | A | | | |
| 61.120 | N-[(1S,2S)-2-(2,4-difluorophenyl)cyclobutyl]pyridazine-3-carboxamide | 1.28 | 290 | A | | | |
| 61.121 | N-[(1S,2S)-2-(2,4-difluorophenyl)cyclobutyl]-2-fluorobenzamide | 1.57 | 306 | A | | | |
| 61.122 | N-[(1S,2S)-2-(2,4-difluorophenyl)cyclobutyl]-4-(trifluoromethyl)pyrimidine-5-carboxamide | 1.46 | 358.01 | A | | | |
| 61.123 | N-[(1S,2S)-2-(2,4-difluorophenyl)cyclobutyl]-4-methyl-1,3-oxazole-5-carboxamide | 1.29 | 293.03 | A | | | |
| 61.124 | N-[(1S,2S)-2-(2,4-difluorophenyl)cyclobutyl]-3-fluoropyridine-2-carboxamide | 1.43 | 307.08 | A | | | |
| 61.125 | N-[(1S,2S)-2-(2,4-difluorophenyl)cyclobutyl]-2-iodobenzamide | 1.60 | 413.94 | A | | | |
| 61.126 | N-[(1S,2S)-2-(2,4-difluorophenyl)cyclobutyl]-1-methylpyrrole-2-carboxamide | 1.49 | 291.02 | A | | | |
| 61.127 | 3-(difluoromethyl)-N-[(1S,2S)-2-(2,4-difluorophenyl)cyclobutyl]-1-methylpyrazole-4-carboxamide | 1.38 | 342.05 | A | | | |
| 61.128 | 2-acetyl-N-[(1S,2S)-2-(2,4-difluorophenyl)cyclobutyl]pyridine-3-carboxamide | 1.33 | 331.05 | A | | | |
| 61.129 | 3-chloro-N-[(1S,2S)-2-(2,4-difluorophenyl)cyclobutyl]thiophene-2-carboxamide | 1.69 | 327.96 | A | | | |
| 61.130 | N-[(1S,2S)-2-(2,4-difluorophenyl)cyclobutyl]-5-methyl-1,2-oxazole-4-carboxamide | 1.62 | 293.03 | A | | | |
| 61.131 | N-[(1S,2S)-2-(2,4-difluorophenyl)cyclobutyl]-2-fluoro-6-(trifluoromethyl)benzamide | 1.64 | 374 | A | | | 100-101 |
| 61.132 | N-[(1S,2S)-2-(2,4-difluorophenyl)cyclobutyl]-6-methyl-2,3-dihydro-1,4-oxathiine-5-carboxamide | 1.51 | 326.02 | A | | | |
| 61.133 | 2-chloro-N-[(1S,2S)-2-(2,4-difluorophenyl)cyclobutyl]pyridine-3-carboxamide | 1.33 | 323 | A | | | 130-133 |
| 61.134 | 2-bromo-N-[(1S,2S)-2-(2,4-difluorophenyl)cyclobutyl]thiophene-3-carboxamide | 1.62 | 371.91 | A | | | |
| 61.135 | N-[(1S,2S)-2-(2,4-difluorophenyl)cyclobutyl]-2,6-difluorobenzamide | 1.49 | 324.09 | A | | | |
| 61.136 | 5-bromo-N-[(1S,2S)-2-(2,4-difluorophenyl)cyclobutyl]-1,3-thiazole-4-carboxamide | 1.55 | 372.9 | A | | | |
| 61.137 | N-[(1S,2S)-2-(2,4-difluorophenyl)cyclobutyl]-2-(trifluoromethyl)thiophene-3-carboxamide | 1.64 | 362.06 | A | | | |
| 61.138 | N-[(1S,2S)-2-(2,4-difluorophenyl)cyclobutyl]-1,3-thiazole-4-carboxamide | 1.38 | 294.97 | A | | | |
| 61.139 | 2-chloro-N-[(1S,2S)-2-(2,4-difluorophenyl)cyclobutyl]thiophene-3-carboxamide | 1.62 | 327.96 | A | | | |
| 61.140 | N-[(1S,2S)-2-(2,4-difluorophenyl)cyclobutyl]-2-methylpyridine-3-carboxamide | 0.98 | 303.22 | A | | | 147-149 |
| 61.141 | 3-chloro-N-[(1S,2S)-2-(2,4-difluorophenyl)cyclobutyl]pyridine-2-carboxamide | 1.46 | 322.99 | A | | | 102-103 |
| 61.142 | 2-cyano-N-[(1S,2S)-2-(2,4-difluorophenyl)cyclobutyl]benzamide | 1.38 | 313.03 | A | | | |
| 61.143 | 3-bromo-N-[(1S,2S)-2-(2,4-difluorophenyl)cyclobutyl]thiophene-2-carboxamide | 1.71 | 371.9 | A | | | |

TABLE 61-continued

| Entry | Name | RT (min) | [M + H] (measured) | Method | RT' (min) | Chiral Method | MP (° C.) |
|---|---|---|---|---|---|---|---|
| 61.144 | N-[(1S,2S)-2-(2,4-difluorophenyl)cyclobutyl]-2-methylfuran-3-carboxamide | 1.47 | 292.15 | A | | | |
| 61.145 | N-[(1S,2S)-2-(2,4-difluorophenyl)cyclobutyl]-3-methyl-1,2-thiazole-4-carboxamide | 1.34 | 309.01 | A | | | |
| 61.146 | 3-bromo-N-[(1S,2S)-2-(2,4-difluorophenyl)cyclobutyl]pyridine-2-carboxamide | 1.49 | 366.94 | A | | | |
| 61.147 | N-[(1S,2S)-2-(2,4-difluorophenyl)cyclobutyl]-2-iodothiophene-3-carboxamide | 1.62 | 419.99 | A | | | |
| 61.148 | N-[(1S,2S)-2-(2,4-difluorophenyl)cyclobutyl]-4-methylfuran-3-carboxamide | 1.55 | 292.09 | A | | | |
| 61.149 | N-[(1S,2S)-2-(2,4-difluorophenyl)cyclobutyl]-2-(trifluoromethyl)benzamide | 1.01 | 356 | B | 6.02 | S | 83-85 |
| 61.150 | 3-chloro-N-[(1S,2S)-2-(2,4-difluorophenyl)cyclobutyl]pyrazine-2-carboxamide | 0.91 | 324 | B | 6.43 | T | 123-124 |
| 61.151 | N-[(1S,2S)-2-(2,4-difluorophenyl)cyclobutyl]-3-(trifluoromethyl)pyridine-2-carboxamide | 1.57 | 357.2 | A | | | 106-108 |
| 61.152 | N-[(1S,2S)-2-(2,4-dichlorophenyl)cyclobutyl]-3-methylpyridazine-4-carboxamide | 0.90 | 336 | B | | | |
| 61.153 | 4-chloro-N-[(1S,2S)-2-(2,4-dichlorophenyl)cyclobutyl]-2,5-dimethylpyrazole-3-carboxamide | 1.08 | 372 | B | | | |
| 61.154 | N-[(1S,2S)-2-(4-fluorophenyl)cyclobutyl]-2-(trifluoromethyl)pyridine-3-carboxamide | | | | 3.70 | H | 132-133 |
| 61.155 | N-[(1S,2S)-2-(4-bromophenyl)cyclobutyl]-2-(trifluoromethyl)pyridine-3-carboxamide | | | | 3.87 | H | 151-152 |
| 61.156 | N-[(1S,2S)-2-(4-bromophenyl)cyclobutyl]-3-(trifluoromethyl)pyrazine-2-carboxamide | | | | 24.23 | O | 189-190 |
| 61.157 | N-[(1S,2S)-2-(2,4-dichlorophenyl)cyclobutyl]-2,3,6-trifluorobenzamide | | | | | | 138-140 |
| 61.158 | 2-chloro-N-[(1S,2S)-2-(2,4-dichlorophenyl)cyclobutyl]-3,6-difluorobenzamide | | | | | | 86-88 |
| 61.159 | 2-bromo-N-[(1S,2S)-2-(2,4-dichlorophenyl)cyclobutyl]-3,6-difluorobenzamide | | | | | | 109-111 |
| 61.160 | N-[(1S,2S)-2-(2,4-dichlorophenyl)cyclobutyl]-5-methyl-1,3-oxazole-4-carboxamide | 1.04 | 325 | B | | | |
| 61.161 | 4-chloro-N-[(1S,2S)-2-(2,4-dichlorophenyl)cyclobutyl]-5-ethyl-2-methylpyrazole-3-carboxamide | | | | | | 107-109 |
| 61.162 | 3-bromo-N-[(1S,2S)-2-(2,4-dichlorophenyl)cyclobutyl]pyrazine-2-carboxamide | 1.01 | 400 | B | | | |
| 61.163 | 3-chloro-N-[(1S,2S)-2-(2,4-dichlorophenyl)cyclobutyl]pyridazine-4-carboxamide | 1.43 | 354 | B | | | 128-129 |
| 61.164 | 3-chloro-N-[(1S,2S)-2-(4-chlorophenyl)cyclobutyl]pyridazine-4-carboxamide | 1.29 | 322 | B | | | 152-153 |
| 61.165 | 4-chloro-N-[(1S,2S)-2-(2,4-dichlorophenyl)cyclobutyl]-2-(trifluoromethyl)pyridine-3-carboxamide | 1.77 | 423 | B | | | 148-150 |
| 61.166 | 4-chloro-N-[(1S,2S)-2-(4-chlorophenyl)cyclobutyl]-2-(trifluoromethyl)pyridine-3-carboxamide | 1.67 | 389 | B | | | 171-172 |
| 61.167 | N-[(1S,2S)-2-(2,4-dichlorophenyl)cyclobutyl]-4-(trifluoromethyl)pyridazine-3-carboxamide | 1.65 | 390 | B | | | 143-144 |
| 61.168 | N-[(1S,2S)-2-(4-chlorophenyl)cyclobutyl]-4-(trifluoromethyl)pyridazine-3-carboxamide | 1.53 | 356 | B | | | 174-172 |
| 61.169 | 4-chloro-N-[(1S,2S)-2-(4-chlorophenyl)cyclobutyl]-3-(trifluoromethyl)pyridine-2-carboxamide | 1.81 | 423 | B | | | 122-123 |
| 61.170 | N-[(1S,2S)-2-(4-chlorophenyl)cyclobutyl]-3-(trifluoromethyl)pyridazine-4-carboxamide | 1.46 | 356 | B | | | 166-167 |
| 61.171 | 4-chloro-N-[(1S,2S)-2-(4-chlorophenyl)cyclobutyl]-3-(trifluoromethyl)pyridine-2-carboxamide | 1.69 | 389 | B | | | 129-130 |
| 61.172 | N-[(1S,2S)-2-(2,4-dichlorophenyl)cyclobutyl]-3,6-difluoro-2-(trifluoromethyl)benzamide | | | | | | |
| 61.173 | 2-bromo-N-[(1S,2S)-2-(2,4-dichlorophenyl)cyclobutyl]furan-3-carboxamide | 1.10 | 388 | B | 10.65 | U | |
| 61.174 | N-[(1S,2S)-2-(2,4-dichlorophenyl)cyclobutyl]-2-(trifluoromethyl)furan-3-carboxamide | 1.11 | 378 | B | | | |
| 61.175 | N-[(2S,3S)-2-(2,4-difluorophenyl)oxetan-3-yl]-2-(trifluoromethyl)benzamide | | | | 2.27 | P | 78-80 |
| 61.176 | N-[(2S,3S)-2-[2-fluoro-4-(trifluoromethyl)phenyl]oxetan-3-yl]-2-(trifluoromethyl)benzamide | | | | 2.39 | Q | |
| 61.177 | N-[(1S,2S)-2-(2,4-dichlorophenyl)cyclobutyl]-3-(trifluoromethyl)pyridazine-4-carboxamide | 1.59 | 390 | B | | | 195-196 |
| 61.178 | N-[(1S,2S)-2-(2,4-difluorophenyl)cyclobutyl]-2-(difluoromethyl)pyridine-3-carboxamide | 1.00 | 371 | B | | | |
| 61.179 | 2-(difluoromethyl)-N-[(1S,2S)-2-(2,4-difluorophenyl)cyclobutyl]pyridine-3-carboxamide | 0.89 | 339 | B | | | |
| 61.180 | 2-bromo-N-[(1S,2S)-2-(2,4-difluorophenyl)cyclobutyl]furan-3-carboxamide | | | | | | 109-111 |
| 61.181 | N-[(1S,2S)-2-(2,4-difluorophenyl)cyclobutyl]-2-(trifluoromethyl)furan-3-carboxamide | | | | | | 91-92 |
| 61.182 | 2-bromo-N-[(1S,2S)-2-(4-chlorophenyl)cyclobutyl]furan-3-carboxamide | | | | | | 150-152 |

TABLE 62

| Entry | Name | RT (min) | [M + h] (measured) | Method | MP (° C.) |
|---|---|---|---|---|---|
| 62.1 | N-[(1,2 trans)-2-(2,4-difluorophenyl)cyclobutyl]-2-(trifluoromethyl)benzamide | 1.03 | 356 | B | 116-120 |
| 62.2 | 3-chloro-N-[(1,2 trans)-2-(2,4-difluorophenyl)cyclobutyl]pyrazine-2-carboxamide | 0.93 | 324 | B | 150-152 |
| 62.3 | N-[(1,2 trans)-2-(2,4-difluorophenyl)cyclobutyl]-1-methyl-3-(trifluoromethyl)pyrazole-4-carboxamide | 0.96 | 360 | B | 133-135 |
| 62.4 | 3-bromo-N-[(1,2 trans)-2-(2,4-difluorophenyl)cyclobutyl]pyridine-2-carboxamide | 0.98 | 367 | B | 134-137 |

TABLE 62-continued

| Entry | Name | RT (min) | [M + h] (measured) | Method | MP (° C.) |
|---|---|---|---|---|---|
| 62.5 | 3-chloro-N-[(1,2 trans)-2-(2,4-difluorophenyl)cyclobutyl]pyridine-2-carboxamide | 0.97 | 323 | B | 122-123 |
| 62.6 | 2-chloro-N-[(1,2 trans)-2-(2,4-difluorophenyl)cyclobutyl]pyridine-3-carboxamide | 0.9 | 323 | B | 128-130 |
| 62.7 | N-[(1,2 trans)-2-(2,4-difluorophenyl)cyclobutyl]-3-(trifluoromethyl)pyridine-2-carboxamide | 0.99 | 357 | B | 82-86 |
| 62.8 | N-[(1,2 trans)-2-[4-(difluoromethoxy)phenyl]cyclobutyl]-2-(trifluoromethyl)benzamide | 1.8 | 386 | B | |
| 62.9 | N-[(1,2 trans)-2-[4-(difluoromethoxy)phenyl]cyclobutyl]-2,6-difluoro-benzamide | 1.74 | 354 | B | |
| 62.10 | N-[(1,2 trans)-2-(4-chloro-2-fluoro-phenyl)cyclobutyl]-2-(trifluoromethyl)benzamide | | | | 128-130 |
| 62.11 | N-[(1,2 trans)-2-(4-chloro-2-fluoro-phenyl)cyclobutyl]-2,6-difluoro-benzamide | | | | 117-119 |
| 62.12 | N-[(1,2 trans)-2-(2,4-dichlorophenyl)cyclobutyl]-2-(trifluoromethyl)benzamide | | | | 147-148 |
| 62.13 | N-[(1,2 trans)-2-phenylcyclobutyl]-2-(trifluoromethyl)benzamide | | | | 95-98 |
| 62.14 | N-[(1,2 trans)-2-(4-chlorophenyl)cyclobutyl]-2-(trifluoromethyl)benzamide | | | | 117-119 |
| 62.15 | N-[(1,2 trans)-2-(2,4-dichlorophenyl)cyclobutyl]-2-(trifluoromethyl)pyridine-3-carboxamide | | | | 112-115 |

Analytical Methods

Method A

ACQUITY SQD Mass Spectrometer from Waters (Single quadrupole mass spectrometer)

Ionisation method: Electrospray

Polarity: positive ions

Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method B

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 ⌞ m, 30×2.1 mm, Temp: 60° C., DAD Wavelength range (nm): 210 to 500, Solvent Gradient: A=water+5% MeOH+0.05% HCOOH, B=Acetonitrile+0.05 HCOOH: gradient: gradient: 0 min 0% B, 100% A; 1.2-1.5 min 100% B; Flow (ml/min) 0.85

Method C (Chiral)

Waters UPLC-HClass from Waters: solvent degasser, quaternary pump and PDA detector Column: Chiralpak IC, length (mm) 100, internal diameter (mm) 4.6, particle size (µ) 3, wavelength (nm): 240 nm, solvent: Isocratic Heptane:EtOH 80:20, injection volume 2 µl, flow (ml/min) 1.0

Method D (Chiral)

Waters UPLC-HClass from Waters: solvent degasser, quaternary pump and PDA detector Column: Chiralpak IC, length (mm) 100, internal diameter (mm) 4.6, particle size (µ) 3, wavelength (nm): 277 nm, solvent: Isocratic Heptane:EtOH 80:20, injection volume 2 µl, flow (ml/min) 1.0

Method E (Chiral)

Waters UPLC-HClass from Waters: solvent degasser, quaternary pump and PDA detector Column: Chiralpak IE, length (mm) 100, internal diameter (mm) 4.6, particle size (µ) 3, wavelength (nm): 220 nm, solvent: Isocratic Heptane:iPrOH 70:30, injection volume 2 µl, flow (ml/min) 1.0

Method F (Chiral)

Waters UPLC-HClass from Waters: solvent degasser, quaternary pump and PDA detector Column: Chiralpak IC, length (mm) 100, internal diameter (mm) 4.6, particle size (µ) 3, wavelength (nm): 260 nm, solvent: Isocratic Heptane:EtOH:Et$_2$NH 70:30:0.1, injection volume 2 µl, flow (ml/min) 1.0

Method G

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 ⌞ m, 30×2.1 mm, Temp: 60° C., DAD Wavelength range (nm): 210 to 500, Solvent Gradient: A=water+5% MeOH+0.05% HCOOH, B=Acetonitrile+0.05 HCOOH: gradient: gradient: 0 min 0% B, 100% A; 2.7-3.0 min 100% B; Flow (ml/min) 0.85

Method H (Chiral)

Waters UPLC-HClass from Waters: solvent degasser, quaternary pump and PDA detector Column: Chiralpak IC, length (mm) 100, internal diameter (mm) 4.6, particle size (µ) 3, wavelength (nm): 260 nm, solvent: Isocratic Heptane:EtOH 80:20, injection volume 2 µl, flow (ml/min) 1.0

Method I (Chiral)

Waters UPLC-HClass from Waters: solvent degasser, quaternary pump and PDA detector Column: Chiralpak IC, length (mm) 100, internal diameter (mm) 4.6, particle size (µ) 3, wavelength (nm): 260 nm, solvent: Isocratic Heptane:iPrOH 90:10, injection volume 2 µl, flow (ml/min) 1.0

Method J (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 250 nm, solvent: Isocratic Heptane:iPrOH 80:20, injection volume 2 µl, flow (ml/min) 1.0

Method K (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 270 nm, solvent: Isocratic Heptane:iPrOH 90:10, injection volume 2 µl, flow (ml/min) 1.0

Method L (Chiral)
Waters UPLC-HClass from Waters: solvent degasser, quaternary pump and PDA detector
Column: Chiralpak IA, length (mm) 100, internal diameter (mm) 4.6, particle size (µ) 3, wavelength (nm): 260 nm, solvent: Isocratic Heptane:iPrOH 90:10, injection volume 2 µl, flow (ml/min) 1.0

Method M (Chiral)
Waters UPLC-HClass from Waters: solvent degasser, quaternary pump and PDA detector
Column: Chiralpak ID, length (mm) 100, internal diameter (mm) 4.6, particle size (µ) 3, wavelength (nm): 265 nm, solvent: Isocratic TBME: EtOH 99:01, injection volume 2 µl, flow (ml/min) 1.0

Method N (Chiral)
Waters UPLC-HClass from Waters: solvent degasser, quaternary pump and PDA detector
Column: Chiralpak IA, length (mm) 100, internal diameter (mm) 4.6, particle size (µ) 3, wavelength (nm): 270 nm, solvent: Isocratic TBME: EtOH 99.5:0.5, injection volume 2 µl, flow (ml/min) 1.0

Method O (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 260 nm, solvent: Isocratic Heptane:iPrOH 95:05, injection volume 2 µl, flow (ml/min) 1.0

Method P (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 260 nm, solvent: Isocratic Heptane: AcOEt 70:30, injection volume 2 µl, flow (ml/min) 1.0

Method Q (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 260 nm, solvent: Isocratic Heptane: AcOEt 80:20, injection volume 2 µl, flow (ml/min) 1.0

Method R
ZQ2000 Mass Spectrometer from Waters (Single quadrupole mass spectrometer)
Ionisation method: Electrospray
Polarity: positive ions
Capillary (kV) 3.5, Cone (V) 60.00, Extractor (V) 3.00, Source Temperature (° C.) 150, Desolvation Temperature (° C.) 350, Cone Gas Flow (L/Hr) 50, Desolvation Gas Flow (L/Hr) 800
Mass range: 140 to 800 Da
DAD Wavelength range (nm): 210 to 400

Method Waters ACQUITY UPLC with the following HPLC gradient conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method S (Chiral)
Waters UPLC-HClass from Waters: solvent degasser, quaternary pump and PDA detector
Column: Chiralpak ID, length (mm) 100, internal diameter (mm) 4.6, particle size (µ) 3, wavelength (nm): 260 nm, solvent: Isocratic Heptane: AcOEt 80:20, injection volume 2 µl, flow (ml/min) 1.0

Method T (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 270 nm, solvent: Isocratic Heptane:EtOH 80:20, injection volume 2 µl, flow (ml/min) 1.0

Method U (Chiral)
Waters UPLC-HClass from Waters: solvent degasser, quaternary pump and PDA detector
Column: Chiralpak IC, length (mm) 100, internal diameter (mm) 4.6, particle size (µ) 3, wavelength (nm): 265 nm, solvent: Isocratic Heptane: AcOEt 90:10, injection volume 2 µl, flow (ml/min) 1.0

Method V (Chiral)
Waters UPLC-HClass from Waters: solvent degasser, quaternary pump and PDA detector
Column: Chiralpak ID, length (mm) 100, internal diameter (mm) 4.6, particle size (µ) 3, wavelength (nm): 225 nm, solvent: Isocratic Heptane:iPrOH 90:10, injection volume 2 µl, flow (ml/min) 1.0

Method W (Chiral)
Waters UPLC-HClass from Waters: solvent degasser, quaternary pump and PDA detector
Column: Chiralpak ID, length (mm) 100, internal diameter (mm) 4.6, particle size (µ) 3, wavelength (nm): 270 nm, solvent: Isocratic Heptane:EtOH: Et2NH 95:5:0.1, injection volume 2 µl, flow (ml/min) 1.0

Method X (Chiral)
Waters UPLC-HClass from Waters: solvent degasser, quaternary pump and PDA detector
Column: Chiralpak IA, length (mm) 100, internal diameter (mm) 4.6, particle size (µ) 3, wavelength (nm): 230 nm, solvent: Isocratic TBME: EtOH 98:2, injection volume 2 µl, flow (ml/min) 1.0

Method Y (Chiral)
Waters UPLC-HClass from Waters: solvent degasser, quaternary pump and PDA detector
Column: Chiralpak IA, length (mm) 100, internal diameter (mm) 4.6, particle size (µ) 3, wavelength (nm): 227 nm, solvent: Isocratic EtOH.MeOH 50:50, injection volume 2 µl, flow (ml/min) 1.0

Method Z (Chiral) Waters UPLC-HClass from Waters: solvent degasser, quaternary pump and PDA detector Column: Chiralpak IA, length (mm) 100, internal diameter (mm) 4.6, particle size (μ) 3, wavelength (nm): 265 nm, solvent: Isocratic Heptane:iPrOH: Et$_2$NH 95:5:0.1, injection volume 2 μl, flow (ml/min) 1.0

Method AA (Chiral GC)

Chiral GC was conducted on a Thermo Focus GC Ultra, with a column from Astec Chiraldex BDM fused silica Capillary Column: 30 m, diam: 0.25 mm, 0.25 μm, H2 flow 1. ml/min, temp injector:

220° C., FID Detector: temp detector: 220° C., method: start at 150° C., hold 5 min 5° C./min until 200° C., hold 3 min, total time 18 min.

Biological Examples

*Meloidogyne* spp. (Root-Knot Nematode)

Nematicide, Contact Activity, Preventive.

Filter papers (9 cm×4.5 cm) with a small pocket were placed into plastic pouches (12 cm×6 cm). One cucumber cv. Toshka seed was placed in the centre of the filter paper pocket of all the pouches needed for a test. The cucumber seeds in the pouches were treated with test solutions at 200 ppm by pipetting the solution directly over the cucumber seed in the filter paper pocket in the pouch. Prior to application, the compound solution was prepared at twice the concentration required and the egg suspension is prepared with FORL nutrient solution with 3000 eggs/0.5 ml. After applying all the treatments, 3000 eggs (in 0.5 ml of FORL nutrient solution) were pipetted into the pouches. The pouches were incubated in a moist chamber for twelve days and watered regularly to maintain good filter paper moisture essential for the growing cucumber root system. After this period, the filter paper containing the germinated cucumber seedling was removed from the plastic pouch to assess the number of galls caused by *Meloidogyne* spp. per root system. Phytotoxicity was measured as a reduction of growth of the emerged cucumber seedling in comparison to the control.

The following compounds showed a greater than 80% reduction of galling compared to the untreated control:

60.5, 60.6, 60.8, 60.9, 60.10, 60.12, 60.13, 60.14, 60.15, 60.16, 60.18, 60.19, 60.20, 60.21, 60.22, 60.23, 60.26, 60.27, 60.28, 60.29, 60.31, 60.33, 60.34, 60.35, 60.37, 60.39, 60.44, 60.45, 60.46, 60.47, 60.48, 60.49, 60.50, 60.51, 60.52, 60.53, 60.54, 60.55, 60.56, 60.57, 60.103, 60.104, 60.105, 60.106, 60.107, 60.108, 60.109, 60.110, 60.112, 60.122, 60.123, 60.126, 60.127, 60.128, 60.129, 60.130, 60.131, 60.132, 60.133, 60.134, 60.137, 60.138, 60.139, 60.140, 60.143, 60.144, 60.146, 60.163, 60.165, 60.166, 60.168, 60.171, 60.172, 60.176, 60.177, 60.178, 60.179, 60.180, 60.181, 60.182, 60.183, 60.184, 60.185, 60.187, 60.188, 60.190, 60.191, 60.192, 60.193, 60.194, 60.195, 60.214, 60.233, 60.235, 60.236, 60.237, 60.238, 60.239, 60.240, 60.241, 60.242, 60.243, 60.244, 60.245, 60.246, 61.1, 61.5, 61.7, 61.8, 61.9, 61.10, 61.41, 61.60, 61.64, 61.66, 61.68, 61.69, 61.76, 61.77, 61.95, 61.99

*Heterodera schachtii* (Sugar Beet Cyst Nematode), Nematicide, Contact Activity

The tested application rate of each compound was 200 ppm. All solutions were brought to a concentration of 400 ppm, respectively, as they were subsequently diluted by adding the equivalent amount of water containing juvenile nematodes. After preparation of the suspensions, 1 ml of each suspension and concentration was transferred to 16-well assay plates with a total of three replicates per treatment. Approximately 500 juveniles of *Heterodera schachtii* were added in 1 ml of water to each well. Nematodes in water served as controls. The plates were placed in a dark box and stored at room temperature. Nematode paralysis was determined after 24 hours incubation at 25° C. in darkness. Nematodes that showed no movement were considered immotile.

The following compounds showed a greater than 75% nematode immobilization compared to the untreated control:

60.6, 60.7, 60.8, 60.9, 60.10, 60.11, 60.15, 60.16, 60.18, 60.20, 60.21, 60.22, 60.23, 60.24, 60.26, 60.27, 60.28, 60.29, 60.31, 60.33, 60.34, 60.35, 60.37, 60.39, 60.40, 60.42, 60.43, 60.44, 60.45, 60.46, 60.47, 60.48, 60.49, 60.50, 60.51, 60.52, 60.53, 60.54, 60.55, 60.56, 60.57, 60.58, 60.59, 60.60, 60.61, 60.62, 60.63, 60.64, 60.65, 60.66, 60.67, 60.68, 60.69, 60.70, 60.71, 60.72, 60.73, 60.74, 60.75, 60.78, 60.79, 60.86, 60.88, 60.89, 60.90, 60.93, 60.94, 60.95, 60.96, 60.97, 60.98, 60.103, 60.104, 60.105, 60.106, 60.107, 60.108, 60.109, 60.110, 60.111, 60.112, 60.113, 60.114, 60.116, 60.134, 60.135, 60.136, 60.137, 60.138, 60.139, 60.140, 60.142, 60.143, 60.144, 60.146, 60.149, 60.165, 60.166, 60.167, 60.168, 60.169, 60.176, 60.178, 60.179, 60.180, 60.182, 60.183, 60.184, 60.185, 60.186, 60.187, 60.190, 60.191, 60.192, 60.193, 60.194, 60.195, 60.199, 60.203, 60.204, 60.219, 60.229, 60.235, 60.236, 60.237, 60.238, 60.239, 60.241, 60.244, 60.245, 60.246, 61.1, 61.2, 61.3, 61.4, 61.5, 61.6, 61.7, 61.8, 61.9, 61.10, 61.11, 61.14, 61.15, 61.21, 61.22, 61.23, 61.24, 61.25, 61.26, 61.36, 61.41, 61.46, 61.47, 61.52, 61.53, 61.54, 61.56, 61.58, 61.59, 61.60, 61.62, 61.64, 61.65, 61.66, 61.68, 61.69, 61.70, 61.72, 61.73, 61.74, 61.76, 61.77, 61.79, 61.81, 61.83, 61.84, 61.85, 61.86, 61.87, 61.88, 61.89, 61.90, 61.91, 61.92, 61.93, 61.95, 61.96, 61.97, 61.98, 61.99, 61.100, 61.101, 61.102, 61.103, 61.104, 61.106, 61.108, 61.109, 61.110, 61.113, 61.114, 61.116, 61.117, 61.118, 61.119, 61.121, 61.122, 61.124, 61.125, 61.126, 61.127, 61.129, 61.131, 61.133, 61.136, 61.137, 61.140, 61.141, 61.143, 61.144, 61.146, 61.151, 61.154, 61.155, 61.156, 61.158, 61.159, 61.162, 61.167, 61.172, 61.173, 61.174, 61.175, 61.176

*Meloidogyne* spp. (Root-Knot Nematode)

Nematicide, Contact Activity, Preventive

Cucumber cv. Toshka seeds were sown directly into pots filled with a sandy substrate. Six days later pots were each treated with 5 ml of a WP10 suspension of the test compound. Hereafter, pots were inoculated with 3000 eggs of *M. incognita*. The trial was harvested fourteen days after trial application and inoculation. Root galling was assessed according to Zeck's gall index (Zeck W. M. (1971) Ein Bonitierungsschema zur Feldauswertung von Wurzelgallenbefall. Pflanzenschutznachrichten Bayer 24, 1: 144-147). Phytotoxicity was measured as a reduction of growth of the emerged cucumber seedling in comparison to the control.

The following compounds showed a greater than 80% reduction of galling compared to the untreated control:

60.1, 60.2, 60.3, 60.4, 60.5, 60.6, 60.7, 60.9, 60.10, 60.12, 60.13, 60.14, 60.15, 60.16, 60.18, 60.19, 60.20, 60.21, 60.22, 60.23, 60.24, 60.26, 60.27, 60.28, 60.29, 60.30, 60.31, 60.32, 60.33, 60.34, 60.35, 60.37, 60.39, 60.40, 60.41, 60.44, 60.45, 60.46, 60.47, 60.48, 60.49, 60.50, 60.51, 60.52, 60.53, 60.54, 60.55, 60.56, 60.57, 60.103, 60.104, 60.105, 60.106, 60.107, 60.108, 60.109, 60.110, 60.111, 60.112, 60.113, 60.115, 60.116, 60.122, 60.125, 60.126, 60.127, 60.128, 60.129, 60.130, 60.131, 60.132, 60.133, 60.134, 60.135, 60.136, 60.137, 60.138, 60.139, 60.140, 60.142, 60.143, 60.144, 60.146, 60.148, 60.149, 60.151, 60.155, 60.163, 60.165, 60.166, 60.168, 60.171, 60.172, 60.176, 60.177, 60.178, 60.179, 60.180, 60.181, 60.182, 60.183, 60.184, 60.185, 60.187, 60.188, 60.190, 60.191, 60.192, 60.193, 60.194, 60.195, 60.214, 60.233, 60.234, 60.235, 60.236, 60.237, 60.238, 60.239, 60.240, 60.241, 60.242, 60.243, 60.244, 60.245, 60.246, 61.1, 61.5, 61.6, 61.7, 61.8, 61.9, 61.10, 61.14, 61.15, 61.16, 61.17, 61.18, 61.20, 61.21, 61.22, 61.23, 61.24, 61.25, 61.26, 61.32, 61.38, 61.41, 61.44, 61.48, 61.49, 61.53, 61.54, 61.55, 61.58, 61.59, 61.60, 61.62, 61.64, 61.65, 61.66, 61.67, 61.68, 61.69, 61.70, 61.73, 61.74, 61.77, 61.79, 61.81, 61.84, 61.85, 61.86, 61.87, 61.88, 61.89, 61.90, 61.92, 61.95, 61.96, 61.97, 61.98, 61.99, 61.104, 61.106

*Meloidogyne* spp. (Root-Knot Nematode)

Nematicide, Contact Activity, Preventive

Coated tomato cv. Roter Gnom seeds were sown 0.5 to 1 cm deep in 45 ml pots filled with field soil. Then pots were infested with nematodes by pipetting 2000 eggs of *Meloidogyne* spp. within a 2 ml suspension on top of the seed. The seed hole was filled with soil hereafter. Assessment of phytotoxicity (in %) and root galling occurred 28 days after inoculation. The roots were washed free of soil debris and the gall index was assessed according to Zeck 1971 on a scale from 0 to 7.

Seed treatment rate: 1 mg AI/seed

The following compounds showed a greater than 80% reduction of galling compared to the untreated control:

60.6, 60.7, 60.8, 60.9, 60.48, 60.49, 60.51, 60.56, 60.107, 60.108, 60.126, 60.129, 60.134, 60.214, 60.236, 60.241, 60.245, 61.1, 61.3, 61.5, 61.7, 61.10

*Pratylenchus zeae* (Corn Lesion Nematode)

Nematicide, Contact Activity, Preventive

Coated corn cv. LG4620 seeds were sown 1 cm deep into 45 ml pots with soil (7:3 w/w—a mixture of 70% field soil and 30% quartz Sand). Two days after sowing the pots were infested with 1500 nematodes (all stages) of *Pratylenchus zeae* within a 2 ml suspension in two holes to the left and right of the seed hole. Assessment of phytotoxicity (in %) and nematode numbers within the root system occurred 7 days after inoculation. The upper plant part was cut off and the roots were washed free of soil debris. Nematodes within the roots were stained with acid fuchsin stain solution. Nematodes within the roots were quantified under a dissecting scope at 40×.

Seed treatment rate: 1 mg AI/seed

The following compounds showed a greater than 80% reduction of nematode population compared to the untreated control:

60.9, 60.38, 60.46, 60.49, 60.52, 60.214, 60.236, 61.1, 61.10

*Heterodera schachtii* (Sugar Beet Cyst Nematode)

Nematicide, Contact Activity, Preventive

Coated sugar beat cv. Impulse seeds were planted in 45 ml pots filled with field soil. Seven days after sowing pots were infested with 500 J2 of *Heterodera schachtii* within a 2 ml suspension in two holes to the left and right of the seedling. Assessment of nematode numbers per g of root occurred 10 days after inoculation. The upper plant part was cut off and the roots were washed free of soil debris. Nematodes within the roots were stained with acid fuchsin stain solution. Nematodes within the roots were quantified under a dissecting scope at 40×.

Seed treatment rate: 0.6 mg AI/seed

The following compounds showed a greater than 80% reduction of nematode population compared to the untreated control:

60.6, 60.46, 60.48, 60.49, 60.51, 60.52, 60.53, 60.54, 60.55, 60.56, 60.57, 60.139, 60.244, 61.3, 61.4, 61.10, 61.64, 61.92.

The invention claimed is:

1. A compound selected from

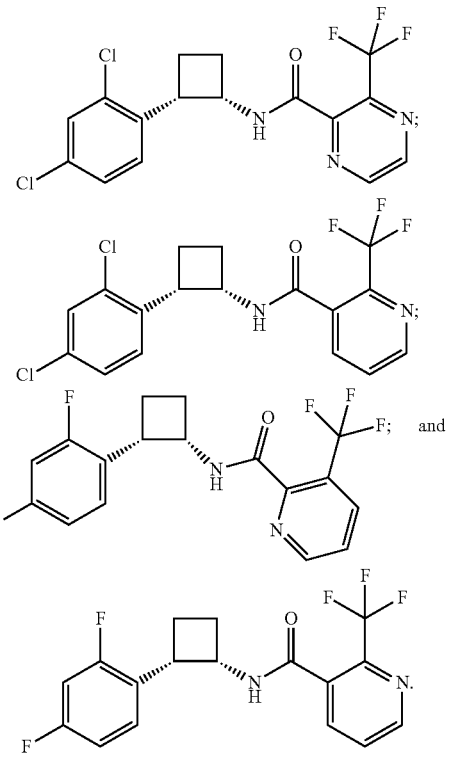

2. A composition comprising a compound of formula (I) selected from

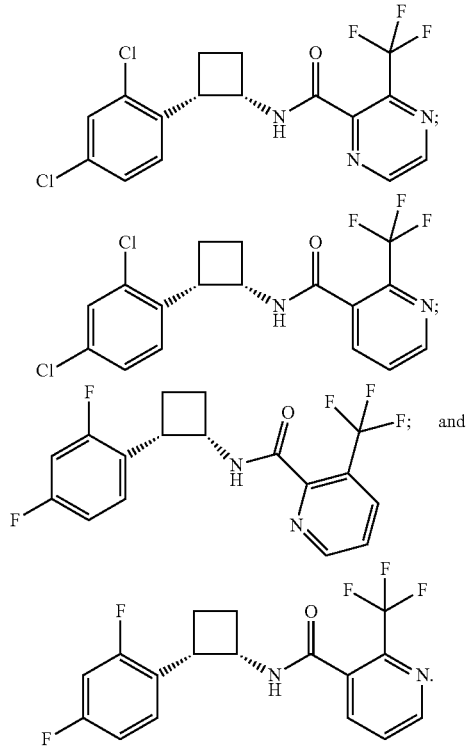

wherein the ratio of the compound of formula (I) to its enantiomer is greater than 1.5:1, greater than 2.5:1, greater than 4:1, greater than 9:1, or greater than 20:1.

3. A compound according to claim 1 which is

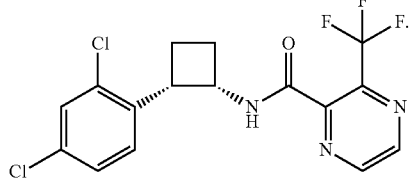

4. A compound according to claim 1 which is

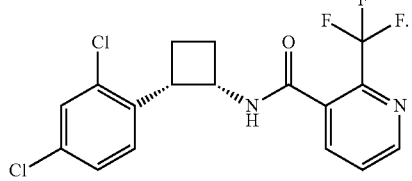

5. A compound according to claim 1 which is

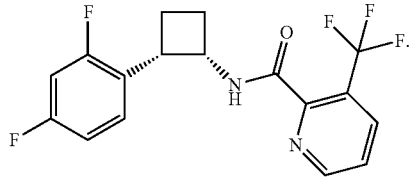 [SMILES: O=C(N[C@H]1CC[C@H]1c1ccc(F)cc1F)c1ncccc1C(F)(F)F]

6. A compound according to claim 1 which is

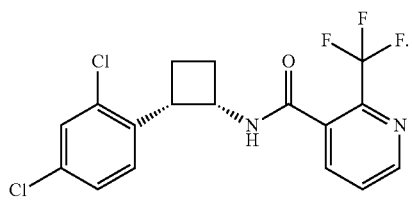

7. A composition according to claim 2 comprising a compound of formula

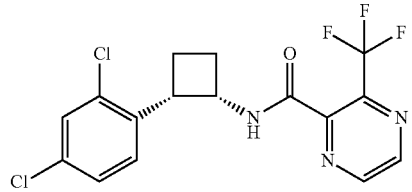

wherein the ratio of the compound of formula (I) to its enantiomer is greater than 1.5:1, greater than 2.5:1, greater than 4:1, greater than 9:1, or greater than 20:1.

8. A composition according to claim 2 comprising a compound of formula

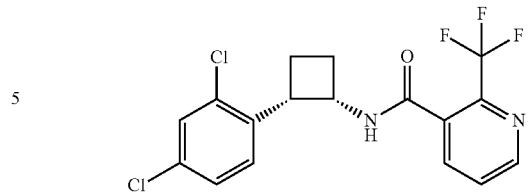

wherein the ratio of the compound of formula (I) to its enantiomer is greater than 1.5:1, greater than 2.5:1, greater than 4:1, greater than 9:1, or greater than 20:1.

9. A composition according to claim 2 comprising a compound of formula

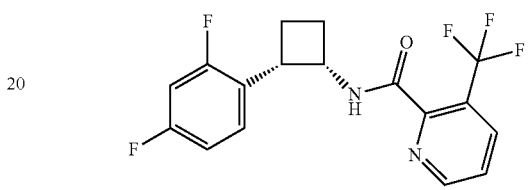

wherein the ratio of the compound of formula (I) to its enantiomer is greater than 1.5:1, greater than 2.5:1, greater than 4:1, greater than 9:1, or greater than 20:1.

10. A composition according to claim 2 comprising a compound of formula

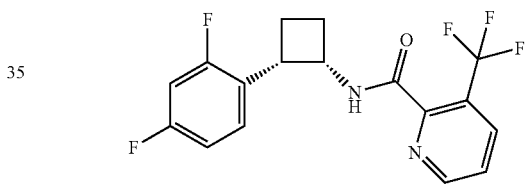

wherein the ratio of the compound of formula (I) to its enantiomer is greater than 1.5:1, greater than 2.5:1, greater than 4:1, greater than 9:1, or greater than 20:1.

11. A composition according to claim 2 comprising a compound of formula

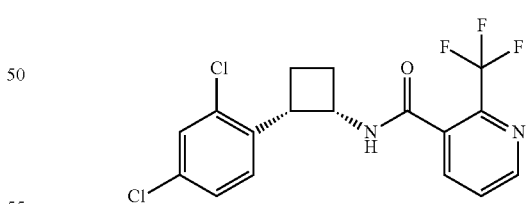

wherein the ratio of the compound of formula (I) to its enantiomer is greater than 1.5:1, greater than 2.5:1, greater than 4:1, greater than 9:1, or greater than 20:1.

12. The composition according to claim 2, wherein the ratio of the compound of formula (I) to its enantiomer is greater than 9:1.

13. A method of controlling pests in soil, the method comprising: applying to the soil a composition according to claim 12.

14. The method of claim 13, wherein the application to the soil is through a solid carrier treated with the composition.

15. The method of claim 14, wherein the solid carrier is a seed.

16. The method of claim 13, wherein the pest is a nematode.

17. The composition of claim 2, wherein the ratio of the compound of formula (I) to its enantiomer is greater than 20:1.

* * * * *